US012595504B2

(12) United States Patent
Fourmy et al.

(10) Patent No.: US 12,595,504 B2
(45) Date of Patent: Apr. 7, 2026

(54) METHODS FOR SCREENING COMPOUNDS FOR BACTERICIDAL ACTIVITY AND FOR DETERMINING THE SENSITIVITY OF BACTERIAL SAMPLES

(71) Applicants: Centre National de la Recherche Scientifique (CNRS), Paris (FR); Universite Paris-Saclay, Gif sur Yvette (FR)

(72) Inventors: Dominique Fourmy, Chevreuse (FR); Satoko Yoshizawa, Chevreuse (FR); Marie Ebeyer-Masotta, Franconville (FR); Jean-Luc Pernodet, Cachan (FR)

(73) Assignees: Centre National de la Recherche Scientifique (CNRS), Paris (FR); Universite Paris-Saclay, Gif sur Yvette (FR)

( * ) Notice: Subject to any disclaimer, the term of this patent is extended or adjusted under 35 U.S.C. 154(b) by 443 days.

(21) Appl. No.: 18/018,704

(22) PCT Filed: Aug. 2, 2021

(86) PCT No.: PCT/EP2021/071592
§ 371 (c)(1),
(2) Date: Jan. 30, 2023

(87) PCT Pub. No.: WO2022/023582
PCT Pub. Date: Feb. 3, 2022

(65) Prior Publication Data
US 2023/0304065 A1 Sep. 28, 2023

(30) Foreign Application Priority Data
Jul. 31, 2020 (EP) ..................................... 20305886

(51) Int. Cl.
*C12Q 1/20* (2006.01)
*C12Q 1/66* (2006.01)

(52) U.S. Cl.
CPC ................. *C12Q 1/20* (2013.01); *C12Q 1/66* (2013.01); *G01N 2333/90241* (2013.01)

(58) Field of Classification Search
None
See application file for complete search history.

(56) References Cited

U.S. PATENT DOCUMENTS 6,074,859 A * 6/2000 Hirokawa ............ C12N 9/0069
435/8
2023/0110491 A1* 4/2023 Ihssen ...................... C12Q 1/34
435/33

FOREIGN PATENT DOCUMENTS

WO WO-2019/162301 A1 8/2019
WO WO-2021/176101 9/2021

OTHER PUBLICATIONS

Yap et al., Direct *E. coli* Cell Count at OD600, Tip Biosystems (2019); Available online at: https://www.tipbiosystems.com/wp-content/uploads/2023/12/AN102-E.coli-Cell-Count_2019_04_25.pdf (Year: 2019).*
Genbank Accession AAE43251.1, Sequence 7 from U.S. Pat. No. 6,074,859 (2001) (Year: 2001).*
Anand et al., *Effect of Streptomycin on Escherichia coli; Damage by Streptomycin to the Cell Membrane of Escherichia coli.*, 185 Nature 22-23 (Jan. 2, 1960).
*Antibiotic susceptibility diagnostics for the future*, 4 Nature Microbiology 1603 (2019).
Balaban et al., *Bacterial Persistence as a Phenotypic Switch*, 305 Science 1622-1625 (2004).
Berg et al., *A genetically encoded fluorescent reporter of ATP/ADP ratio*, 6(2) Nat Methods 161-166 (Feb. 2009).
Chung et al., *Rapid β-lactam-induced lysis requires successful assembly of the cell division machinery*, 106(51) Proc. Natl. Acad. Sci. 21872-21877 (Dec. 22, 2009).
Daugelavičius et al. *Stages of Polymyxin B Interaction with the Escherichia coli Cell Envelope*, 44(11) Antimicrobial Agents and Chemotherapy 2969-2978 (Nov. 2000).
Davis, *Mechanism of Bactericidal Action of Aminoglycosides*, 51(3) Microbiological Reviews 341-50 (Sep. 1987).
De Rautlin de la Roy et al., *Kinetics of Bactericidal Activity of Antibiotics Measured by Luciferin-Luciferase Assay*, 6(3) Journal of Bioluminescence Chemiluminescence 193-201 (1991).
Deris et al., *Probing the Penetration of Antimicrobial Polymyxin Lipopeptides into Gram-Negative Bacteria*, 25 Bioconjugate Chemistry 750-760 (2014).
England et al., *NanoLuc: A Small Luciferase is Brightening up the Field of Bioluminescence*, 27(5) Bioconjug Chem. 1175-1187 (May 18, 2016).
Esnault et al., *Strong antibiotic production is correlated with highly active oxidative metabolism in Streptomyces coelicolor M145*, 7(200) Sci. Rep. 200 (Mar. 15, 2017).
Fredborg et al., *Real-Time Optical Antimicrobial Susceptibility Testing*, 51(7) Journal of Clinical Microbiology 2047-2053 (Apr. 17, 2013).
Gilbert et al., *Centrifugation injury of Gram-negative bacteria*, 27(4) Journal of Antimicrobial Chemotherapy 550-551 (Apr. 1, 1991).
Hall et al., *Engineered Luciferase Reporter from a Deep Sea Shrimp Utilizing a Novel Imidazopyrazinone Substrate*, 7 ACS Chemical Biology 1848-1857 (2012).
Heller et al., *A rapid method for post-antibiotic bacterial susceptibility*, 14(1) PLoS ONE 1-13 (Jan. 10, 2019).

(Continued)

*Primary Examiner* — Robert J Yamasaki
(74) *Attorney, Agent, or Firm* — Panitch Schwarze Belisario & Nadel LLP; Erin M. Dunston

(57) ABSTRACT

The present invention relates to a method for screening compounds for bactericidal activity using thermostable luciferase and based on a real-time bioluminescence measurement. The present invention further relates to a method for determining the sensitivity of a bacterial sample originating from a subject suffering from a bacterial infection to a group of known antibiotics and to a method for assessing the minimum inhibitory concentration (MIC) of a bactericidal compound.

20 Claims, 53 Drawing Sheets
Specification includes a Sequence Listing.

(56)                    References Cited

OTHER PUBLICATIONS

Hirokawa et al., *Improved practical usefulness of firefly luciferase by gene chimerization and random mutagenesis*, 1597 Biochimica Et Biophysica Acta 271-279 (2002).

Ihssen et al., *Real-time monitoring of extracellular ATP in bacterial cultures using thermostable luciferase*, 16(1) PLoS ONE 1-23 (Jan. 22, 2021).

Imamura et al., *Visualization of ATP levels inside single living cells with fluorescence resonance energy transfer-based genetically encoded indicators*, 106(37) PNAS 15651-15656 (Sep. 15, 2009).

Jathoul et al., *A Dual-Color Far-Red to Near-Infrared Firefly Luciferin Analogue Designed for Multiparametric Bioluminescence Imaging*, 53(48) Angew Chem Int Ed Engl. 13059-13063 (2014).

Keren et al., *Specialized Persister Cells and the Mechanism of Multidrug Tolerance in Escherichia coli*, 186(24) Journal of Bacteriology 8172-8180 (Dec. 2004).

Kim et al., *A Luciferase/Single-Walled Carbon Nanotube Conjugate for Near-Infrared Fluorescent Detection of Cellular ATP*, 49 Angew. Chem. Int. Ed. 1456-1459 (2010).

Kuchimaru et al., *A luciferin analogue generating near-infrared bioluminescence achieves highly sensitive deep-tissue imaging*, 14(7) Nat Commun. 1-8 (Jun. 14, 2016).

Lee et al., *Targeting a bacterial stress response to enhance antibiotic action*, 106(34) PNAS 14570-15705 (Aug. 25, 2009).

Ling et al., *A new antibiotic kills pathogens without detectable resistance*, 517(7535) Nature 455-459 (Jan. 22, 2015).

Meng et al., *Gene cloning and heterologous expression of a serine protease from Streptomyces fradiae var.k11*, 53 Can. J. Microbiol. 186-195 (2007).

Neidhardt et al. *Culture Medium for Enterobacteria*, 119 Journal of Bacteriology 736-747 (Sep. 1974).

Nielsen et al., *Aptamers Embedded in Polyacrylamide Nanoparticles: A Tool for in Vivo Metabolite Sensing*, 4(8) ACS Nano 4361-4370 (Aug. 24, 2010).

Nilsson, *New Rapid Bioassay of Gentamicin Based on Luciferase Assay of Extracellular ATP in Bacterial Cultures*, 14(6) Antimicrobial Agents and Chemotherapy 812-816 (Jan. 1, 1978).

Procópio et al., *Antibiotics produced by Streptomyces*, 16(5) Braz. J. Infect. Dis. Off. Publ. Braz. Soc. Infect. Dis. 466-471 (2012).

Rolain et al., *Real-time PCR for universal antibiotic susceptibility testing*, 54(2) Journal of Antimicrobial Chemotherapy 538-541 (Jul. 1, 2004).

Roth et al., Purine Nucleotide Excretion by *Escherichia coli* in the Presence of Streptomycin, 37 *Biochim. Biophys. Acta* 398-405 (Jan. 29, 1960).

Safavieh et al., *Rapid Real-Time Antimicrobial Susceptibility Testing with Electrical Sensing on Plastic Microchips with Printed Electrodes*, 9(14) ACS Applied Materials & Interfaces 12832-12840 (Mar. 30, 2017).

Saito et al., *Luminescent proteins for high-speed single-cell and whole-body imaging*, 3 Nature Communications 1-9 (2012).

Schneider et al., *Relationship between Growth Rate and ATP Concentration in Escherichia coli: a Bioassay for Available Cellular ATP*, 279(9) Journal of Biological Chemical 8262-8268 (Feb. 27, 2004).

Tantama et al., *Imaging energy status in live cells with a fluorescent biosensor of the intracellular ATP-to-ADP ratio*, 4 Nat. Commun. 1-27 (2013).

Wilson, *Ribosome-targeting antibiotics and mechanisms of bacterial resistance*, 12 Nat. Rev. Microbiol. 35-48 (Jan. 2014).

Yaginuma et al., *Diversity in ATP concentrations in a single bacterial cell population revealed by quantitative single-cell imaging*, 4 Scientific Reports 1-7 (Oct. 6, 2014).

Yao et al., *Distinct single-cell morphological dynamics under beta-lactam antibiotics*, 48(5) Mol. Cell. 705-712 (Dec. 14, 2012).

Yeh et al., *Red-shifted luciferase-luciferin pairs for enhanced bioluminescence imaging*, 14(10) Nat. Methods 971-974 (Oct. 2017).

Yoshida et al., *BTeam, a Novel BRET-based Biosensor for the Accurate Quantification of ATP Concentration within Living Cells*, 6 Scientific Reports 1-9 (Dec. 21, 2016).

Zheng et al., *Aptamer Nano-Flares for Molecular Detection in Living Cells*, 9(9) Nano Lett. 3258-3261 (Sep. 2009).

* cited by examiner

B.
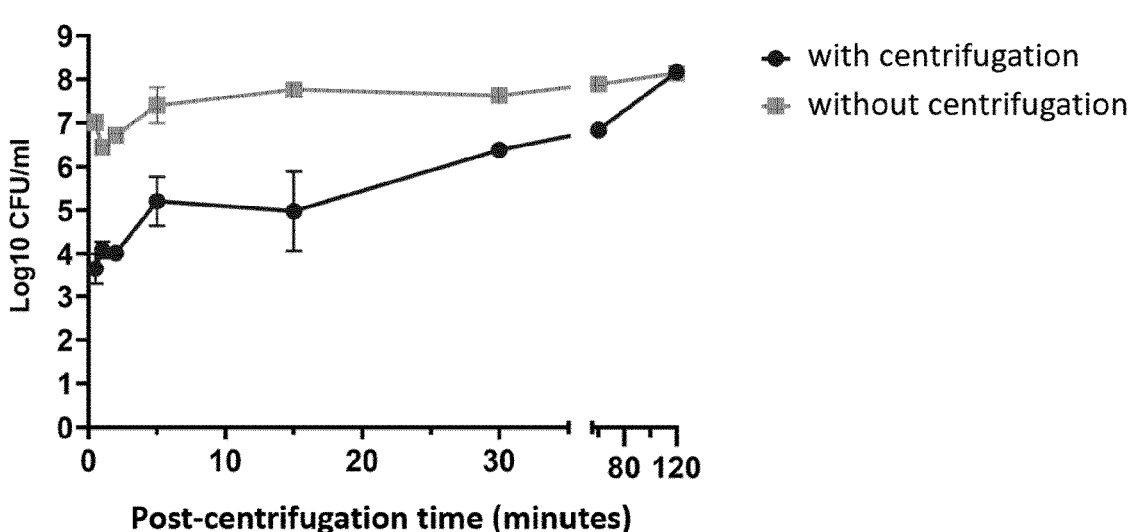
Figure 4 (followed)

A.

B.

Neomycin

Gentamicin C

Streptomycin

Kanamycin

Apramycin

Amikacin

Piperacillin

Ceftriaxome

Ampicillin

Amoxicillin

Ceftazidime

Cefixime

Cefoxitin

Cephalexin

Polymyxin B

Ciprofloxacin

Acid Nalidixic

Bleomycin

Zeocin

Fosfomycin

Trimethoprim

Nitrofurantoin

Rifampicin

Erythromycin

Tetracycline

Spectinomycin

Chloramphenicol

Puromycin

Azithromycin

A.

B.
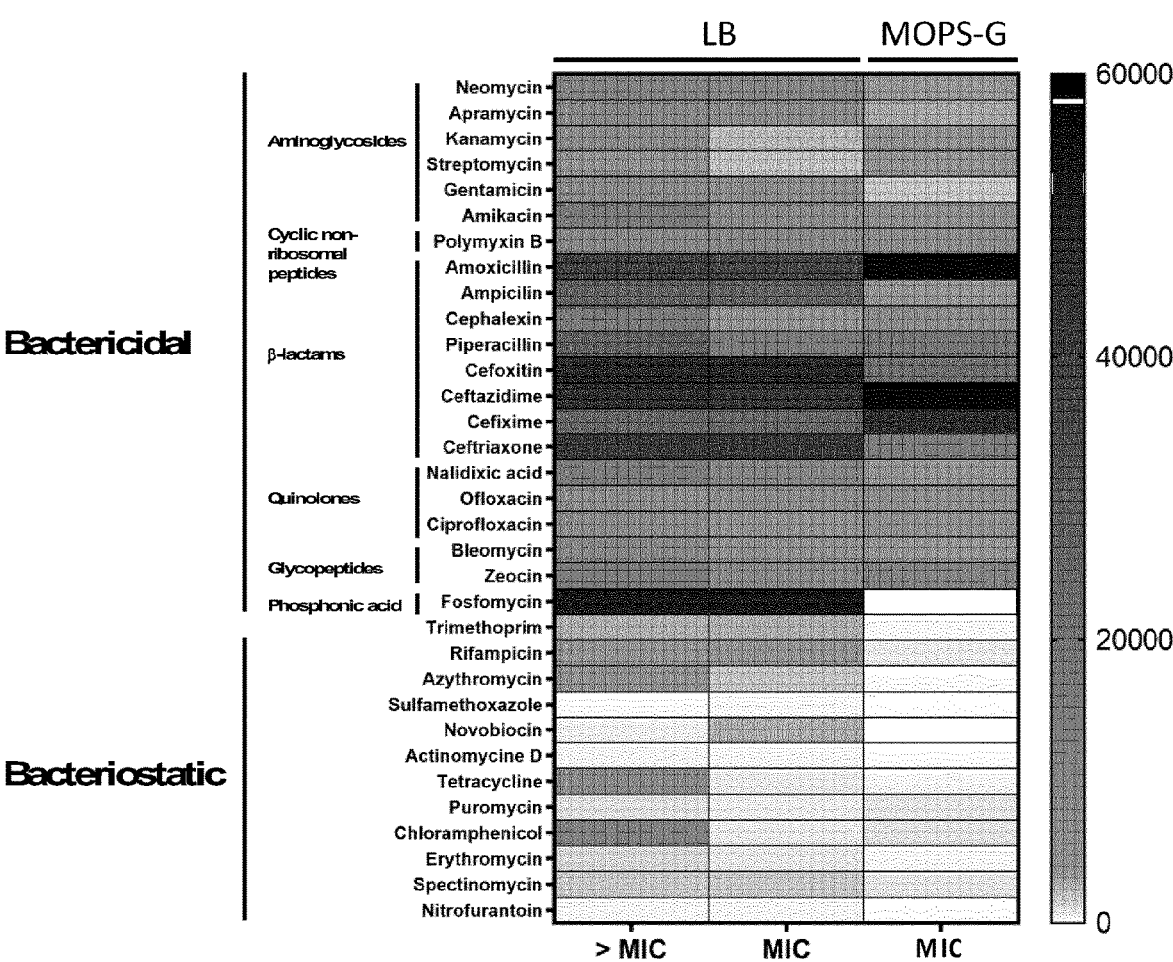
Figure 10 (followed)

A.

B.

A.

B.

Figure 16 (followed)

Culture of *Streptomyces fradiae* in Erlenmeyer flasks (7 days) in triplicate

Centrifugation (13000 rpm /15 min at 4°C)

Storage at -20°C
Defrost when needed

Overnight culture of *Escherichia coli*

Bacteria diluted and regrown in fresh media

*Escherichia coli*
$OD_{600} = 0.6$

*Escherichia coli*

Luciferin-luciferase reagent solution

Bioluminescence monitored during 4 hours under shaking (218 rpm) at 37°C

B.

C.

A.

B.

Bioluminescence based antimicrobial discovery

$$X = \frac{\text{Lag (MIC)-Plateau}}{\text{Amplitude}} \times 100$$

Gentamicin

Cephalexin

Streptomycin

Neomycin

Kanamycin

Ampicillin

Apramycin

Rifampicin

Amikacin

Nalidixic acid

Amoxicillin

Cefoxitin

Ceftriaxome

Ofloxacin

Cefixime

Fosfomycin

Ceftazidime

Bleomycin

Neomycin (medium MH OD600 0.3)

Neomycin (medium MH OD600 0.15)

A.

B.

SEQUENCE LISTING

<160> NUMBER OF SEQ ID NOS: 1

<210> SEQ ID NO 1

-continued

```
<211> LENGTH: 552
<212> TYPE: PRT
<213> ORGANISM: Artificial Sequence
<220> FEATURE:
<223> OTHER INFORMATION: Synthetic construct

<400> SEQUENCE: 1

Met Glu Asn Met Glu Asn Asp Glu Asn Ile Val Val Gly Pro Lys Pro
1               5                   10                  15

Phe Tyr Pro Ile Glu Glu Gly Ser Ala Gly Thr Gln Leu Arg Lys Tyr
            20                  25                  30

Met Glu Arg Tyr Ala Lys Leu Gly Ala Ile Ala Phe Thr Asn Ala Val
        35                  40                  45

Thr Gly Val Asp Tyr Ser Tyr Ala Glu Tyr Leu Glu Lys Ser Cys Cys
    50                  55                  60

Leu Gly Lys Ala Leu Gln Asn Tyr Gly Leu Val Val Asp Gly Arg Ile
65                  70                  75                  80

Ala Leu Cys Ser Glu Asn Cys Glu Glu Phe Phe Ile Pro Val Ile Ala
                85                  90                  95

Gly Leu Phe Ile Gly Val Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Asp Lys Val Ile Thr Val Gln Lys Thr
    130                 135                 140

Val Thr Thr Ile Lys Thr Ile Val Ile Leu Asp Ser Lys Val Asp Tyr
145                 150                 155                 160

Arg Gly Tyr Gln Cys Leu Asp Thr Phe Ile Lys Arg Asn Thr Pro Pro
                165                 170                 175

Gly Phe Gln Ala Ser Ser Phe Lys Thr Val Glu Val Asp Arg Lys Glu
            180                 185                 190

Gln Val Ala Leu Ile Met Asn Ser Ser Gly Ser Thr Gly Leu Pro Lys
        195                 200                 205

Gly Val Gln Leu Thr His Glu Asn Ile Val Thr Arg Phe Ser His Ala
    210                 215                 220

Arg Asp Pro Ile Tyr Gly Asn Gln Val Ser Pro Gly Thr Ala Val Leu
225                 230                 235                 240

Thr Val Val Pro Phe His His Gly Phe Gly Met Phe Thr Thr Leu Gly
            245                 250                 255

Tyr Leu Ile Cys Gly Phe Arg Val Val Met Leu Thr Lys Phe Asp Glu
            260                 265                 270

Glu Thr Phe Leu Lys Thr Leu Gln Asp Tyr Lys Cys Thr Ser Val Ile
        275                 280                 285

Leu Val Pro Thr Leu Phe Ala Ile Leu Asn Lys Ser Glu Leu Leu Asn
    290                 295                 300

Lys Tyr Asp Leu Ser Asn Leu Val Glu Ile Ala Ser Gly Gly Ala Pro
305                 310                 315                 320

Leu Ser Lys Glu Val Gly Glu Ala Val Ala Arg Arg Phe Asn Leu Pro
            325                 330                 335

Gly Val Arg Gln Gly Tyr Gly Leu Thr Glu Thr Thr Ser Ala Ile Ile
            340                 345                 350

Ile Thr Pro Glu Gly Asp Asp Lys Pro Gly Ala Ser Gly Lys Val Val
        355                 360                 365

Pro Leu Phe Lys Ala Lys Val Ile Asp Leu Asp Thr Lys Lys Ser Leu
    370                 375                 380
```

-continued

```
Gly Pro Asn Arg Arg Gly Glu Val Cys Val Lys Gly Pro Met Leu Met
385             390             395             400

Lys Gly Tyr Val Asn Asn Pro Glu Ala Thr Lys Glu Leu Ile Asp Glu
            405             410             415

Glu Gly Trp Leu His Thr Gly Asp Ile Gly Tyr Tyr Asp Glu Glu Lys
            420             425             430

His Phe Phe Ile Val Asp Arg Leu Lys Ser Leu Ile Lys Tyr Lys Gly
            435             440             445

Tyr Gln Val Ala Pro Ala Glu Leu Glu Ser Ile Leu Leu Gln His Pro
    450             455             460

Asn Ile Phe Asp Ala Gly Val Ala Gly Leu Pro Asp Asp Asp Ala Gly
465             470             475             480

Glu Leu Pro Ala Ala Val Val Val Leu Glu His Gly Lys Thr Met Thr
            485             490             495

Glu Lys Glu Ile Val Asp Tyr Val Ala Ser Gln Val Thr Thr Ala Lys
            500             505             510

Lys Leu Arg Gly Gly Val Val Phe Val Asp Glu Val Pro Lys Gly Leu
            515             520             525

Thr Gly Lys Leu Asp Ala Arg Lys Ile Arg Glu Ile Leu Ile Lys Ala
    530             535             540

Lys Lys Gly Gly Lys Ser Lys Leu
545             550
```

METHODS FOR SCREENING COMPOUNDS FOR BACTERICIDAL ACTIVITY AND FOR DETERMINING THE SENSITIVITY OF BACTERIAL SAMPLES

CROSS-REFERENCE TO RELATED APPLICATIONS

This application is a U.S. National Stage Application pursuant to 35 U.S.C. § 371 of International Patent Application PCT/EP2021/071592, filed on Aug. 2, 2021, and published as WO 2022/023582 on Feb. 3, 2022, which claims priority to European Patent Application 20305886.2, filed on Jul. 31, 2020, all of which are incorporated herein by reference in their entireties for all purposes.

REFERENCE TO SEQUENCE LISTING SUBMITTED ELECTRONICALLY

The Sequence Listing associated with this application is provided in ASCII format, and is hereby incorporated by reference into the specification. The name of the ASCII file containing the Sequence Listing is "Sequence Listing." The ASCII file is 8,192 bytes, was created on Sep. 17, 2025, and is being submitted electronically.

STATEMENT REGARDING SEQUENCE LISTING

Please enter into the application an initial Sequence Listing pursuant to 37 C.F.R. § 1.821. A computer readable form ("CRF") of the Sequence Listing in ASCII format in accordance with the requirements of 37 C.F.R. § 1.824 and the World Intellectual Property Organization ("WIPO") Standard ST.25 is submitted electronically.

FIELD OF THE INVENTION

The present invention relates to an easy, simple, reliable and very rapid method for screening compounds for bactericidal activity. The present invention also relates to a similarly easy, simple, reliable and very rapid method for determining the sensitivity of a bacterial sample originating from a subject suffering from a bacterial infection to a group of known antibiotics. Finally, the present invention relates to a rapid method for assessing the minimal inhibitory concentration (MIC) of a bactericidal compound.

BACKGROUND OF THE INVENTION

In antibacterial drug discovery and sensitivity testing, the ability of analyzing in real time huge libraries of compounds or solutions from drug producers is essential. Moreover, for the treatment of patients suffering from bacterial infections, rapid determination of the available bactericidal compounds to which the infection is sensitive and their appropriate minimal inhibitory concentration is also crucial to stop infection. In circumstances, such as pandemic of unprecedented bacterial infections, rapid screening for searching effective drugs is crucial.

However, current tests for screening new potential bactericidal compounds or testing susceptibility of a bacterial sample to known antibiotics are not satisfying. In particular, most of them are cumbersome and take many hours before a result is obtained. Most known assays can also only be performed using growing bacteria and not stationary phase or biofilm bacteria. In case of large numbers of patients to be tested, the antibiotic susceptibility test should be simple and provide a rapid and reliable answer.

For instance, Ling et al., (*Nature*. 2015 Jan. 22; 517 (7535):455-9) tested extracts from 10,000 bacterial isolates for their capacity to inhibit bacterial growth, by a method comprising a step requiring 20 hours of incubation. This growth inhibition assay also involves a lawn of growing bacteria on agar plates. Therefore, this assay is very slow and cannot be performed on cells at stationary phase of growth or inside a biofilm. Also, antibiotic susceptibility tests mostly rely on time-consuming growth inhibition assays of bacteria.

Adenosine-5'-triphosphate (ATP) is a key biological molecule and its quantitative detection is of prime importance and the subject of intense developments, in particular in the field of antibacterial drug discovery and sensitivity testing. Indeed, cell membrane destruction associated to cell lysis is characterized by the release of cellular ATP stocks. Therefore, some researchers proposed that it should be possible to measure bacterial cells' lysis by bactericidal compounds by measuring the amount of ATP released in the cells' culture medium.

This has been attempted by two groups. In the nineties, de Rautlin de la Roy et al (*J. Biolumin. Chemilumin.* 6, 193-201 (1991)) attempted to measure the kinetics of bactericidal activity of antibiotics using a luciferin-luciferase assay. In this test, the bactericidal effect of an antibiotic is only slowly detectable, sometimes only 10 hours after addition to the bacterial sample. Therefore, said test is not adapted to a rapid and efficient screening of new potential bactericidal compounds. Moreover, the bacteria were submitted to an osmotic shock when diluted into distilled water, which is expected to alter bacterial membranes, leading to non-antibiotic driven ATP release, thus skewing the results and rendering said test unreliable.

More recently, Heller et al., (2019. *PLoS ONE* 14(1): 1-13 (2019) disclosed a bacterial susceptibility test based on a method called ATP/OD600 ratio which involves the measurement of ATP released due to cell lysis by bioluminescence luciferin-luciferase reaction. In this method, the authors recommend adding the antibiotic only when the growth phase is almost finished and bacteria reach stationary phase. The use of stationary phase cells is due to the low sensitivity of the method. Waiting for stationary phase is time consuming and thus the duration of the proposed method is too long. Moreover, International guidelines on antibiotic susceptibility tests do not recommend to use stationary phase cells as some antibiotics such as aminoglycosides are poorly effective against these cells. The authors also recommend to adjust the measured variations in extracellular ATP concentration based on the optical density (OD) of the bacterial culture, which may alter the reliability of the test. Moreover, in this test, the tested samples are kept on ice for some time before measuring the bioluminescence, which step may induce a degradation of the ATP present in the test sample, which also alters the reliability and the sensitivity of the test. Indeed, the described method provided very weak signals and even failed for detecting the susceptibility of a sensitive bacteria to the aminoglycoside gentamicin. Furthermore, a step of centrifugation is used for removing the bacteria from the sample before measuring the ATP present in the test sample, which may lead to alteration of bacteria cell walls, further release of ATP, and thus artificially increase the measured sensibility of some bacteria to the screened compound. The proposed method is thus too long and not sufficiently sensitive and reliable.

International application WO 2019/162301 discloses an invention relating to a pharmaceutical composition comprising a first and a second peptide. The first peptide is a peptide of the bacteriocin PLNC8 αβ. It is also disclosed a method based on classical ATP efflux measurement to demonstrate cell lysis induced by PLNC8 αβ. This method uses a classical firefly luciferase, which is unstable at temperatures over 28° C. This instability alters the reliability and the sensitivity of the measurement test as illustrated by the absence of ATP release for concentrations of the peptide at the MIC or 2× the MIC.

The use of classical luciferase FLE-50 in ATP efflux measurement is also disclosed by Lennart NILSSON: ("*New Rapid Bioassay of Gentamicin Based on Luciferase Assay of Extracellular ATP in Bacterial Cultures*", ANTIMICRO-BIAL AGENTS AND CHEMOTHERAPY, vol. 14, no. 6, 1 Jan. 1978). As indicated above, this instability does not allow to obtain sensitive ATP measurement. In addition, the method disclosed by Nilsson does not allow to measure ATP efflux in real time. This method is thus not optimal since the low sensitivity and amplitude of the signal requires a minimum delay of 1 hour 30 minutes before any bioluminescence measurement.

From the above, it clearly appears that currently available methods for screening bactericidal drugs and for testing the bacterial sensitivity to known drugs are slow and show low sensitivity or reliability, and methods with improved rapidity, sensitivity and reliability are thus needed.

SUMMARY OF THE INVENTION

In the context of the present invention, the inventors developed methods that detect, in real time, the efflux of ATP or analogs thereof from live bacteria following exposure to new candidate bactericidal compounds or known antibiotics using the luciferin-luciferase assay. It should be note that the ATP or analogs efflux detected by the method of the invention is not necessarily the result of a cell lysis of entire bacteria or of a cell lysis with destruction of the bacterial cell wall, a phenomenon that is known for a few antibiotics such as beta-lactams. As explained above, ATP is a fragile biological molecule that hydrolyzes quickly. This instability can be significant in a culture medium where ATP hydrolases may be present. The use of real-time monitoring of the reaction of luciferase with ATP, as soon as it leaves the bacteria, avoids any degradation of ATP and thus allows maximum detection sensitivity and guarantees reliability of the measure. In addition, thanks to the use of real-time measurement, bacteria do not need to be subjected to physical (such as high-speed centrifugation) or chemical (such as osmotic shock) stress. They are merely grown to some minimal 600 nm optical density (OD600), luciferin-luciferase reagents and the new candidate bactericidal compound or known antibiotic are added, and bioluminescence is then measured in real-time (see FIG. 1), thus not skewing results by altering bacterial cell walls or changing the cell physiology because of media exchange (see FIG. 4, thus resulting in artificial release of ATP). The use of real-time measurement thus strongly improves sensitivity and reliability of the methods according to the invention, compared to prior art methods.

Moreover, real-time monitoring of the reaction of luciferase with ATP or analogs thereof also converted into light by luciferase allowed the inventors to discover, for the first time, time signatures and ATP leakage amplitudes characteristic for each family of antibiotics (see FIG. 8). Surprisingly, it has been found that ATP leakage is not necessarily the result of cell lysis, since the inventors showed that, at concentrations around the minimal inhibitory concentration (MIC), ATP leakage generally begins only a few minutes after contact with the antibiotic (see Table 2), even while the bacteria remain alive (see FIG. 8). This finding is the basis of methods that are much more rapid than prior art methods, a result being generally obtained after only a few minutes.

Furthermore, the inventors showed that the methods may be used for a wide range of antibiotics, either in purified form (see notably FIGS. 8, 10, 11) or as complex mixtures such as a bacterial supernatant (see FIG. 12), and also for a wide range of bacterial strains (for instance multi-drug resistant bacteria, see FIG. 20) and forms (such as planktonic cells or biofilms, see FIGS. 8, 20).

Overall, the method designed by the inventors is thus very rapid (generally a few minutes will be sufficient), sensitive (sub-MIC sensitivity) and reliable, and widely applicable (type of compounds/compositions and bacteria to be tested). The method may further be implemented into microplates, making it easily automatable and thus industrially useful. The method may also be implemented into microfluidic tools for ultra-high-throughput screening. The methods of the invention are thus suitable for testing large libraries of new candidate bactericidal compounds for drug discovery and for rapid antibiotic susceptibility tests in the context of bacterial resistance.

Finally, the inventors also showed that, using real-time monitoring of the reaction of luciferase with ATP or analogs thereof, it is possible to rapidly and reliably assess a compound minimal inhibitory concentration (MIC) on a given bacterial sample based on measure of the lag time between antibiotic compound addition and detection of ATP leakage at varying antibiotic concentrations (see FIGS. 22 and 23).

According to a first aspect, the present invention thus relates to a method for screening compounds for bactericidal activity, comprising:

a) providing one or more test bacterial sample(s) comprising live bacteria in a culture medium;

b) adding a mixture of luciferin and a thermostable luciferase to said test bacterial sample(s);

c) adding a candidate composition to said test bacterial sample(s); and d) incubating the test bacterial sample(s) to which the mixture of luciferin and thermostable luciferase and the candidate composition have been added at a temperature between 20 and 60° C., preferably between 35 and 37° C. and measuring bioluminescence in real-time;

wherein the optical density at 600 nm (OD600) of live bacteria in the test bacterial sample(s) after steps a), b) and c) have been performed is at least 0.0002, and wherein an increase of bioluminescence measured in a test bacterial sample in step d) is indicative that the candidate composition added to the test bacterial sample in step c) comprises at least one compound with bactericidal activity.

According to a second aspect, the present invention also relates to a method for determining the sensitivity of a bacterial sample originating from a subject suffering from a bacterial infection to a group of known antibiotics, comprising:

a) inoculating a bacterial sample originating from a subject suffering from a bacterial infection into a culture medium and, optionally, amplifying the bacteria in the sample;

b) dividing the bacterial sample of step a) into several sub-samples, with at least as many samples as the number of known antibiotics to be tested;

c) adding a mixture of luciferin and a thermostable luciferase to each sub-sample;

d) adding each of the group of known antibiotics or combinations of antibiotics to one or more sub-sample (s); and e) incubating the sub-sample(s) to which the mixture of luciferin and thermostable luciferase and the known antibiotic have been added at a temperature between 20 and 60° C., preferably between 35 and 37° C. and measuring bioluminescence in real-time;

wherein the optical density at 600 nm (OD600) of live bacteria in the sub-samples after steps a), b), c) and d) have been performed is at least 0.0002, and wherein an increase of bioluminescence measured in a sub-sample in step e) is indicative that the bacterial sample originating from a subject is sensitive to the added concentration of known antibiotic added to the sub-sample in step d).

According to a third aspect, the present invention also relates to a method for assessing the minimum inhibitory concentration (MIC) of a bactericidal compound comprising:

a) providing at least one test bacterial sample comprising live bacteria in a culture medium;

b) dividing the bacterial sample of step a) into several sub-samples, c) adding a mixture of luciferin and a thermostable luciferase to said sub-samples;

d) adding varying concentrations of a bactericidal compound to said sub-samples;

e) incubating the sub-samples to which the mixture of luciferin and thermostable luciferase and the bactericidal compound have been added at a temperature between 20 and 60° C., preferably between 35 and 37° C. and measuring bioluminescence in real-time, wherein the optical density at 600 nm (OD600) of live bacteria in the sub-samples after steps a), b), c) and d) have been performed is at least 0.0002 f) determining for each concentration of bactericidal compound tested the lag time between the time when said bactericidal compound has been added and the time of detection of an increase in the bioluminescence signal, g) representing the lag time in function of the bactericidal compound concentration, h) creating an exponential decay curve fitting the measured points of the lag time in function of the bactericidal compound concentration, i) determining the lowest bactericidal compound concentration in the plateau of the exponential decay fitting curve, j) determining the lag time amplitude of the exponential decay fitting curve, and k) assessing the MIC, wherein the MIC is assessed as comprised between:

the antibiotic concentration corresponding on the exponential decay fitting curve to or a lag time equal to (lag time at plateau+0.3× lag time amplitude), and the lowest bactericidal compound concentration in the plateau of the exponential decay fitting curve.

DESCRIPTION OF THE FIGURES

FIG. 1. Bioluminescence assay for real time monitoring of ATP release.

DETAILED DESCRIPTION OF THE INVENTION

Figure 2:
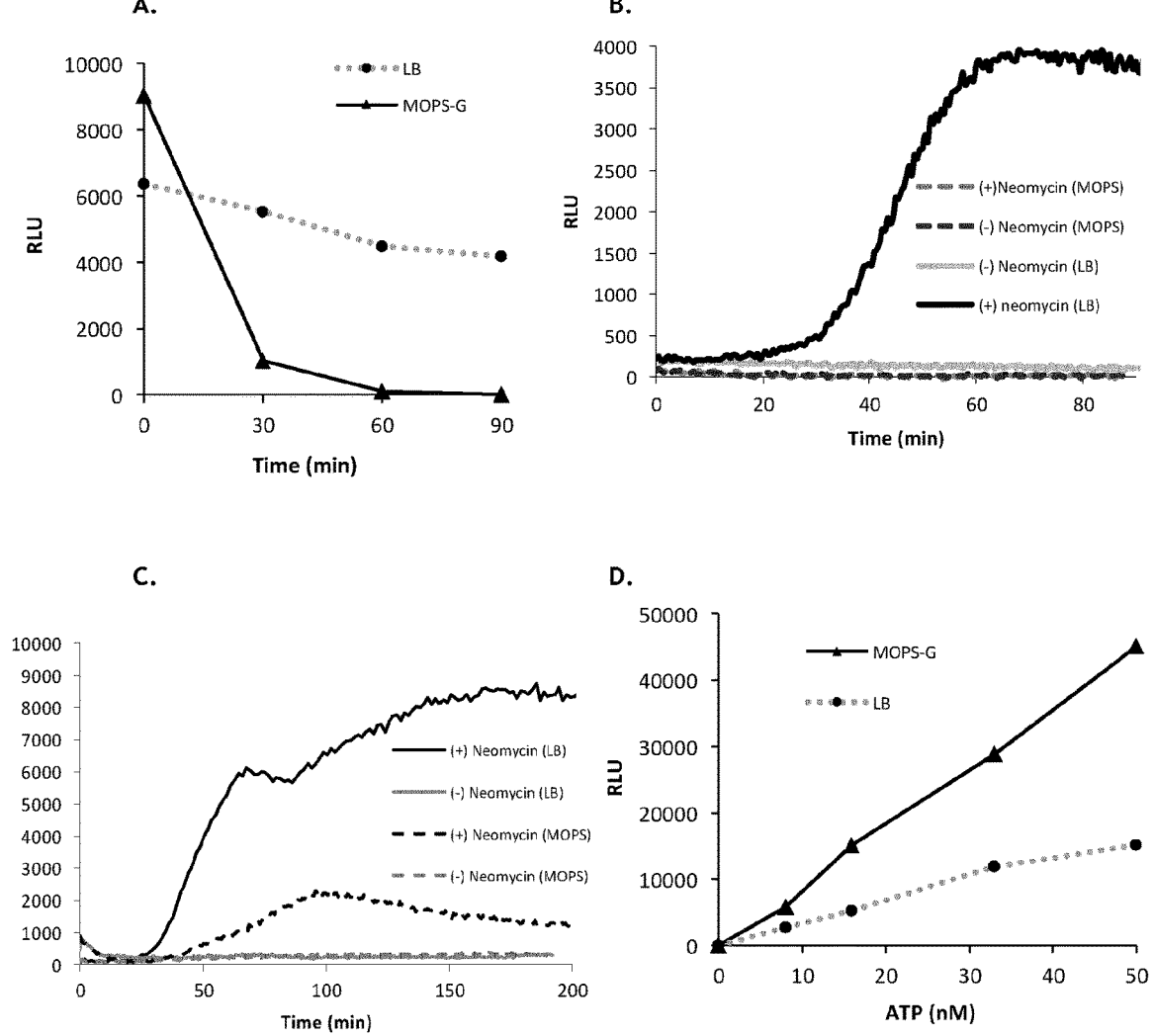
FIG. 2. Thermostable luciferase assay for real time monitoring of ATP efflux. A, Stability test of the classical luciferase assay. Signals of bioluminescence obtained following the addition of ATP after preincubating the reagents in rich (LB) or minimal (MOPS glucose 0.4%) media at 28° C. B, Response at 28° C. of the classical bioluminescence assay to an antibiotic (neomycin) known to trigger membrane damages. Neomycin was added to an exponential culture of *E. coli* MG1655 at its MIC: 22.8 µg/mL in LB and 0.8 µg/mL in MOPS glucose 0.4%. Controls without antibiotic in LB or in MOPS glucose 0.4% are included. C, Same experiment performed at 37° C. with a thermostable luciferase. D, Thermostable luciferase is better suited for ATP assay in minimal media. Bioluminescence signals obtained for a range of ATP concentrations in minimal medium or LB with the thermostable luciferase at 37° C.

As used herein, the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are open-ended and do not exclude additional, un-recited elements or method steps. The expression "consisting essentially of" means excluding other components or steps of any essential significance. Thus, a composition consisting essentially of the recited components would not exclude traces, contaminants and pharmaceutically acceptable carriers. "Consisting of" shall mean excluding more than trace elements of other components or steps. In the present description, each time the term "comprising" (or any of its derivatives such as "comprise" and "comprises") is used, the invention also relates to the same embodiment in which "comprising" (or any of its derivatives such as "comprise" and "comprises") is replaced by "consisting essentially of" or "consisting of".

Method for Screening Compounds for Bactericidal Activity (Screening Method)

As indicated above, the inventors developed methods that detect, in real time, the efflux of ATP or analogs thereof from live bacteria following exposure to new candidate bactericidal compounds or known antibiotics using the luciferin-luciferase assay. The methods of the invention are very rapid (generally a few minutes will be sufficient), sensitive and reliable (thanks to real time measurement—which prevents skewing due to fragile ATP decay, and because of absence of physical and chemical stressing of bacterial cells), and widely applicable (type of compositions and bacteria to be tested). It may further be implemented into microplates, making it easily automatable and thus industrially useful or to microfluidic tools for ultra-high-throughput screening. The method of the invention thus allows screening large libraries of new candidate bactericidal compounds.

According to first aspect, the present invention thus relates to a method for screening compounds for bactericidal activity, comprising:

a) providing one or more test bacterial sample(s) comprising live bacteria in a culture medium;

b) adding a mixture of luciferin and a thermostable luciferase to said test bacterial sample(s);

c) adding a candidate composition to said test bacterial sample(s); and d) incubating the test bacterial sample(s) to which the mixture of luciferin and thermostable luciferase and the candidate composition have been added at a temperature between 20 and 60° C., preferably between 35 and 37° C. and measuring bioluminescence in real-time;

wherein the optical density at 600 nm (OD600) of live bacteria in the test bacterial sample(s) after steps a), b) and c) have been performed is at least 0.0002, and wherein an increase of bioluminescence measured in a test bacterial sample in step d) is indicative that the candidate composition added to the test bacterial sample in step c) comprises at least one compound with bactericidal activity.

Step a): Providing at Least One Test Bacterial Sample Comprising Live Bacteria in a Culture Medium;

Optical Density of the Test Bacterial Sample

Figure 25:
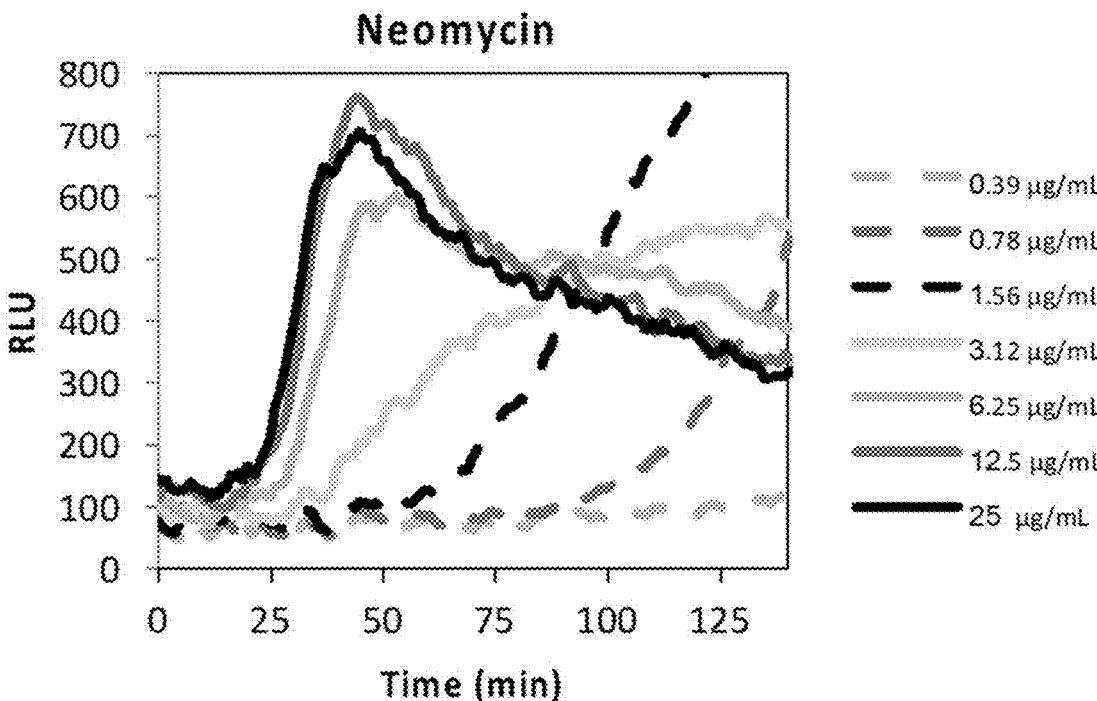
FIG. 25. Bioluminescence signal obtained with *E. coli* in clinical growth Mueller. A, Hinton media following the addition of neomycin. EUCAST recommendations were followed with an inoculum of D600 of 0.000275 (about 5.5×10^5 CFU/ml) bacteria colony-forming units per mL. B, Curves were smoothed using the moving average method. MIC estimation. Experimental MIC (3.12 μg/mL) is indicated by an open circle and X value at the MIC is given with its standard error of mean for four independent experiments. Bars represent the standard deviation (SD) calculated for the four independent experiments.
Figure 25:
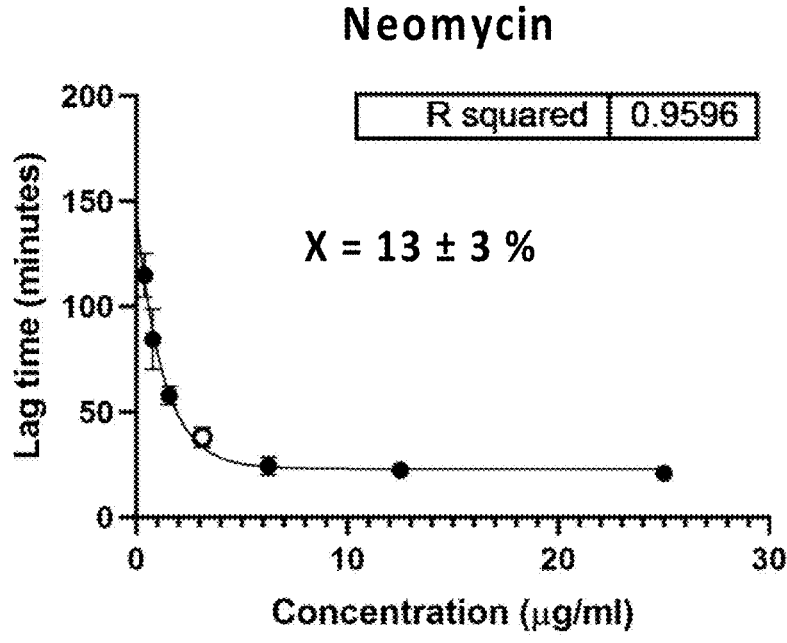

The inventors have shown that the amplitude of the ATP leakage signal is related to the amount of live bacteria (also called herein "reporter cells") in culture medium in the final sample (the test bacterial sample after steps a), b) and c) have been performed). For detection of ATP leakage, the bacteria have to be used at an optical density at 600 nm (OD600) of at least 0.0002, preferably at least 0.0003, at least 0.0005, at least 0.001, at least 0.005, at least 0.01, more preferably at least 0.015, even more preferably at least 0.1 in the final sample. Firstly, the inventors found, using black microplates, that while the signal of ATP leakage is acceptable at a final OD600 of 0.3 or 0.15, for a final OD600 of 0.015, the signal of ATP leakage is weak and the results are less reliable with such microplates and for a final OD600 of 0.0015 the signals of ATP leakage are extremely weak and cannot be used. Supplemental assays have been performed to improve the sensitivity of the screening method using white microplates (Greiner Bio-one, 655075) and the inventors found that even with a very low concentration of bacteria in the final sample, the signal of ATP leakage may be acceptable. The inventors thus found that at OD600 of at least 0.0002, preferably at least 0.0003, the signal of ATP leakage is detectable (FIG. 25). Thus, the OD600 of live bacteria in the test bacterial sample(s) after steps a), b) and c) have been performed is at least 0.0002, preferably at least 0.0003, at least 0.0005, at least 0.001, at least 0.005, at least 0.01, more preferably at least 0.015, preferably between 0.0002 and 0.5, between 0.0003 and 0.5, between 0.0005 and 0.5, between 0.001 and 0.5, between 0.005 and 0.5, between 0.01 and 0.5, between 0.015 and 0.5, between 0.03 and 0.5, between 0.05 and 0.5, or between 0.1 and 0.5. Moreover, since results obtained at a final OD600 of 0.3 or 0.15 are particularly satisfying, in accordance with preferred embodiment of the screening method of the invention, the OD600 of live bacteria in the final sample is comprised between 0.1 and 0.3, or between 0.1 and 0.2. Preferably, the OD600 of live bacteria in the final sample is 0.15.

The initial OD600 of live bacteria in the test bacterial sample of step a) (before steps b) and c) are performed) is thus higher than 0.03, preferably higher than 0.05, higher than 0.1, more preferably higher than 0.3. Preferably, the volumes of mixture of luciferin and thermostable luciferase added in step b) and of candidate composition added in step c) are such that the final volume (after steps b) and c)) is between 1.5 and 3 times, such as twice, the initial volume of the test bacterial sample. In this case, the initial OD600 of live bacteria in the test bacterial sample of step a) is thus 1.5 to 3 times (such as twice) higher than 0.0002, preferably higher than 0.0003, higher than 0.0005, higher than 0.001, higher than 0.005, higher than 0.01, higher than 0.015, more preferably 1.5 to 3 times (such as twice) higher than 0.05, 1.5 to 3 times (such as twice) higher than 0.1, even more preferably 1.5 to 3 times (such as twice) higher than 0.15. Depending on the necessary volumes added in steps b) and c) and the targeted final OD600 of live bacteria in the final sample incubated in step d), the skilled person will know which initial OD600 to choose for the initial test bacterial sample of step a). When the additions in steps b) and c) result in a final volume that is twice the initial volume of the test bacterial sample in step a), the initial OD600 of live bacteria in the test bacterial sample of step a) is preferably at least 0.0004, at least 0.0006, at least 0.001, at least 0.002, at least 0.01, at least 0.02, at least 0.03, at least 0.1, more preferably between 0.2 and 0.6 or between 0.2 and 0.4, most preferably about 0.3.

In the context of the present invention, the term "optical density at 600 nm (OD600)" relates to the measurement of bacterial growth by optical density at 600 nm. This measurement is based on absorbance detection mode and basically determines which portion of light passes through a sample of bacteria. Particles in solution scatter light and the more particles (bacteria) can be found in a solution, the more light is scattered by them. Therefore, a replicating population of bacteria increases light scattering and measured absorbance values. At the same time this means that the absorbance mode is only exploited to determine the extent of light scattering instead of measuring the physical absorbance of light energy by absorbing molecules. $OD_{600}$ thus measures light scattering and the $OD_{600}$ value can be directly related to the number of microorganisms.

Preferred Absence of Mechanical and/or Chemical Stress

Figure 4:
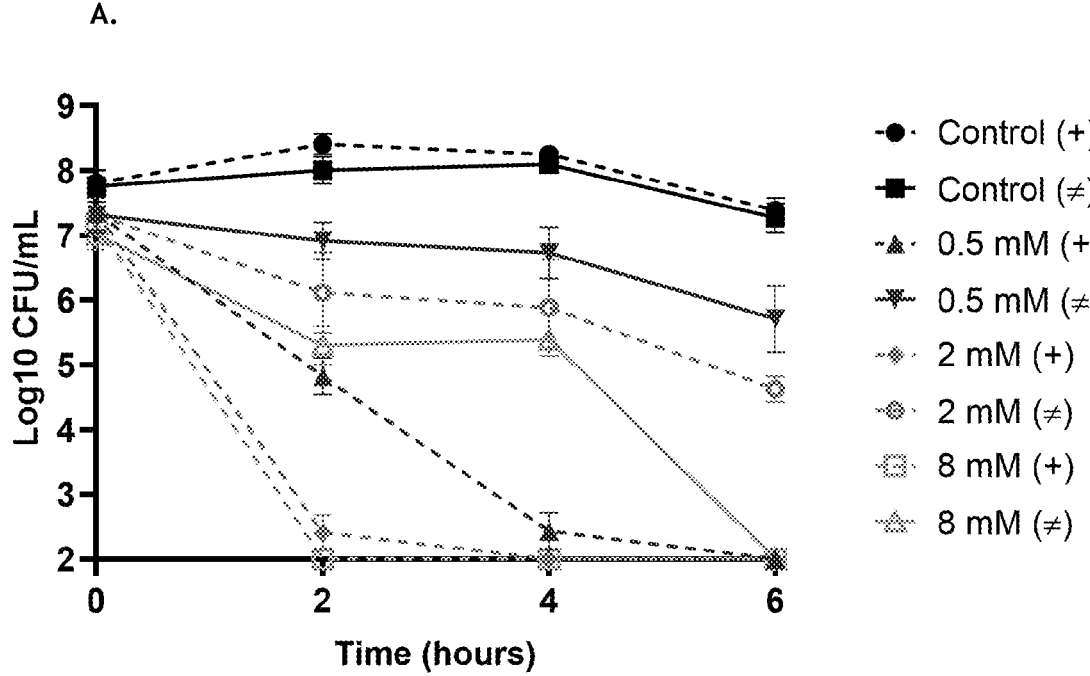
FIG. 4. A. Centrifugation with change for fresh medium prior to aminoglycoside exposure stimulates drug bactericidal effect. *S. aureus* USA300 in TSB medium with 0.25% glucose was incubated until stationary phase has been reached at 37° C. Cells were either centrifuged at 12 000 rpm for 5 minutes (+) or placed at 37° C. without centrifugation (≠). After centrifugation, pellets were washed with fresh broth and placed at 37° C. Depending on the test, different concentrations of neomycin were added. *S. aureus* USA300 samples that were centrifuged and washed with fresh broth are more sensitive to neomycin. For instance, bacterial CFU go below the detection threshold ($10^2$ CFU/ml) at 2 hours for 8 mM and 2 mM concentrations while it takes 2 more hours for the 0.5 mM concentration. Bars represent the standard error from the mean (SEM) calculated on GraphPad Prism version 8.4.1. B. *S. aureus* USA300 in TSB medium with 0.25% glucose was incubated until stationary phase has been reached at 37° C. Cells were either centrifuged at 12 000 rpm for 5 minutes or placed at 37° C. without centrifugation. After centrifugation, pellets were washed with fresh broth and placed at 37° C. A volume of 100 µL of fresh media with 4 mM of neomycin was added to all the tubes (final concentration at 2 mM), centrifuged or not, 5, 15, 30, 60 and 120 minutes post-centrifugation. Samples were incubated for a total of 2 hours with the neomycin before being washed three times with PBS 1×, diluted and incubated on tryptic soy agar. The next day, colony forming units/mL were counted. Bars represent the standard deviation (SD) calculated on GraphPad Prism version 8.4.3.

Furthermore, it is important to underline that the screening method of the invention preferably avoids manipulation of live bacteria. Particularly, said method preferably excludes any chemical or mechanical manipulation of the live bacteria which could disturb their physiology or damage them, i.e. any manipulation susceptible to induce a chemical or mechanical stress on the live bacteria in the sample. Mechanical and chemical stresses indeed damage the bacterial structure, in particular the bacterial membrane and its functions, just as do bactericidal compounds. The analysis of bacterial cells that have been previously submitted to chemical and/or mechanical stress thus skews the results, artificially increasing the measured sensitivity of the bacteria to antibiotic compounds (see FIG. 4).

Mechanical stress may be defined as a stress caused by physical manipulation of the live bacteria in the sample, for example, when transferring or storing the bacterial sample (for example, ice storage) or when submitting it to a centrifugation. It has notably been demonstrated that some strains, such as *Pseudomonas Aeruginosa* are sensitive to centrifugation (Gilbert et al., 1991, *Centrifugation injury of Gram-negative Bacteria*). Therefore, including steps inducing mechanical stress on bacteria used in a method for screening bactericidal compounds may be the cause of unreliable results.

Chemical stress is caused by addition in the culture medium of bacteria of a reagent in a concentration that alters the physiological balance between live bacteria and their environment, such as a sudden change in the solute concentration around the bacteria, causing a rapid change in the movement of water across its cell membrane (i.e. an osmotic shock). For instance, strongly diluting bacteria comprised in a culture medium into distilled water, as done in Rautlin de la Roy et al (*J. Biolumin. Chemilumin.* 6, 193-201 (1991)), results in an osmotic shock that may alter the bacterial structure, in particular the bacterial membrane and its functions, and thus artificially increase the measured sensitivity of the bacteria to antibiotic compounds.

Therefore, in accordance with one embodiment of the screening method, said living bacteria of the test sample provided in step a) have not been subjected to a mechanical or chemical stress, in particular less than 2 hours, preferably less than 4 hours and more preferably less than 6 hours before step a). In particular, said living bacteria of the test sample provided in step a) have preferably not been subjected to centrifugation or osmotic shock. More particularly, said living bacteria of the test sample provided in step a) have not been subjected to centrifugation or osmotic shock less than 2 hours, preferably less than 4 hours and more preferably less than 6 hours before step a).

In accordance with more preferable embodiment, the bacterial sample is not subjected to a mechanical or chemical stress during the screening method of the invention.

Type of Bacteria in the Bacterial Test Sample

As previously indicated, an advantage of the screening method of invention is that it allows to screen bactericidal compounds on a wide range of bacterial strains and growth states. According to one embodiment, the living bacteria in said test sample are selected from the group consisting of antibiotic resistant bacteria, including multidrug resistant bacteria; pathogenic bacteria; planktonic cells and bacteria cells in biofilms.

In the context of the present invention, the expression "antibiotic resistant bacteria" designates a bacterial strain which has developed the ability to defeat the bactericidal and/or the bacteriostatic effect of an antibiotic. As a result, the bacteria are not killed and continue to grow even in the presence of the bactericidal and/or bacteriostatic compound.

The antibiotic resistant bacteria may resist to one or more antibiotics. When bacteria resist to more than one antibiotic, they are designated as a "multidrug resistant bacteria".

In the context of the present invention, the term "pathogenic bacteria" designates all bacterial strains able to cause a damage and/or pathology to a living organism, particularly to an animal, more particularly to a mammal and even more particularly, to a human subject.

Moreover, as used herein, the term "planktonic cells" relates to free-flowing bacteria in suspension. Planktonic cells are opposed to "cells in biofilm", which may be defined as a structured community of bacterial cells enclosed in a self-produced polymeric matrix and adherent to an inert or living surface.

Some bacterial genera and in particular some bacterial strains are of particular medical interest, and may thus preferably be used in the screening method according to the invention. These include for instance the ESKAPE group of antibiotic-resistant "priority pathogens" as defined by the World Health Organization (WHO). ESKAPE is an acronym for designing Gram-positive and Gram-negative species: *Enterococcus faecium, Staphylococcus aureus, Klebsiella pneumoniae, Acinetobacter baumannii, Pseudomonas aeruginosa*, and *Enterobacter* species. WHO also published a catalogue of 12 families of bacteria that pose the greatest threat to human health. These include: *Helicobacter pylori* (clarithromycin-resistant), *Campylobacter* spp. (fluoroquinolone-resistant), Salmonellae (fluoroquinolone-resistant), *Neisseria gonorrhoeae* (cephalosporin-resistant, fluoroquinolone-resistant), *Streptococcus pneumoniae* (penicillin-non-susceptible), *Haemophilus influenzae* (ampicillin-resistant), *Shigella* spp. (fluoroquinolone-resistant). Also of interest are for instance Coagulase-negative staphylococci, *Mycobacterium tuberculosis*, many *Streptococcus* (such as *Streptococcus pneumoniae, Streptococcus pyogenes*) and *Pseudomonas* (such as *Pseudomonas aeruginosa*), *Enterococcus faecalis, Escherichia coli, Proteus mirabilis, Serratia marcescens, Citrobacter freundii*.

Other bacterial genera/strains are particularly easy to manipulate (for instance, because they are not pathogenic and do not require high security biocontainment) and may also preferably be used in the screening method according to the invention (once a new bactericidal compound has been identified with such bacteria, its bactericidal effect on other bacteria, pathogenic or not, may be confirmed). These include non-pathogenic strains of *Escherichia coli, Staphylococcus, Bacillus subtilis*, attenuated *Salmonella* strains.

Some bacteria are particularly sensitive to many antibiotics and may be of particular use in antibacterial screening such as for instance the Gram-positive strain *Micrococcus luteus*.

Culture Medium

As indicated above, in the test sample, live bacteria are in a culture medium.

While said culture medium should be able to sustain bacterial cells viability over the period of measurement, many distinct culture media may be used, and a person skilled in the art will know which media may be selected, depending on the type of bacterial reporter cells used in the screening methods.

In particular, when screening purified chemical compounds (see below), both rich media (such as Luria Broth (LB) or the cation-adjusted Muller-Hinton (MH)) and minimal media complemented with a source of carbon like glucose (such as MOPS-Glucose) may be used.

Figure 13:
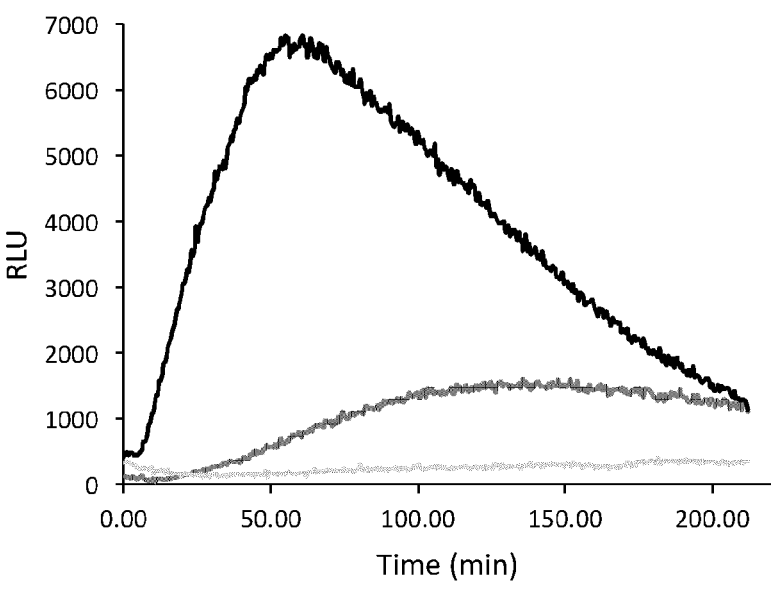
FIG. 13. False positive signal generated by rich medium. Black: Reporter bacterium *E. coli* incubated at 37° C. with luciferin-luciferase reagent solution and supernatant derived from *Streptomyces fradiae* culture (7 days). Grey: Supernatant incubated alone with fresh medium (to keep a constant volume) and luciferin-luciferase reagent solution (without bacteria). Light grey: Reporter bacterium *E. coli* incubated alone with fresh medium (to keep a constant volume) and luciferin-luciferase reagent solution (without supernatant). Bioluminescence was monitored during 210 min.
Figure 14:
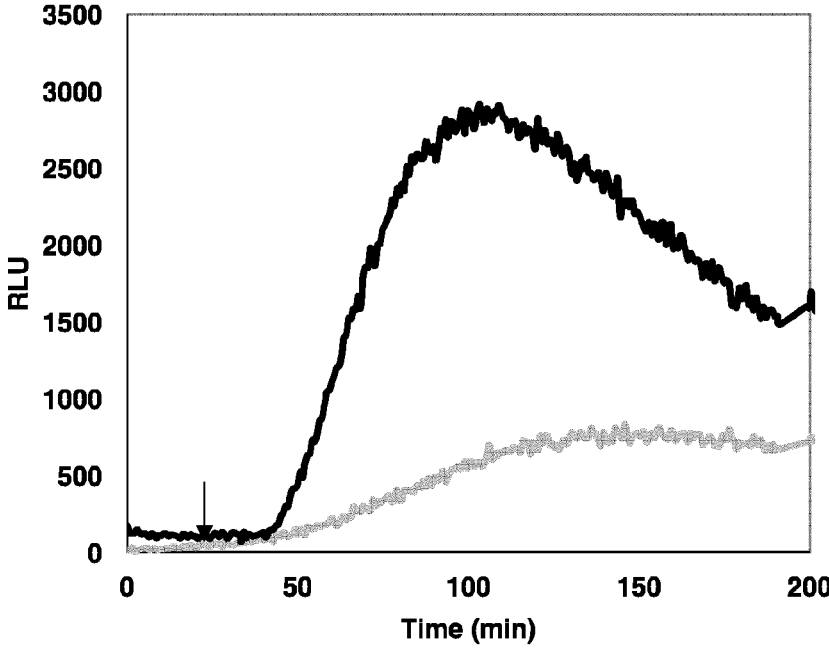
FIG. 14. Fresh LB medium when placed in contact with a supernatant from *Streptomyces fradiae* culture and with luciferase-luciferin reagents triggered bioluminescence. Addition of LB medium in supernatant derived from *Streptomyces fradiae* culture (7 days) generated a false-positive signal at 37° C. LB medium was injected after 30 min (black arrow). Light grey: ATCC strain. Black: DSM strain (Mutant DSM41550, which is a multi-mutated strain that cannot produce neomycin).
Figure 15:
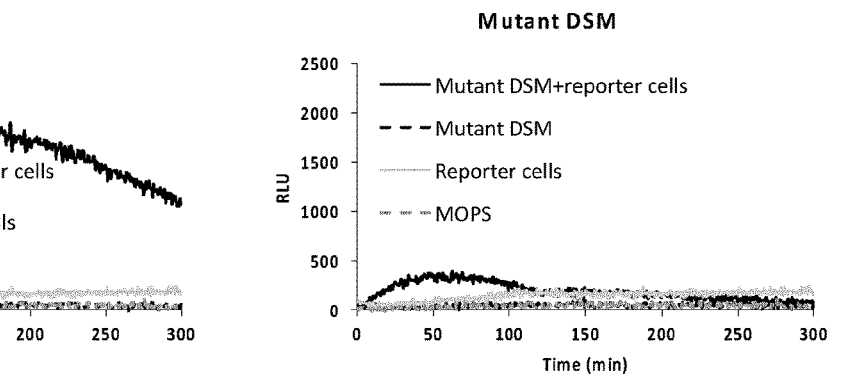
FIG. 15. Use of minimal medium resolved the issue of the false positive signal generated by rich media. Real-time monitoring of ATP leakage generated at 37° C. in MOPS-G medium by addition of supernatant from the neomycin producer *Streptomyces fradiae* (WT, left part of the figure). In these conditions, reporter cells (*E. coli*) or supernatant of WT *Streptomyces fradiae* cells when used alone did not produce a bioluminescence signal. Signal was only detected when reporter cells were placed in contact with the drug producer supernatant. In the case of the *Streptomyces fradiae* mutant strain DSM (Mutant DSM41550, right part of the figure), which is a multi-mutated strain that cannot produce neomycin, a very weak signal was observed suggesting the presence of some bactericidal compounds other than neomycin.

However, when screening complex mixtures such as bacterial supernatants, a minimal media complemented with a source of carbon like glucose (such as MOPS-Glucose) will preferably be used, because the inventors surprisingly found that the combination of a rich medium (such as Luria Broth (LB)) and of a bacterial supernatant induced bioluminescence production by luciferase from luciferin, even in the absence of bacteria reporter cells (see FIGS. 13 and 14), but that this effect was not observed when using a minimal media complemented with glucose (such as MOPS-Glucose, see FIG. 15).

In the context of the present invention, a "minimal medium" refers to a medium that contains the minimal necessities for growth of the bacteria of interest. It generally contains only inorganic salts, a carbon source, and water. Examples of minimal media that may be used in the invention when complemented with a source of carbon such as glucose, include MOPS and M9. MOPS medium contains a mixture of potassium morpholinopropanate sulphonate, hydro phosphates of potassium, water and thiamine, preferably adjusted to approximately pH 7, to which are added other components (Ferrous sulfate, ammonium chloride, potassium sulfate, calcium chloride, magnesium chloride, sodium chloride). A person skilled in the art will know how to prepare the medium. The minimal medium (MOPS) as described herein is also commercially available from Teknova, Inc. 2290 Bert Drive Hollister, CA 95023 USA .Teknova also proposes the same minimal medium that is enriched for repeatable high growth rate similar to that obtained in rich media such as LB.

When a minimal medium is used, it is preferably complemented with a source of carbon like glucose at a concentration comprised for glucose between 0.4 and 2%.

In the context of the present invention, a "rich medium" refers to a medium that allows the bacteria to grow at their maximum rate. It generally contains, in addition to component of a minimal medium, additional components, and in particular sodium chloride, complex nutrients (such as a mixture of peptides (tryptone) and yeast extract). Examples of rich media that may be used in the invention include Luria Broth (LB) (also referred to as Lysogeny broth (LB)), the cation-adjusted Muller-Hinton (MH). LB medium is a nutritionally rich medium primarily used for the growth of bacteria. While its composition may differ slightly depending on the provider, it always contains: peptides and casein peptones; vitamins (including B vitamins); trace elements (such as nitrogen, sulfur, magnesium) and minerals. According to preferred embodiment, for high reproducibility, the cation-adjusted Muller-Hinton (MH) medium is used. It contains adjusted levels of magnesium and calcium which are important component of the bacterial membranes. It is commercially available from Merck and contains beef extract, acid hydrolysate of casein and starch.

Step b): Adding a Mixture of Luciferin and a Thermostable Luciferase to Said Sample "Luciferase" is a generic term for the class of oxidative enzymes that produce bioluminescence. Luciferases do not require an external light source, but do require addition of luciferin as a substrate. The luciferase enzyme speeds up a chemical reaction that combines an oxygen molecule with luciferin to form oxyluciferin with concurrent emission of photons. This reaction requires energy provided by adenosine triphosphate (ATP) or specific analogues thereof (such as diadenosine tetraphosphate (Ap4A) which reacts weakly with luciferase and dehydroluciferine (Garrido et al., J.

Biochem. Biophys. Methods 30 (1995) 191-198)) and it releases light (bioluminescence). The bioluminescence is proportional to the concentration of ATP and ATP analogues hydrolysable by luciferase, which may thus be determined. Therefore, luciferase may be used to detect the level of cellular ATP and specific ATP analogues in cell viability assays or for kinase activity assays. Classically used firefly luciferase uses luciferin as a substrate which is oxidized to oxyluciferin in a reaction that utilizes molecular oxygen and ATP (or specific ATP analogues as mentioned above), and liberates light at 560 nm. Magnesium ions are also required in some cases (depending on the luciferase/luciferin specific pair used) for the reaction to occur. Since oxygen and magnesium ions are already present in the bacterial sample added in step a), only luciferase and luciferin need to be added in step b) for measuring ATP and ATP analogues leakage due to bactericidal compound.

In the context of the present invention, the inventors first evaluated the possibility to detect ATP or its analogues with a classically used firefly luciferase (Invitrogen Molecular Probes referenced as A22066) in rich and minimal media. Addition of ATP or its analogues to a rich medium (Luria Broth (LB)) or a minimal medium (MOPS complemented with glucose) containing the luciferin/luciferase reagents triggered luminesce. Firstly, the inventors determined that the stability of reagents was relatively high in rich LB medium and concluded that firefly luciferase might be used for detecting ATP signal. The assay was performed at 28° C. At the same temperature however, in minimal MOPS medium complemented with glucose, reagents were rapidly inactivated and obtained ATP signals were unstable and thus, difficult to detect. To determine if a classically used firefly luciferase permits sensitive and reliable measure of ATP at temperature usually used for growing bacteria, the inventors performed supplemental assays in rich and in minimal culture media at 37° C. The results shown on FIG. 24 demonstrate that at 37° C. it is not optimal to obtain a reliable and sensitive ATP detection in minimal and in rich culture media with classical firefly luciferase. The inventors surprisingly found that this issue does not occur with a thermostable luciferase. Consequently, the screening method of the invention uses a thermostable luciferase which is added to the sample provided in step a) of the method.

In the context of the present invention, the term "thermostable luciferase" relates to a luciferase enzyme, particularly a firefly luciferase, with improved stability at a temperature over 30° C. In particular, a thermostable luciferase preferably has improved activity at a temperature over 30° C., in particular at 37° C., compared to a conventional luciferase, in particular compared to wild-type firefly luciferase of *Photinus pyralis* as disclosed in Genbank release 243 with accession number AAA29795.1. Improved thermostability of luciferase may be obtained by insertion of various mutations in the amino acid sequence of luciferase or generating chimeric forms by combining sequences of various luciferases. For instance, a thermostable luciferase of Kikkoman was generated by gene chimerization between *Photinus pyralis* luciferase and a thermostable variant of *Luciola cruciata* luciferase in combination with mutations to improve catalytic performance (Hirokawa et al., Biochimica et Biophysica Acta 1597 (2002) 271-279). Several types of mutant luciferase with improved stability have been disclosed (see for instance EP0524448, U.S. Pat. Nos. 5,229,285A and 6,074,859 all from Kikkoman Co., NanoLuc® (NLuc) from Promega (Hall et al., ACS Chem Biol. 2012 Nov. 16; 7(11):1848-57. doi: 10.1021/cb3002478; England et al., Bioconjug Chem. 2016 May 18; 27(5): 1175-1187. doi:10.1021/acs.bioconjchem.6b00112.)), and may be used in the screening method of the invention.

According to one embodiment of the screening method of the invention, the thermostable luciferase is selected from the group consisting of: a thermostable firefly luciferase from Kikkoman Co. (such as those disclosed in EP0524448A1 or U.S. Pat. No. 5,229,285, including the thermostable firefly luciferase of the CheckLite AT100 kit) or the luciferase Nanoluc (also referred to as "Nluc") from Promega (see Hall M P, Unch J, Binkowski B F, et al.. Engineered luciferase reporter from a deep sea shrimp utilizing a novel imidazopyrazinone substrate. ACS Chem Biol. 2012; 7(11):1848-1857. doi:10.1021/cb3002478, sequence of Nanoluc is disclosed in Figure S6 and having accession number in GenBank release 243 n° AF179290) or any other luciferase that is thermostable in the medium used for screening. Particularly, the activity of the luciferase in the medium used for screening is tested. Preferably, the thermostable luciferase is a thermostable firefly luciferase from Kikkoman Co. (such as those disclosed in EP0524448A1, U.S. Pat. No. 5,229,285A or U.S. Pat. No. 6,074,859, including the thermostable firefly luciferase of the CheckLite AT100 kit, corresponding to SEQ ID NO:7 of U.S. Pat. No. 6,074,859 (having accession number in GenBank release 243 n° AAE43251.1) with the additional T219I and V239I substitutions) or the engineered luciferase Nano-Luc® from Promega.

In the screening method of the invention, the thermostability of luciferase advantageously allows to perform the test in several types of media, prevents degradation of the luciferase for monitoring the reaction over long periods and facilitates handling of the enzyme during preparation. "Luciferin" is used herein as a generic term for the compounds found in organisms that generate bioluminescence that emit light after oxidation by luciferase.

Luciferins typically undergo an enzyme-catalyzed oxidation and the resulting excited state intermediate emits light upon decaying to its ground state. Luciferins are thus small-molecule substrates for luciferase enzymes. There are various types of luciferins (including D-luciferin and derivatives thereof such as CycLuc1 and AkaLumine-HCl; coelentarazin and derivatives thereof such as diphenylterazine and selenoterazine; furimazine) and derivatives/analogues thereof (e.g. D-luciferin derivatives/analogues: CycLuc1 and AkaLumine-HCl; coelentarazin derivatives/analogues: diphenylterazine and selenoterazine). Luciferin derivatives/analogues may also be used. In particular, luciferin analogs have been generated that react with luciferase mutant to emit light at wavelength other than 560 nm such as 599, 607, 675 and 706 nm (Jathoul et al., Angew Chem Int Ed Engl. 2014 Nov. 24; 53(48):13059-63. doi: 10.1002/anie.201405955.) The analogue AkaLumine-HCl produces bioluminescence in the near-infrared wavelength ranges (677 nm) (Kuchimaru et al., Nat Commun. 2016 Jun. 14; 7:11856. doi: 10.1038/ncomms11856.). Other novel Luciferins when combined with engineered luciferase also produce light at 460 nm (Hall et al., ACS Chem Biol. 2012 Nov. 16; 7(11):1848-57. doi: 10.1021/cb3002478) or 677 nm (Yeh et al., Nat Methods. 2017 October; 14(10):971-974. doi: 10.1038/nmeth.4400.) Therefore, various type of luciferin/luciferase reactions may be used but these reactions always require the presence of molecular oxygen and ATP or analogues thereof. Examples of luciferin that may be used in the invention include any luciferin analog in luciferin-luciferase pair providing the luciferase is thermostable. Examples of pairs such as the furimazine-Nanoluc can be found in Table 1 in Yeh et al., Nat Methods. 2017 October; 14(10):971-974. doi: 10.1038/nmeth.4400.

The combination of luciferin and thermostable luciferase used in the screening method of the invention is selected so that the selected luciferin is an appropriate or even optimized substrate for the selected thermostable luciferase. Examples of appropriate (luciferin/thermostable luciferase) combinations include (firefly luciferin/thermostable firefly luciferase), the furimazine-Nluc luciferase, furimazine-Antares luciferase, the diphenylterazine (DTZ)-teLuc, the diphenylterazine (DTZ)-Antares2, the selenoterazine (STZ)-yeLuc.

Kits comprising a solution comprising a mixture of luciferin and thermostable luciferase in appropriate ratios are available in the art. Examples of such kits include the CheckLite AT100 kit available from Kikkoman, the Nanoluc from Promega.

The luciferin and luciferase concentrations or the corresponding factor of dilution of stock luciferin and luciferase solutions added in step b) will be adapted by skilled artisan so that the final concentrations, after the candidate composition has further been added in step c), correspond either to the recommended final luciferin and luciferase concentrations in the instructions provided with a selected commercial luciferin/luciferase kit or based on preliminary determination of optimal concentrations of the selected luciferin/luciferase using conventional methods known in the art for this purpose.

In the preferred embodiment of the screening method of the invention (as described in the examples) where the thermostable luciferase kit "CheckLite AT100" (Kikkoman) or NanoLuc® (NLuc) is used, the mixture of luciferin and luciferase after steps a) to c) have been performed (in the final sample containing all reagents) is preferably diluted 6 to 9 times compared to the initial stock solution prepared according to the art and manufacturer guidelines from the Kikkoman kit.

Step c): Adding a Candidate Composition to Said at Least One Sample

After step b), wherein a mixture of luciferin/thermostable luciferase is added to the sample comprising the live bacteria in culture medium, a candidate composition (containing at least one compound screened for bactericidal effect) is added in step c).

The method of the invention allows to screen several types of candidate compositions having different structures and origins.

According to one embodiment of the screening method of the invention, the candidate composition is a purified compound. This purified compound may be a chemical or a biological compound.

In the context of the present invention, the term "purified compound" relates to a compound obtained by physical separation of a chemical substance of interest from foreign or contaminating substances. The purified compound screened by the method of the invention may be obtained by any one of known purification methods. A purified compound represents at least 90% w/w, preferably at least 95% w/w, at least 96% w/w, at least 97% w/w, at least 98% w/w, or at least 99% w/w of the candidate composition.

As used herein, the term "chemical compound" designs any substance consisting of two or more different types of atoms (chemical elements) in a fixed stoichiometric proportion. The chemical compounds screened by the method of the invention may have a natural origin, i.e may exist in the nature as such or may be artificial, obtained by chemical synthesis.

As used herein, the term "biological compound" designs an organic compound, i.e a compound that contains carbon. The biological compound may be obtained from living organisms or may be synthetized by chemical synthesis. In preferred embodiment of the method of the invention, the biological compound contained in the candidate composition may be selected from DNA (any type of DNA, including single-stranded DNA, double-stranded DNA, hairpin DNA, linear or circular DNA . . . ), RNA (any type of RNA, including mRNA, miRNA, siRNA, single-stranded RNA, double-stranded RNA, hairpin RNA . . . ), proteins (including enzymes, antibodies, toxins . . . ), peptides, hormones, metabolites, microorganisms (including viruses, and more particularly phages). In a preferred embodiment of the method of the invention, the biological compound contained in the candidate composition is a phage. Herein, the term "phage" or "bacteriophage" relates to a virus that infects and replicates within bacteria.

According to another embodiment, the candidate composition added in step c) of the method of the invention is a complex mixture, preferably bacterial supernatant or extract.

In the context of the present invention, the term "bacterial supernatant" relates to the liquid overlying the solid bacterial material deposited by settling, precipitation or centrifugation of a bacterial culture. A bacterial supernatant thus contains, in addition to the culture medium, products secreted by the cultured bacteria. Furthermore, the term "bacterial extract" relates to the product obtained by the extraction of one or more bacterial components (including proteins, lipids, metabolites and/or sugars) from a bacterial culture. Preferably, when a bacterial extract is used in the screening method of the invention, ATP that might be present in the extract is hydrolyzed before starting the screening. This inactivation may be performed in different manners known in the art. For example, ATP may be inactivated by heating the bacterial sample at a temperature between 37 and 50° C. A skilled artisan would be able to determine the heating temperature so that to inactivate ATP without altering other compounds of the bacterial extract tested in the following measurement. Another method for inactivating ATP present in the sample before adding the screened compound involves the use of enzymes able to digest ATP. Example of such enzymes is ATPase (transforming ATP to ADP (adenosine diphosphate) which is transformed in AMP (adenosine monophosphate) and adenosine monophosphate deaminase (which remove the amino group). Generally, after the digestion of ATP by the enzymes, these ones should be removed from the tested sample in order to avoid digesting ATP released after adding the screened compound. For this purpose, a surfactant as those used in Kikkoman Co. kit disclosed above may be used. These enzymes may be also removed by filtration. Any conventional method of protein filtration may be used. Particularly, an ultrafiltration device (VivaSpin™ 500 GE HealthCare) may be used as those used in the present invention for the filtration of supernatant.

In an embodiment of the method of the present invention, the candidate composition is filtered before its addition in step c), preferably using a membrane with a cut-off of at most 15000 daltons, preferably comprised between 2000 and 15000 daltons, between 3000 and 10000 daltons, between 4000 and 8000 daltons, such as 5000 daltons. Such filtration step is particularly useful when the candidate composition is a complex mixture, such as a bacterial supernatant or a bacterial extract. Indeed, the inventors have shown that large molecules present in bacterial supernatant interfere with the reaction by which luciferase converts ATP or analogues thereof to bioluminescence and that previous filtration of the bacterial supernatant with a membrane with a cut-off of 5000 Da restores an optimal conversion of ATP or analogues thereof to bioluminescence by luciferase (see FIG. 19b). Therefore, when the candidate composition is a complex composition such as a bacterial supernatant or a bacterial extract, it is preferably filtered with a membrane with a cut-off of at most 15000 daltons, preferably comprised between 2000 and 15000 daltons, between 3000 and 10000 daltons, between 4000 and 8000 daltons, such as 5000 daltons before its addition in step c).

In any case, the candidate composition is preferably added at a concentration that may be expected to result in ATP leakage if the candidate composition contains at least one bactericidal compound.

Compounds considered as bactericidal compounds generally have a MIC of at least 0.002 µg/mL and at most 1024 µg/mL. Therefore, the candidate composition (in particular when it comprises a purified chemical compound) will preferably be added in step c) at a concentration resulting in a final concentration in step d) (after addition to the test bacterial sample of both the mixture of luciferin and thermostable luciferase and of the candidate composition) of at least 0.002 µg/mL, preferably the concentration of the candidate composition at the beginning of step d) is between 0.002 µg/mL and 1024 µg/mL.

Preferably, taking into account the preferred concentrations disclosed above for live bacteria, luciferin, luciferase and candidate composition, after steps a), b) and c) have been performed:

The OD600 of live bacteria is at least 0.1, preferably it is comprised between 0.1 and 0.3, more preferably between 0.1 and 0.2, in particular it is 0.15.

The solution of luciferin is diluted to an optimized concentration, which will be selected either based on the luciferin manufacturer recommendations or based on preliminary test experiments (between 6 and 9 times when the "CheckLite AT100" kit of Kikkoman or NanoLuc® (NLuc) is used);

The solution of thermostable luciferase is diluted to an optimized concentration, which will be selected either based on the luciferin manufacturer recommendations or based on preliminary test experiments (between 6 and 9 times when the "CheckLite AT100" kit of Kikkoman or NanoLuc® (NLuc) is used) and/or The concentration of candidate composition is at least 0.002 µg/mL, preferably between 0.002 µg/mL and 1024 µg/mL.

Step d): Incubating the Sample at a Temperature Between 20 and 60° C., Preferably Between 35 and 37° C. and Measuring Bioluminescence in Real-Time (Measure Step)

After steps b) and c), the sample is then incubated during step d) at a temperature between 20 and 60° C. (temperature to choose in agreement with the luciferase thermostability parameter), preferably between 30 and 40° C. and more preferably between 35 and 37° C. Such conditions are indeed appropriate to maintain the bacteria of the sample alive in the absence of a bactericidal compound. This way, only ATP leakage due to the presence of a bactericidal compound in the candidate composition is detected. While these temperature conditions are considered being optimal for thermostable luciferases used according to the preferred embodiment of the screening method of the invention, the temperature may be adapted in agreement with each luciferase thermostability parameters.

During this step, the bioluminescence is measured in real time. The detection of an increase in measured bioluminescence is indicative that the candidate composition added to the sample in step c) comprises at least one compound with bactericidal activity.

The bioluminescence may be measured in real time by any means known to the skilled artisan for performing such measurement. Particularly, the bioluminescence may be measured by means selected from the group of instruments called luminometers such as for a few examples: single tube luminometers (Luminescencer Octa, ATTO, Lumat 3, Berthold Technologies, Sirius L, TiterTek Berthold . . . ), multi-tube luminometers (AutoLumat LB 953, Berthold Technologies), Luminometer for real time culture (Kronos Dio, ATTO), High throughput screening system (FDSS7000EX, Hamamatsu), particularly by a microtiter plate reader (for example: InfinitePro200, TECAN, FDSS/RayCatcher, Hamamatsu, Plate Chameleon V, Hidex, Synergy H1, BioTec).

As used herein, "measuring in real time" means that several measurements of the same sample are performed during a predetermined period of time (measurement period) in order to provide a recording of the change of the signal as a function of time with the sufficient temporal resolution. This period of time may last from 20 min to 180 min, preferably from 20 min to 60 min and more preferably, from 15 min to 40 min. Depending on the duration of the measurement period, each individual sample may be measured 20 to 200 times, more preferably 20 to 75 times and more preferably 15 to 50 times. As indicated above, the main advantage of the screening method of the invention is that the measurement is performed in real time (i.e. more than one measurement of the sample may be performed during a short period of time, which allows to obtain a maximum detection sensitivity, a recording of the change of the signal as a function of time with the sufficient temporal resolution and guarantees reliability of the measure). One measurement can be comprised between 0.5 and 5 s, particularly between 1 and 3 s and more particularly between 1 and 2 s. The time interval between two measurements of the same individual sample may be comprised between 1 s and 100 s, particularly, between 1 s and 90 s and more particularly, between 10 s and 80 s or between 10 s and 60 s. When using a microplate comprising several individual samples and a measuring device that measures all microplate wells one after another (rather than all simultaneously), the time interval between two measures of the same individual sample will depend on the total number of samples to be measured. However, taking into account that the duration of a single measure and move to the next sample cannot be lower than 0.2 second on a Tecan Infinite M200 Pro plate reader, the time interval between two measures of the same individual sample should not be lower than 20 seconds for a complete 96 wells microplate or 30 seconds for a 384 wells microplate. Based on these data, the skilled artisan would be able to calculate the time interval between two measures of the same individual sample if other kind of plate reader is used.

According to one embodiment, between two measurements of all samples, the measured samples are submitted to a gentle agitation in order to homogenize their content. The parameters of agitation may be determined by the skilled artisan based on his general knowledge and/or after performing some conventional tests. Particularly, among the agitation parameters, it is necessary to determine the mode of shaking, the amplitude and the frequency.

According to one embodiment, when samples are in a microplate, the mode of shaking may be selected from orbital or linear shaking, transversal shaking or X-Y axis shaking. The amplitude of agitation may be comprised between 0.1 mm and 10 mm, preferably between 1 mm and 5 mm and more preferably, about 3 mm. The frequency may be selected from 50 rpm to 500 rpm, preferably from 100 rpm to 300 rpm and more preferably from 200 rpm to 250 rpm.

In a preferred embodiment of the screening method, when samples are in a microplate, the agitation is performed with the following parameters: mode of shaking: orbital, amplitude: 3 mm and frequency: 218.3 rpm.

Since the inventors have shown that leakage of ATP or analogs thereof may start within a few minutes in the presence of a sufficient concentration of a bactericidal compound, step d) preferably starts as soon as step c) is done, i.e. as soon as a candidate composition (or culture medium or a known bactericidal compound for some negative and positive controls, respectively) has been added to the mixture of a bacterial sample, luciferin and thermostable luciferase.

As appears from above, the screening method according to the invention only involves providing a bacterial sample (step a)), adding further components (steps b) and c)), and measuring bioluminescence in real time during incubation of the final sample in step d). The method thus does not necessitate any handling of the bacterial sample that might induce chemical (no harsh dilution in water) or mechanical (no centrifugation) stress to the bacterial sample or any waiting step that might degrade ATP or analogues thereof. This makes the screening method of the invention more rapid, more sensitive and more reliable.

Order of the Steps

Step a) is performed first.

Steps b) and c) are performed after step a) and before step d). However, provided that they are performed between steps a) and d), steps b) and c) may be performed in any order: step b) before step c), step c) before step b), or both steps b) and c) simultaneously (if the mixture of luciferin and thermostable luciferase and the candidate composition have been mixed beforehand).

According to a preferred embodiment of the method of the invention, step c) is performed after or simultaneously with step b) in order to improve the real time measurement of ATP efflux. Indeed, when step c) is performed before step b), the ATP efflux may start before luciferase/luciferin are added and consequently the initial phase of ATP leakage might be missed. More preferably, step c) is performed after step b), preferably between 2 and 15 minutes after step b), more preferably between 3 and 10 minutes after step b) and even more preferably between 4 and 6 minutes after step b) and particularly about 5 minutes after step b). This delay between steps b) and c) allows the luciferase/luciferin mixture to consume traces of ATP that can be present in the culture of bacteria that might otherwise affect the initial reading of the bioluminescence signal during step d).

If step c) is nevertheless performed before step b), then step b) should be performed as soon as possible after step c), such as less than 1 minute, preferably less than 30 seconds after step c).

Negative and Positive Controls

In order to improve the reliability of the screening method, said screening method preferably also measures bioluminescence in real time in negative and/or positive control samples. In particular, for a set of screening samples comprising at the end of step c) a test bacterial sample, a mixture of luciferin and a thermostable luciferase, and a candidate composition, the method preferably also measures bioluminescence in real time in:

at least one negative control sample comprising a test bacterial sample, a mixture of luciferin and a thermostable luciferase, but without a candidate composition or a known bactericidal composition, and/or at least one positive control sample, comprising a test bacterial sample, a mixture of luciferin and a thermostable luciferase, and a known bactericidal composition.

Since the negative control sample is supposed to contain no compound with bactericidal effect, an absence of bioluminescence measurement in negative control sample is expected and confirms that the experiment was reliable, and that an increase of bioluminescence measured in any screening sample containing the candidate composition indeed indicates the presence of at least one bactericidal compound in the candidate composition and is not a false positive result.

Positive control sample is supposed to contain a compound with known bactericidal effect or ATP, so that an increase of bioluminescence in said positive control sample is expected and confirms that the experiment was reliable and that an absence of increase of bioluminescence measured in a screening sample containing the candidate composition indeed indicates the absence of at least one bactericidal compound in the candidate composition and is not a false negative result. Moreover, when an increase of bioluminescence is measured both in a positive control sample and in a screening sample, the comparison of the bioluminescence measured in both samples gives an idea of the bactericidal power of the candidate composition at the tested concentration.

Implementation of the Screening Method in a Microplate

In a preferred embodiment, the screening method of the invention is performed in a microplate. Using a microplate is particularly practical and makes the method easily automatable, since many devices able to simultaneously add further components to the wells of a microplate and microplate bioluminescence readers are available to those skilled in the art.

In this embodiment, the microplate may be any microplate classically used in screening methods. Particularly, the microplate may be manufactured in plastic or polystyrene. Moreover, the microplate may be colored white by the addition of titanium dioxide for improving the luminescence detection. According to a preferred embodiment, the microplate is not black or dark, more preferably, the microplate is of light color (such as light gray, ivory, light beige, etc.) and even more preferably, the microplate is white. Using microplates of light color (preferably white) make them reflect light, while dark colors (such as black) absorb some of the emitted light, thus explaining the observed difference in sensitivity based on the final OD600 of bacteria in the test sample.

The microplate used in the screening method of the invention may have varying numbers of wells, depending on the number of candidate compositions to be screened, such as 6, 12, 24, 48, 96, 384 or 1536 wells. Said wells may have a flat, round or V bottom. The total (up to the top of the well) and recommended working (maximum volume recommended by manufacturer to prevent spilling out and well to well contamination) volumes of each well will vary depending on the number of wells in the microplate. In particular, 96 well microplates generally have a recommended working volume comprised between 25 µL and 200 µL, while 384 well microplates generally have a recommended working volume comprised between 5 µL and 80 µL.

In most instances, many candidate compositions are to be screened, and preferred microplates for use in the screening method of the invention thus have a high number of wells, such as 96 or 384 wells, with a recommended working volume/well of 25 µL and 200 µL and 5 µL and 80 µL respectively.

Preferably, at the end of step c), the microplate comprises i) at least one screening well comprising a test bacterial sample, a mixture of luciferin and a thermostable luciferase, and a candidate composition, and:

ii) at least one negative control well comprising a test bacterial sample, a mixture of luciferin and a thermostable luciferase, but without a candidate composition or a known bactericidal composition, and/or iii) at least one positive control well, comprising a test bacterial sample, a mixture of luciferin and a thermostable luciferase, and a known bactericidal composition or ATP.

Preferably, the microplate comprises at the end of step c) at least one screening well i) as defined above, at least one negative control well ii) as defined above, and at least one positive control well iii) as defined above. The microplate may also contain several wells with the same components. In particular, the same candidate composition may be added to several distinct wells comprising a bacterial sample and a mixture of luciferin and thermostable luciferase, in order to test the bactericidal effect of the candidate composition at various concentrations and/or to reproduce the measure (duplicates or triplicates) at the same concentration in order to improve reliability of the results.

According to another embodiment, the screening method of the invention may also be implemented into microfluidic tools for ultra-high-throughput screening.

Method for Determining the Sensitivity of a Bacterial Sample Originating from a Subject Suffering from a Bacterial Infection to a Group of Known Antibiotics (Antibiotic Sensitivity Determination Method)

Based on the principle of the screening method of the invention, the inventors also developed a method for determining in real time the sensitivity of a bacterial sample originating from a subject suffering from a bacterial infection to a group of known antibiotics. The purpose of this method is to rapidly determine in clinical condition the antibiotic(s) showing efficient bactericidal effect on the pathogenic bacteria in the tested sample.

In accordance with the second aspect, the present invention thus relates to a method for determining the sensitivity of a bacterial sample originating from a subject suffering from a bacterial infection to a group of known antibiotics, comprising:

a) inoculating a bacterial sample originating from a subject suffering from a bacterial infection into a culture medium and, optionally, amplifying the bacteria in the sample;

b) dividing the bacterial sample of step a) into several sub-samples, with at least as many samples as the number of known antibiotics to be tested;

c) adding a mixture of luciferin and a thermostable luciferase to each sub-sample;

d) adding each of the group of known antibiotics to one or more sub-sample(s); and e) incubating the sub-sample(s) to which the mixture of luciferin and thermostable luciferase and the known antibiotic have been added at a temperature between 20 and 60° C. (temperature to choose in agreement with the luciferase thermostability parameter), preferably between 35 and 37° C. and measuring bioluminescence in real-time;

wherein the optical density at 600 nm (OD600) of live bacteria in the sub-samples after steps a), b), c) and d) have been performed is at least 0.0002, and wherein an increase of bioluminescence measured in a sub-sample in step e) is indicative that the bacterial sample originating from a subject is sensitive to the added concentration of known antibiotic added to the sub-sample in step d).

Step a): Inoculating a Bacterial Sample Originating from a Subject Suffering from a Bacterial Infection into a Culture Medium and, Optionally, Amplifying the Bacteria in the Sample Step a) of the antibiotic sensitivity determination method of the invention is performed with a sample originating from a subject suffering from a bacterial infection, which has been obtained previously. Said sample may notably be a blood sample, a urine sample, a saliva sample, a faeces sample, a stool sample, a sputum sample, a bronchoalveolar lavage sample, an endotracheal aspirate sample, a oropharyngeal or nasopharyngeal sample, a skin sample, a wound sample, a sample from body fluids (for example the cerebrospinal fluid, the bile fluid, the pleural fluid), vaginal or abdominal abscess discharges or a tissue sample.

In step a), said sample is inoculated to a culture medium. Said culture medium should be able to sustain bacterial cells viability during the test. Such mediums are well known in the art and notably include rich media (such as the cation-adjusted Muller-Hinton (MH) and the lysogeny broth (LB)) and minimal media complemented with a source of carbon like glucose (such as MOPS-Glucose), as defined and disclosed above with respect to the screening method of the invention. The media of reference in international guidelines for antibiotic susceptibility testing is the un-supplemented cation-adjusted MH broth for testing of non-fastidious organisms and the MH-F (cation-adjusted MH broth supplemented with 5% mechanically defibrinated horse blood and 20 mg/L B-NAD) for testing fastidious organisms. EUCAST, under the auspices of the European Society of Clinical Microbiology and Infectious Diseases (ESCMID) and the European Centre for Disease Prevention and Control (ECDC) provides regularly updated guidelines.

If necessary, the bacteria contained in the sample are amplified in order to reach an optical density at 600 nm (OD600) sufficient to have a final OD600 at the end of step d) (after both the mixture of luciferin and thermostable luciferase and the known antibiotic have been added) of at least 0.0002, preferably at least 0.0003, at least 0.0005, at least 0.001, at least 0.005, at least 0.01, more preferably at least 0.015, preferably between 0.0002 and 0.5, between 0.0003 and 0.5, between 0.0005 and 0.5, between 0.001 and 0.5, between 0.005 and 0.5, between 0.01 and 0.5, between 0.015 and 0.5, between 0.1 and 0.5, between 0.1 and 0.3, more preferably between 0.1 and 0.2 and in particular 0.15, as disclosed herein in the context of the method for screening bactericidal compounds according to the invention. Preferably, when the volumes added in steps c) and d) result in a dilution factor of about 2 (i.e. the volume after both additions is about twice the initial volume of the sub-sample in step b)), the pathogenic bacteria are amplified to reach an OD600 of at least 0.0004, at least 0.0006, at least 0.001, at least 0.002, at least 0.01, at least 0.02, at least 0.03, preferably comprised between 0.0004 and 0.6, between 0.0006 and 0.6, between 0.001 and 0.6, between 0.002 and 0.6, between 0.01 and 0.6, between 0.03 and 0.6, between 0.1 and 0.6, between 0.2 and 0.6, more preferably between 0.2 and 0.4, most preferably about 0.3. Amplification of bacteria in culture medium may be performed according to any method known in the art.

As for the screening method of the invention, the antibiotic sensitivity determination method preferably excludes any chemical or mechanical manipulation on the pathogenic bacteria in the tested sample which could disturb their physiology or damage them, i.e. any manipulation susceptible to induce chemical or mechanical stress on the live bacteria in the sample. Therefore, in accordance with one embodiment of the antibiotic sensitivity determination method, the bacteria of the test sample in step a) have not been subjected to a mechanical (particularly a centrifugation) or chemical (particularly an osmotic shock) stress, particularly susceptible to damage the bacterial structure and/or the bacterial membrane and its functions. The mechanical stress and the chemical stress as defined as indicated above for the screening method of the invention.

In some embodiments of the antibiotic sensitivity determination method of the invention, the type of bacteria present in the bacterial sample is not known, which does not preclude the implementation of the antibiotic sensitivity determination method of the invention. Several distinct classes of antibiotics may then be tested for sensitivity of the bacterial sample.

In other embodiments, the type (species or at least genera) of bacteria present in the bacterial sample is known from other analytics methods. This may favor the test of particular classes of antibiotics, known in the art to be efficient against non-resistant bacteria of the type present in the bacterial sample. In particular, some species and genera of bacteria are known to be particularly associated to bacterial infections in animals, and more particularly in mammals including humans and are of particular medical interest. Such bacteria may thus preferably be tested in the antibiotic sensitivity determination method according to the invention. These include for instance Coagulase-negative staphylococci, *Mycobacterium tuberculosis*, many *Streptococcus* (such as *Streptococcus pneumoniae*, *Streptococcus pyogenes*) and *Pseudomonas* (such as *Pseudomonas aeruginosa*), *Enterococcus faecalis*, *Escherichia coli*, *Proteus mirabilis*, *Serratia marcescens*, *Citrobacter freundii*. Also of strong interest is the ESKAPE group of antibiotic-resistant "priority pathogens" as defined by the World Health Organization (WHO). ESKAPE is an acronym for designing Gram-positive and Gram-negative species: *Enterococcus faecium, Staphylococcus aureus, Klebsiella pneumoniae, Acinetobacter baumannii, Pseudomonas aeruginosa*, and *Enterobacter* species. WHO published a catalogue of 12 families of bacteria that pose the greatest threat to human health. These include: *Helicobacter pylori* (clarithromycin-resistant), *Campylobacter* spp. (fluoroquinolone-resistant), Salmonellae (fluoroquinolone-resistant), *Neisseria gonorrhoeae* (cephalosporin-resistant, fluoroquinolone-resistant), *Streptococcus pneumoniae* (penicillin-non-susceptible), *Haemophilus influenzae* (ampicillin-resistant), *Shigella* spp. (fluoroquinolone-resistant).

Step b): Dividing the Bacterial Sample of Step a) into Several Sub-Samples, with at Least as Many Samples as the Number of Known Antibiotics to be Tested In step b) of the antibiotic sensitivity determination method of the invention, the bacterial sample of step a) is divided into several sub-samples, which number corresponds at least to the number of known antibiotics to be tested. All sub-samples preferably contain the same volume of culture medium and have the same OD600 of at least 0.1, preferably between 0.15 and 0.5, more preferably about 0.3.

Step c): Adding a Mixture of Luciferin and a Thermostable Luciferase to Each Sub-Sample The antibiotic sensitivity determination method of the invention is based on the same principle as the screening method of the invention, i.e. the conversion by luciferase of ATP or analogues leaked by bacteria exposed to a bactericidal compound into bioluminescence. Therefore, the same thermostable luciferases and luciferin described above in the context of the screening method of the invention may be used in the antibiotic sensitivity determination method according to the second aspect of the invention, in the same conditions.

According to one embodiment of the sensitivity detection method of the invention, prior to step d), a short preincubation step (3 to 10 minutes, such as 3, 4, 5, 6, 7, 8 minutes, in particular 4 to 6 minutes, preferably 5 minutes) is performed in order to progressively reach the incubation temperature and to remove possible pre-existing extracellular ATP (by conversion by luciferase before addition of the antibiotic).

Step d): adding each of the group of known antibiotics to at least one sub-sample After adding luciferin/thermostable luciferase in step c), each antibiotic of the group of tested known antibiotics to which the sensitivity of the bacterial sample is to be determined is added to at least one sub-sample in step d).

Any antibiotic known to have a bactericidal effect (i.e. susceptible to kill bacteria) on at least some bacteria (i.e. non-resistant bacteria) may be tested for sensitivity and thus added to at least one sub-sample in step d). Preferably, the antibiotics tested for sensitivity are known bactericidal antibiotics selected from the group consisting of:

aminoglycosides (such as streptomycin, kanamycin, gentamicin, neomycin, amikacin, tobramycin, netilmicin);

beta lactams, including penams (such as penicillin, amoxicillin and ampicillin); carbapenams; clavams (such as clavulanic acid); penems; carbapenems; cephems (such as cephalexin or cefpodoxime); carbacephems; oxacephems; and monobactams;

quinolones, including fluoroquinolones (such as ofloxacin; levofloxacin, cyprofloxacin);

polypeptides (such as polymyxin B); glycopeptides and lipoglycopeptides (vancomycin; teicoplanin; oritavancin; dalbavancin; telavancin).

Trimethoprim alone or in combination with sulphamethoxazole Trimethoprim is bactericidal in rich media. Results with this antibiotic should be analyzed with care as the inventors noticed that at a concentration above 200 µg/mL, the drug inhibits the luciferase reaction.

Oxazolidinone, linezolid (can have bactericidal activity even though it is usually classified as bacteriostatic), tedizolid.

Macrolides, erythromycin, telithromycin, azithromycin, roxithromycin which are reported to have bactericidal and bacteriostatic activities.

Among known bactericidal antibiotics, a preferred list of antibiotics from which the antibiotics to which sensitivity of the bacterial sample is determined by the antibiotic sensitivity determination method of the present invention are selected includes: amoxicillin, amoxicillin-clavulanic acid, ampicillin, ticarcillin, piperacillin-tazobactam, ertapenem, cefoxitine, cefixime, ceftriaxone, cefotaxime, ceftazidime, gentamicin, amikacin, nalidixic acid, ofloxacin, ciprofloxacin, fosfomycin and trimethoprim-sulfamethoxazole.

According to one embodiment, the sensitivity determination method of the invention may also be implemented for determining the sensitivity of a combination of known antibiotics. For example, such a combination of antibiotics corresponds to antibiotics usually used in combination (administered simultaneously or sequentially) for treating a disease caused by one or more bacteria.

While less preferred, the antibiotic sensitivity detection method of the invention may also be performed for testing antibiotics known to have a bacteriostatic effect (i.e. antibiotics blocking bacteria growth and proliferation without killing them) on at least some bacteria. Indeed, while data obtained by the inventors show that no ATP or analogues are leaked by bacteria in the presence of a bacteriostatic compound, some compounds may be bacteriostatic at lower concentrations and bactericidal at higher concentrations. An antibiotic known to be bacteriostatic on at least some bacteria might thus show bactericidal effect on another bacterial strain or at high concentration. Such antibiotics mainly known as bacteriostatic that may also be tested in the antibiotic sensitivity determination method of the invention may notably be selected from the group consisting of: macrolides (such as azithromycin, erythromycin, telithromycin, roxithromycin); oxazolidinones (such as linezolid); sulfonamides; tetracyclines (such as doxycycline).

At the end of step d) (i.e. once all components of the reaction have been added), the final concentration of tested antibiotics in each sub-sample is preferably comprised between 0.002 μg/mL and 1024 μg/mL as a 2-fold serial dilution (twenty values). For simplicity, the range of concentrations obtained by the 2-fold serial dilution can be comprised between 1/500 and 1000/1, preferably between 1/4 and 4/1, of the known antibiotic MIC for a known sensitive bacterial strain in the culture medium used and preferably below 1024 μg/mL. MIC of known antibiotics in various culture media are either known in the art or may be easily determined by routine experiments by those skilled in the art.

Preferably, at the end of step d) (i.e. once all components of the reaction have been added):

The OD600 of live bacteria is at least 0.1, preferably it is comprised between 0.1 and 0.3, more preferably between 0.1 and 0.2, in particular it is 0.15.

The solution of luciferin is diluted to an optimized concentration, which will be selected either based on the luciferin manufacturer recommendations or based on preliminary test experiments (between 6 and 9 times when the "CheckLite AT100" kit of Kikkoman or NanoLuc® (NLuc) is used);

The solution of thermostable luciferase is diluted to an optimized concentration, which will be selected either based on the luciferin manufacturer recommendations or based on preliminary test experiments (between 6 and 9 times when the "CheckLite AT100" kit of Kikkoman or NanoLuc® (NLuc) is used); and/or The concentration of the known antibiotic comprised between 0.002 μg/mL and 1024 μg/mL, preferably between 1/4 and 4/1, of the known antibiotic MIC for a known sensitive bacterial strain in the culture medium used and preferably kept below 1024 μg/mL.

The above-mentioned values of dilution of luciferin and luciferase solutions may be adapted depending of the instructions provided with the luciferin/luciferase kits.

Step e): Incubating the Sub-Sample(s) at a Temperature Between 20 and 60° C., Preferably Between 35 and 37° C. Under Agitation and Measuring Bioluminescence in Real-Time (Measure Step)

Measure step e) of the antibiotic sensitivity determination method of the present invention which consists in incubating the sub-sample(s) at a temperature between 20 and 60° C. (temperature to choose in agreement with the luciferase thermostability parameter), preferably between 30 and 40° C. and more preferably between 35 and 37° C. under agitation and measuring bioluminescence in real-time correspond to the measure step d) of the screening method of the invention.

All technical features and technical definitions provided above for the measure step d) of the screening method may thus be applied to the measure step e) of the antibiotic sensitivity determination method of the invention.

In particular, the bioluminescence is measured in real time as previously described. An increase of bioluminescence measured in a sub-sample is indicative that the bacterial sample originating from the subject is sensitive to the added concentration of known antibiotic added to the sub-sample in step c).

Order of the Steps

Step a) is performed first and step b) second.

Steps c) and d) are performed after steps a) and b) and before step e). However, provided that they are performed between steps b) and e), steps c) and d) may be performed in any order: step c) before step d), step d) before step c), or both steps c) and d) simultaneously (if the mixture of luciferin and thermostable luciferase and the known antibiotic have been mixed beforehand).

According to a preferred embodiment of the method of the invention, step d) is performed after or simultaneously with step c) in order to improve the real-time measurement of ATP efflux. Indeed, when step d) is performed before step c), the ATP efflux may start before luciferase/luciferin are added and consequently the initial phase of ATP leakage might be missed. Preferably, step d) is performed simultaneously with step c) or after step c). More preferably, step d) is performed after step c), preferably between 2 and 15 minutes after step c), more preferably between 3 and 10 minutes after step c) and even more preferably between 4 and 6 minutes after step c) and particularly about 5 minutes after step c). This delay between steps c) and d) allows the luciferase/luciferin mixture to consume traces of ATP that can be present in the culture of bacteria that might otherwise affect the initial reading of the bioluminescence signal during step d).

If step d) is nevertheless performed before step c), then step c) should be performed as soon as possible after step d), such as less than 1 minute, preferably less than 30 seconds after step d).

Negative and Positive Controls

In order to improve the reliability of the antibiotic sensitivity determination method, said antibiotic sensitivity detection method preferably also measures bioluminescence in real time in negative and/or positive control samples.

A first type of negative control samples are samples comprising at the end of step d) (i.e. just before incubation and real time bioluminescence measuring): culture medium instead of a bacterial sub-sample, a mixture of luciferin and a thermostable luciferase, and a known antibiotic. Indeed, in the absence of a bacterial sub-sample, no bioluminescence is expected.

A second type of negative control samples are samples comprising at the end of step d) (i.e. just before incubation and real time bioluminescence measuring): a bacterial sub-sample, culture medium instead of the mixture of luciferin and a thermostable luciferase, and a known antibiotic. Indeed, in the absence of the mixture of luciferin and a thermostable luciferase, no bioluminescence is expected.

A third type of negative control samples are samples comprising at the end of step d) (i.e. just before incubation and real time bioluminescence measuring): a bacterial sub-sample, a mixture of luciferin and a thermostable luciferase, and culture medium instead of a known antibiotic. Indeed, in the absence of antibiotic, no bioluminescence is expected.

Since the sensitivity of the bacterial sample to known antibiotics is unknown, conventional positive controls (with a compound known to be bactericidal for the bacteria) are not possible. Alternative positive controls using for instance pure ATP may optionally be used instead. In this case, ATP is added in the place of the antibiotics and the measure of bioluminescence performed immediately after. A skilled person in the art will know which concentration of ATP to use from the manufacturer guidelines (for instance a range from 5 to 50 nM).

Implementation of the Antibiotic Sensitivity Determination Method in a Microplate Also in the case of the antibiotic sensitivity determination method of the invention, the method is preferably performed in a microplate, which may have any feature or combination of features described in the above section relating to the screening method.

In this case, in step b) of the antibiotic sensitivity determination method of the invention, the bacterial sample of step a) is divided into several sub-samples, which number corresponds at least to the number of known antibiotics to be tested and which are dispensed to several distinct wells of a microplate. Here also, all sub-samples preferably contain the same volume of culture medium and have the same OD600 (calculated to reach a final OD600 once all components of the reaction have been added of at least 0.0002, preferably at least 0.0003, at least 0.0005, at least 0.001, at least 0.005, at least 0.01, more preferably at least 0.015, more preferably between 0.0002 and 0.5, between 0.0003 and 0.5, between 0.0005 and 0.5, between 0.001 and 0.5, between 0.005 and 0.5, between 0.01 and 0.5, between 0.015 and 0.5, between 0.1 and 0.5, between 0.1 and 0.3, even more preferably between 0.1 and 0.2, in particular about 0.15). In order to have a first type of negative control, some wells of the microplate may be dispensed with culture medium without bacteria.

In step c), a mixture of luciferin and a thermostable luciferase to wells of the microplate containing a bacterial sub-sample and optionally to well(s) of the microplate containing culture medium without bacteria. In order to have a second type of negative control, some wells of the microplate previously dispensed with a bacterial sub-sample may receive culture medium instead of the mixture of luciferin and a thermostable luciferase.

In step d), antibiotics to which the sensitivity of the bacterial sample is to be tested are added to distinct microplate's wells. The same antibiotic may be added to several distinct wells, in order to test the sensitivity of the bacterial sample to distinct concentrations of the antibiotic and/or to reproduce the measure (duplicates or triplicates) in order to improve reliability of the results. Similarly, several wells with the same negative control may also be present in the microplate (duplicates or triplicates for instance). In order to have a third type of negative control, some wells of the microplate previously dispensed with a bacterial sub-sample and a mixture of luciferin and a thermostable luciferase may receive culture medium instead of a known antibiotic.

The microplate may also contain one or more wells comprising positive control samples, as disclosed above.

Method for Assessing the Minimum Inhibitory Concentration (MIC) of a Bactericidal Compound (MIC Assessing Method)

The inventors also demonstrated that, using real-time monitoring of the reaction of luciferase with ATP or analogs thereof, it is possible to assess a compound minimal inhibitory concentration (MIC) on a given bacterial sample based on measure of the lag time between antibiotic compound addition and detection of ATP leakage at varying antibiotic concentrations.

In the context of the present invention, the term "minimum inhibitory concentration (MIC)" designs the lowest concentration of an antimicrobial compound that is able to inhibit the visible growth of a microorganism after overnight incubation.

In accordance with a third aspect, the present invention thus relates to a method for assessing the minimum inhibitory concentration (MIC) of a bactericidal compound comprising:

a) providing at least one test bacterial sample comprising live bacteria in a culture medium at an optical density at 600 nm (OD600) of at least 0.0002;

b) dividing the bacterial sample of step a) into several sub-samples, c) adding a mixture of luciferin and a thermostable luciferase to said sub-samples;

d) adding varying concentrations of a bactericidal compound to said sub-samples;

e) incubating the sub-samples to which the mixture of luciferin and thermostable luciferase and the bactericidal compound have been added at a temperature between 20 and 60° C. (temperature to choose in agreement with the luciferase thermostability parameter), preferably between 35 and 37° C. and measuring bioluminescence in real-time, wherein the optical density at 600 nm (OD600) of live bacteria in the sub-samples after steps a), b), c) and d) have been performed is at least 0.0002, and preferably 0.15, f) determining for each concentration of bactericidal compound tested the lag time between the time when said bactericidal compound has been added and the time of detection of an increase in the bioluminescence signal, g) representing the lag time in function of the bactericidal compound concentration, h) creating an exponential decay curve fitting the measured points of the lag time in function of the bactericidal compound concentration, i) determining the lowest bactericidal compound concentration in the plateau of the exponential decay fitting curve, j) determining the lag time amplitude of the exponential decay fitting curve, and k) assessing the MIC, wherein the MIC is assessed as comprised between:

the antibiotic concentration corresponding on the exponential decay fitting curve to a lag time equal to (lag time at plateau+0.3× lag time amplitude), and the lowest bactericidal compound concentration in the plateau of the exponential decay fitting curve.

Steps a) to e)

Steps a) to e) of the MIC assessing method of the invention correspond to steps a) to e) of the antibiotic sensitive determination method of the invention and are performed in the same manner. Particularly in the MIC assessing method of the invention, in order to be able to determine the lag time between the time when said bactericidal compound has been added and the time of detection of an increase in the bioluminescence signal, measure step e) preferably starts as soon as step d) is done, i.e. as soon as the bactericidal compound has been added to the mixture of a bacterial sub-sample, luciferin and thermostable luciferase.

Step a) is performed first and step b) second.

Steps c) and d) are performed after steps a) and b) and before step e). However, provided that they are performed between steps b) and e), steps c) and d) may be performed in any order: step c) before step d), step d) before step c), or both steps c) and d) simultaneously (if the mixture of luciferin and thermostable luciferase and the known antibiotic have been mixed beforehand).

According to a preferred embodiment of the method of the invention, step d) is performed after or simultaneously with step c) in order to improve the real time measurement of ATP efflux. Indeed, when step d) is performed before step c), the ATP efflux may start before luciferase/luciferin are added and consequently the initial phase of ATP leakage might be missed. Preferably, step d) is performed simultaneously with step c) or after step c). More preferably, step d) is performed after step c), preferably between 2 and 15 minutes after step c), more preferably between 3 and 10 minutes after step c) and even more preferably between 4 and 6 minutes after step c) and particularly about 5 minutes after step c). This delay between steps c) and d) allows the luciferase/luciferin mixture to consume traces of ATP that can be present in the culture of bacteria that might otherwise affect the initial reading of the bioluminescence signal during step d).

If step d) is nevertheless performed before step c), then step c) should be performed as soon as possible after step d), such as less than 1 minute, preferably less than 30 seconds after step d).

Step f): Determining for Each Concentration of Bactericidal Compound Tested the Lag Time Between the Time when Said Bactericidal Compound has been Added and the Time of Detection of an Increase in the Bioluminescence Signal In the context of the present invention, the term "lag time" relates to a period between two related events, herewith, between the time of addition of the bactericidal compound and the time when an increase of bioluminescence is first detected.

The inventors observed that there is a delay between the addition of a bactericidal compound and the first detection of an increase in the bioluminescence due to conversion of leaked ATP or its analogue's by luciferase, and that this delay shortens when the concentration of the bactericidal compound increases.

The time of addition of the bactericidal compound is known. After bioluminescence has been measured in step e) for various concentrations of the same bactericidal compound, the bioluminescence curves obtained for each concentration are analyzed to determine in each curve the time when an increase of bioluminescence is first detected. On a bioluminescence curve, this time corresponds to the first time point of the kinetic where the signal is increased compared to the previous point and that this increase continues and indicates the sharp increase due to the effect of the bactericidal antibiotic. More precisely, as in some cases the baseline may slightly increase at the beginning of the kinetic, the initial increase should be considered for the main characteristic peak. This time point can be identified visually or my means of a mathematical analysis. The analysis of the curves can be facilitated by noise reduction (such as Fourier transform, exponential smoothing and moving average) to precisely define the delay. Such analysis can be done using for example Excel Microsoft®.

The lag time obtained for each tested concentration of the bactericidal compound is then calculated by subtracting the time of addition of the bactericidal compound to the time when an increase of bioluminescence is first detected.

Step g): Representing the Lag Time in Function of the Bactericidal Compound Concentration In step g), the lag times obtained at varying tested concentrations of the bactericidal compound may be represented schematically in function of the tested bactericidal concentration. A graph is made, representing on the x-axis the concentrations (µg/mL) of added bactericidal compound and on the y-axis the lag time determined in step f). As many experimental points as the number of tested concentrations of the bactericidal compound are represented on the graph.

Step h): Creating an Exponential Decay Curve Fitting the Measured Points of the Lag Time in Function of the Bactericidal Compound Concentration For all tested bactericidal compounds (see Examples, in particular FIGS. 22-23), the inventors found that the various points of the graph representing lag time in function of the tested bactericidal concentration may be fitted by an exponential decay curve.

Practically, this may be done by entering the x and y coordinates of each experimental points into a software such as software GraphPad Prism or Excel Microsoft® and selecting a single exponential decay fit function to perform the fit. The parameters indicative of the quality of the fit should be judged. In the results of the fit, the value of the plateau and the lag time amplitude (span) of the signal can be access. These parameters are needed for the assessment of the MIC.

Step i): Determining the Lowest Bactericidal Compound Concentration in the Plateau of the Exponential Decay Fitting Curve The plateau represents a limit where the lag time does not further decrease when concentration of the bactericidal compound further increases. On the exponential decay curve, the plateau corresponds to the section of the curve that is horizontal. The plateau is listed in the result parameters of the fit.

One or more of the experimental points may be located in the plateau section of the exponential decay curve. When only one experimental point is located in the plateau section of the exponential decay curve, the concentration of bactericidal compound of this point is taken as the lowest bactericidal compound concentration in the plateau of the exponential decay fitting curve. When several experimental points are located in the plateau section of the exponential decay curve, the point with the lowest concentration of bactericidal compound is selected and the concentration of bactericidal compound of this point is taken as the lowest bactericidal compound concentration in the plateau of the exponential decay fitting curve.

Step j): Determining the Lag Time Amplitude of the Exponential Decay Fitting Curve The "lag time amplitude" is defined as the difference between the value of the lag time at the intercept of the exponential decay fitting curve with the y-axis and the value of the lag time in the plateau section of the exponential decay fitting curve. The lag time amplitude (span) is listed in the result parameters of the fit.

Step k): Assessing the MIC Concentration

In this final step, the MIC concentration of the bactericidal compound is assessed as comprised between:

the antibiotic concentration corresponding on the exponential decay fitting curve to a lag time equal to (lag time at plateau+0.3× lag time amplitude), and the lowest bactericidal compound concentration in the plateau of the exponential decay fitting curve as determined in step i) above.

Examples

Materials and Methods

Bacterial Strains and Growth Conditions

*Escherichia coli* MG1655 and *Micrococcus luteus* were used for antibiotic susceptibility tests. Cultures were grown at 37° C. in the rich Luria broth (LB) (10 g NaCl, 10 g tryptone, and 5 g yeast extract per L) or in the MOPS minimal medium supplemented with 0.4% glucose. *Staphylococcus aureus* USA300 strain was grown in tryptic-soy broth (with 0.25% glucose) at 37° C.

Antibiotics and Reagents

Neomycin (N6386), apramycin (A2024), azithromycin (PHR1088), kanamycin (K1377), spectinomycin (S4014), ampicillin (A9518), tetracycline (T7660), streptomycin (S9137), cephalexin (C4895), Polymyxin B (P4932), erythromycin (E6376), puromycin (P7255), ofloxacin (O8757), amoxicillin (31586), amikacin (PHR1654), cefixime (CDS021590), cefoxitin (C4786), ceftazidime (CDS020667), ceftriaxone (C5793), ciprofloxacin (PHR1167), fosfomycin (P5396), nitrofurantoin (46502), piperacillin (93129), sulfamehoxazol (31737) were purchased from Sigma-Aldrich. Chloramphenicol (018043) was purchased from Eurobio. 3-(N-Morpholino)propane-sulfonic acid (MOPS; M3183) was purchased from Sigma-Aldrich. Glucose (24379.294) was obtained from VWR BDH Chemicals. Bacto™ Tryptone (211705) and Bacto™ Yeast extract were purchased from BD Biosciences Advanced Bioprocessing and Sodium chloride (06404.1000) was obtained from Merck. Bacto Trypic Soy Broth (Ref 0370-17-3) was purchased from Difco.

Real-Time Bioluminescence Assay

The classical luciferase was from Molecular Probes (ATP Determination Kit (A22066)). The thermostable luciferase was from "CheckLite AT100" (kikkoman). The Luciferin-luciferase reagents were prepared following manufacturer instructions. Bacteria from exponentially growing cultures (OD$_{600}$=0.3) were added to each well (60 µl/well) of a black 96-microtiter plate (Greiner Bio-one, 655076) and 20 µl of the luciferin-luciferase reagent solution was added. The microtiter plate was incubated 5 min at 37° C. for reaction with the luciferase to eliminate traces of extracellular ATP. Then 40 µl of antibiotic solution (3 times concentrated) prepared in the culture medium were added. Bioluminescence of each well was monitored for 4 hours under shaking (218 rpm) and at 28 or 37° C., depending on the experiments (see legends of Figures). The reagent stability in presence or absence of antibiotics was checked in control experiments without bacteria but with 4 pmoles of ATP. Tests were also performed in 384-microtiter plates (Greiner Bio-one, 784076).

Detection of Bactericidal Compounds in Supernatants of Drug Producers

The protocol of ATP measurement developed by the inventors was adjusted and optimized in order to increase the sensibility of the test. The same kit "CheckLite AT100" using firefly luciferin and luciferase was used.

Bacteria from exponentially growing culture (OD$_{600}$ of 0.6) in minimal medium (MOPS-glucose 0.4%) were used. A volume of 60 µL of bacterial suspension was added to each well of a black microtiter plate (black walls and black bottom) and 10 µL of the luciferin-luciferase reagent solution were added to each well. The plate was incubated at 37° C. for 5 minutes under shaking (218 rpm) to eliminate possible traces of extracellular ATP released by bacteria. Afterward, 20 µL of *Streptomyces fradiae* supernatant (kept on ice while waiting) were added to each well. Bioluminescence in each well was monitored for 4 hours at 37° C. under shaking (218 rpm) by a microtiter plate reader (InfinitePro200, TECAN).

Resistant Bacterial Strains and Biofilm

Biofilms were produced by following standard protocols. Briefly, *S. aureus* USA300 was incubated overnight in tryptic-soy broth (with 0.25% glucose) at 37° C. with 180 rpm agitation. Wells of a FLUOTRAC™ microplate (sterilized beforehand) were then filled with 150 µl of the inoculated broth previously diluted to obtain average concentrations between $10^5$-$10^6$ CFU/ml. The microplate was covered and incubated at 37° C. for 18 hours. Biofilms were then washed twice with 150 µl of MOPS. 80 µl of the wash solution was not discarded and placed in an adjacent well to observe the quantity of ATP it contained. Next, the optimized protocol developed by the inventors for the bioluminescence assay was followed.

Antibiotic MIC Determination

The Minimal Inhibitory Concentration (MIC) of the antibiotics was determined under the same culture conditions as the tests using the ATP assay kit. Serial twofold dilutions of tested antibiotics were prepared in the LB or MOPS glucose 0.4% medium. An exponentially growing culture (OD$_{600}$=0.3) was added to each well (60 µl/well) of a sterile microtiter plate containing the test concentration of antibiotic (40 µl/well). The volume was completed to 120 µl with medium and OD$_{600\ nm}$ measurements were performed using a microtiter plate reader (Infinite 200 PRO, TECAN) during 17 hours at 37° C.

Results

A Bioluminescence Assay for Real-Time Detection of ATP Leakage

Figure 1:
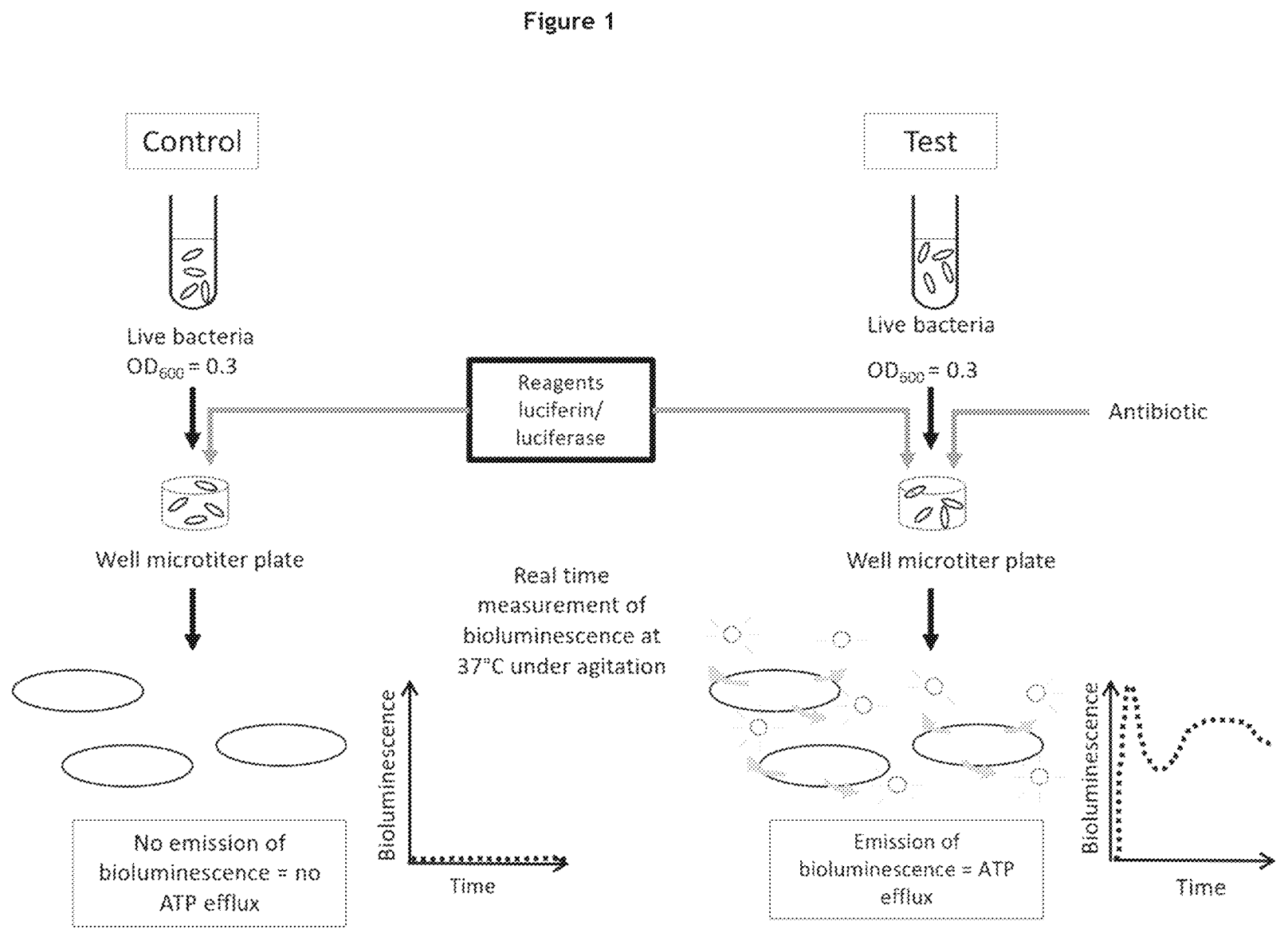

The principle of this assay is shown on FIG. 1.

The inventors first evaluated the possibility to detect ATP with a classical firefly luciferase in rich and minimal media. Addition of ATP to a rich medium, Luria Broth (LB) or a minimal medium (MOPS) containing the luciferin/luciferase reagents triggered luminescence. Stability of reagents was superior in LB medium (FIG. 2*a*). In MOPS, reagents were rapidly inactivated when preincubated with the medium (FIG. 2*a*). The inventors next evaluated the response of live reporter *Escherichia coli* cells following an antibiotic shock with an aminoglycoside, neomycin, known to trigger leakage of small molecules (amino-acids, nucleotides, potassium). Luminescence measurements demonstrated that the assay reports in real time on antibiotic-dependent leakage of ATP (FIG. 2*b*). The inventors also assessed the performance of this assay with rich (LB) or minimal (MOPS) media. In minimal media, the luminescence signal was not detectable (FIG. 2*b*) due to the instability of one or several reagents as observed in FIG. 2*a*. Firstly, the inventors concluded that this result showed that some constituents of the rich growth media probably acted as stabilizing agents of the luciferase in the bioluminescence assay. However, given that the assay was performed at 28° C. (temperature which is under 37° C., temperature usually used for growing bacteria), the inventors performed another assay at 37° C. The obtained results were not satisfying since at 37° C., the stability of classical luciferase in rich and in minimal media is low and its activity decreases rapidly. Regarding control samples without the addition of the antibiotic, it appears that they did not give any signal demonstrating that the ATP release was antibiotic dependent (FIG. 2b).

To investigate whether better stability of the firefly luciferase would improve measurements in minimal and in rich media the inventors performed the same assay using a thermostable firefly luciferase (FIG. 2c). Antibiotic-dependent luminescence signals could be recorded in both minimal and rich media establishing the conditions for a real-time ATP assay on live E. coli bacteria (FIG. 2c). The emission of light being immediate upon contact between ATP, luciferin and luciferase, the assay reports on ATP (or analogs) efflux outside the outer membrane in real time. The inventors noted the better performance of the thermostable luciferase in minimal media (MOPS) compared to rich media (LB) (FIG. 2d). As the thermostable luciferase permits performing the test in rich and minimal media, further developments of the method were performed using this enzyme.

To confirm the results obtained with the classical and with the thermostable luciferase, the inventors performed a comparative assay.

For performing this assay, a classical luciferase (firefly luciferase; Molecular Probes ATP determination kit A22066) and the thermostable luciferase (Checklite kit, Kikkoman, AAE43251.1) were used according to the manufacturer's instructions. Both types of luciferases were added to rich LB or minimal MOPS-Glucose media pre-heated at 37° C. At various times during incubation, aliquots of the solutions were collected, supplemented with reagents and mixed with 0.8 pmole of ATP for bioluminescence readings. Immediately after mixing, bioluminescence measurements were performed at 37° C. using an InfinitePro200, TECAN plate reader in a total volume of 12 μL on a 384-wells microtiter plate (Greiner Bio-one, 784076).

Figure 24:
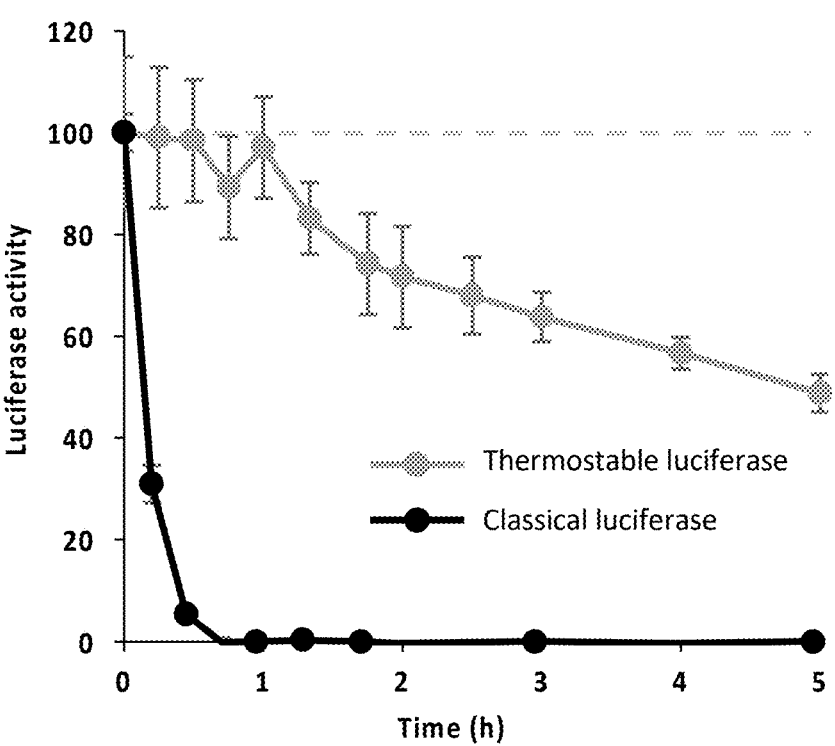
FIG. 24. Comparative assay of the conventional (not thermostable) firefly luciferase and a thermostable luciferase from Kikkoman. Both of these enzymes were incubated at 37° C. in rich (LB) or minimal (MOPS-Glucose) media and the activity of luciferases was measured at various times. Error bars are standard error of mean for three independent assays.
Figure 24:
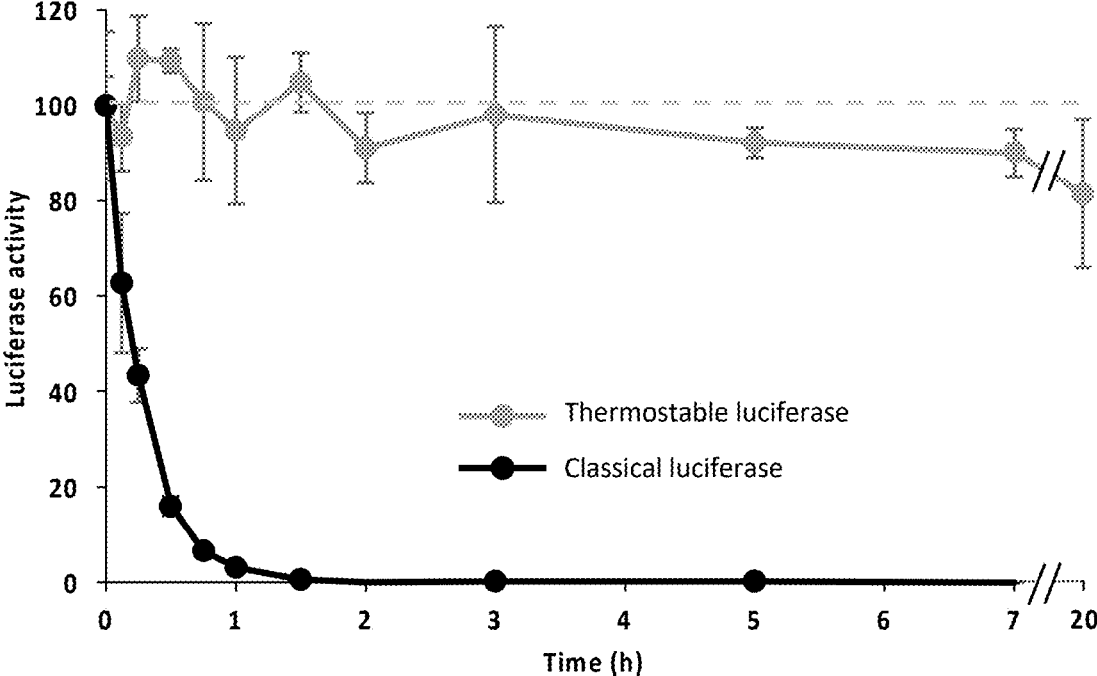

The results shown on FIG. 24 confirm that the classical firefly luciferase is very unstable at 37° C. in both rich (LB) and minimal (MOPS-G) media. In LB medium, the enzyme lost 70% of its activity after just 12 minutes of incubation. In minimal MOPS-G medium, the enzyme lost more than 80% of its activity in 30 minutes. These results demonstrate that conventional (non-thermostable) luciferase is not suitable for performing a real-time assay to detect the efflux of ATP at 37° C., the temperature best suited for bacterial growth.

On the contrary, the same assay performed with the thermostable luciferase (Kikkoman) showed that the enzyme retained 50% of its activity after 5 hours of incubation at 37° C. in LB and 90% of its activity after 7 hours of incubation in MOPS-G (FIG. 24). In MOPS-G, the enzyme even showed extreme stability by retaining more than 80% of its activity after 20 hours of incubation.

From these results it is concluded that at 37° C., the optimal temperature for growing most of bacterial species, the thermostable luciferase is the only enzyme that allows performing a sensitive and reliable real-time ATP leakage assay.

Figure 3:
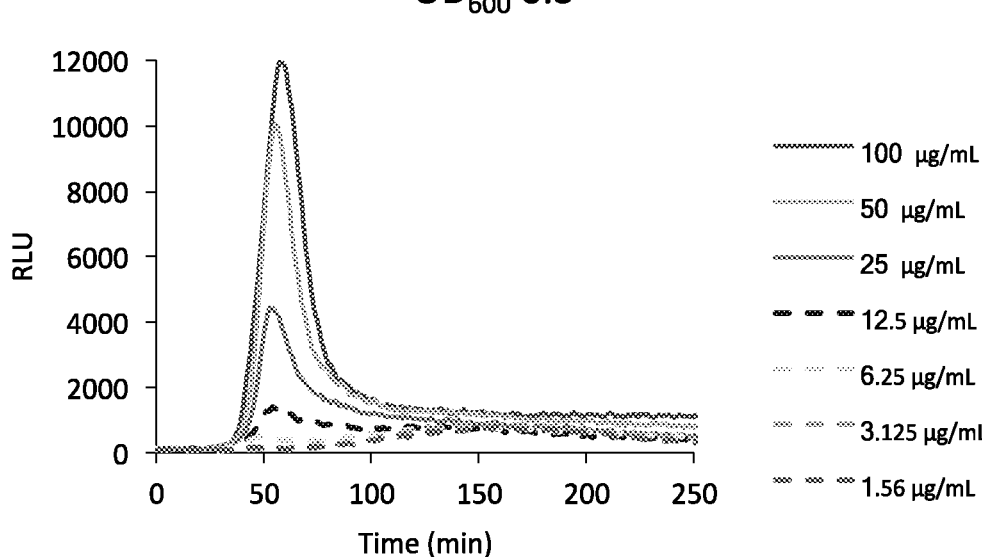
FIG. 3. The quantity of live bacteria (reporter cells) in the assay is important. A, The assay was performed at 37° C. using increasing quantities of *E. coli* reporter cells grown in the Mueller Hinton media. The final $OD_{600}$ values of the cell cultures used are indicated in each panel. B, The maximal value recorded for the highest concentration of neomycin (100 µg/mL) was reported on the graph. A final $OD_{600}$ of 0.15 is well suited for the assay.
Figure 3:
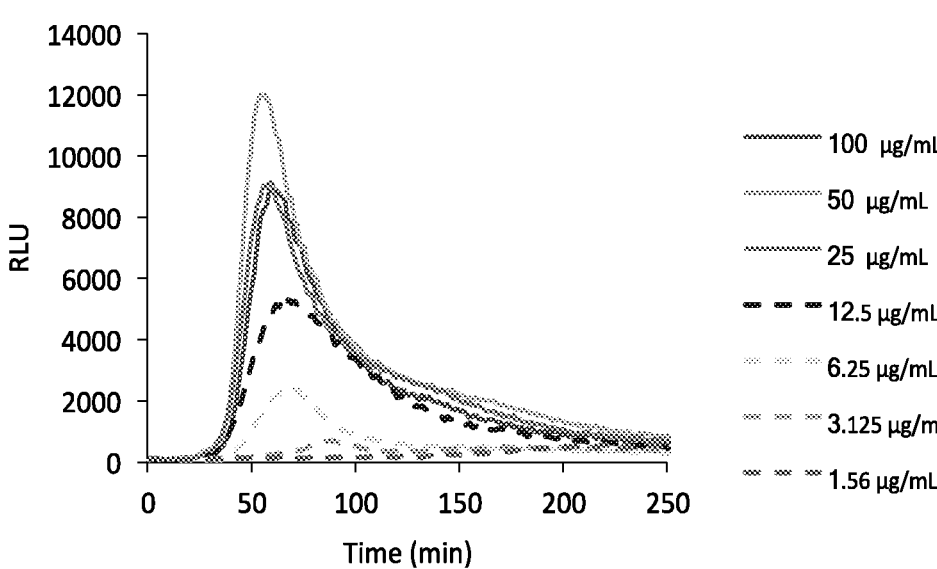
Figure 3:
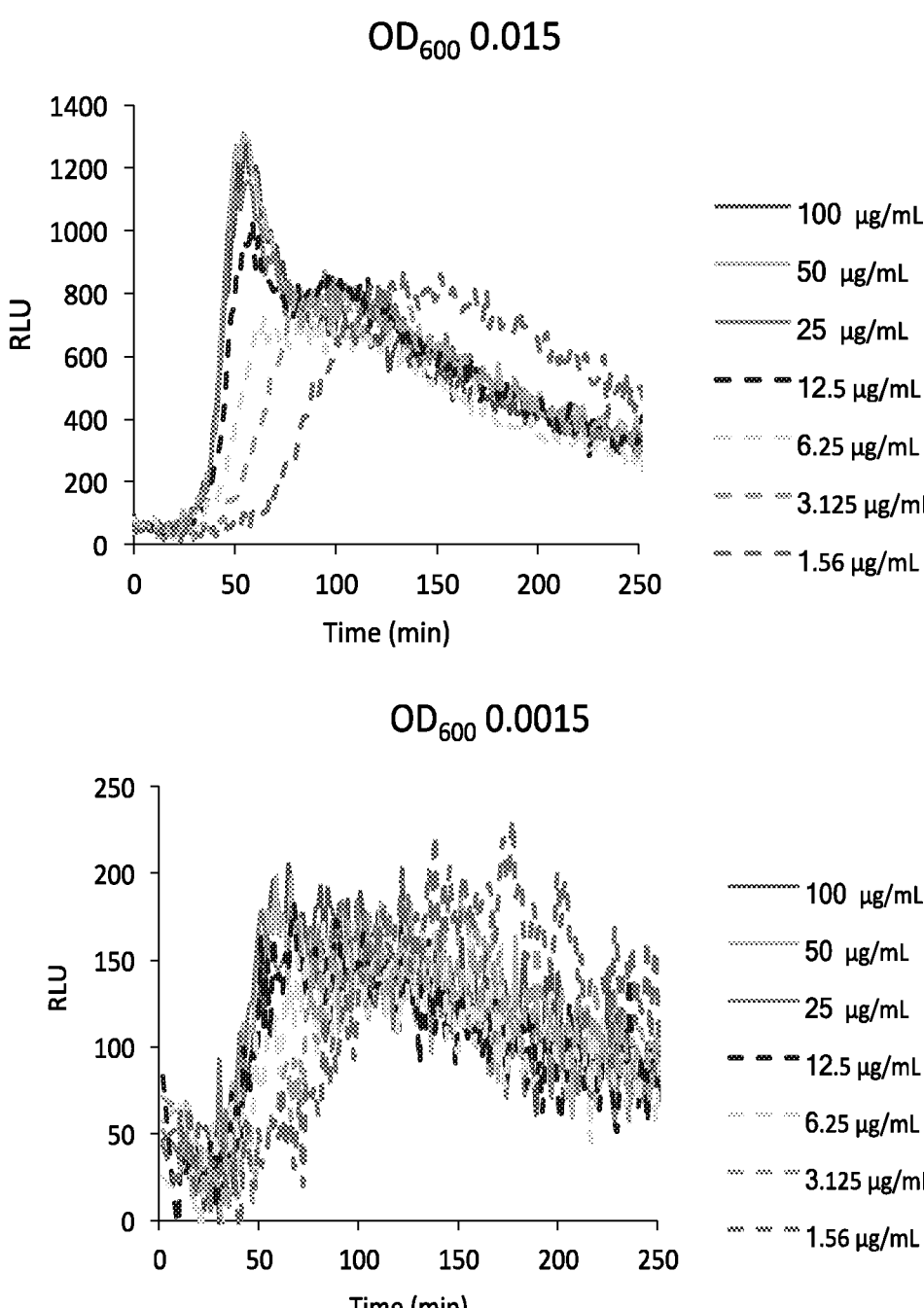
Figure 3:
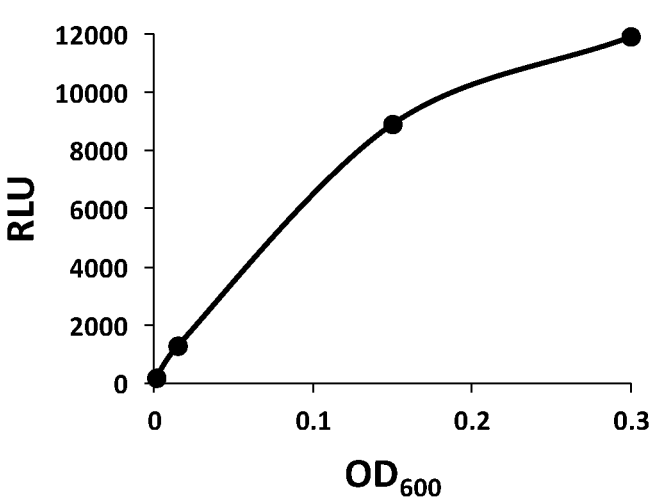

The quantity of reporter cells (bacteria in the tested sample) is important for the assay. Bioluminescence signals were found to be dependent on the concentration of reporter cells. Decreasing the amount of bacteria resulted in a decrease of the bioluminescence signals (FIG. 3). The amplitude of the signal also varied as a function of the cell OD. The inventors firstly found that at lower quantities of cells ($OD_{600}$ 0.0015 and 0.015) weak concentrations of drugs generated bioluminescence signals but these signals only moderately increased with drug concentrations. An $OD_{600}$ of 0.15, provided signals with a large amplitude and was therefore chosen for the assay.

Then, the inventors challenged the screening method of the invention by changing the amount of reporter cells when using cation-adjusted Mueller-Hinton medium, a medium frequently used for clinical AST. The sensitivity of the method using white microtiter plates has been improved and the EUCAST inoculum value recommendations have been reached (FIG. 25). Cells were grown in Mueller-Hinton medium to an OD600 of 0.6 and then diluted to an OD600 of 0.00055 in Mueller-Hinton medium, before addition of luciferin/luciferase followed by addition of antibiotic (60 μL of bacteria at OD600=0.00055+20 μL of reagents (luciferin/luciferase)+40 μL of antibiotic) just before to be used in the ATP bioluminescence assay. The final OD600 of bacteria is 0.000275. The assay was performed with various drug concentrations. White 96-well microtiter plates (Greiner Bio-one, 655075) were used. To gain in precision in the identification of delay times, especially for conditions of weak signal, short-term fluctuations in the ATP leakage traces were smoothed using a 5-point moving average method. This facilitated the identification of the delay times before onset of ATP leakage for estimation of MIC. The results of the analysis of lag time provided an estimate of the MIC are similar to that obtained from a standard growth assay in this medium (FIG. 25).

Small traces of extracellular ATP were detected in the cell cultures and consumed by the luciferase during the 5-minute preincubation prior to the addition of the drugs. The inventors found that it was not necessary to wash the cells by centrifugation for exchanging the culture media with fresh media. Indeed, the inventors showed that centrifugation and subsequent cell manipulation could stimulate uptake of aminoglycoside antibiotics (FIG. 4A). Therefore, manipulation of the reporter cells should be avoided to prevent introducing bias in the results.

The inventors also performed an assay wherein bacteria were centrifuged or not and the drug (neomycin) was added only after various time points (a few minutes, 5 minutes, 15 minutes, 30 minutes . . . and up to 120 minutes) after centrifugation in order to let bacteria recover from the stress induced by centrifugation. The inventors thus found that it takes approximately 2 hours (120 minutes) post-centrifugation for the bactericidal effect of neomycin to be back to a similar level as in non-centrifuged samples (FIG. 4B).

Figure 5:
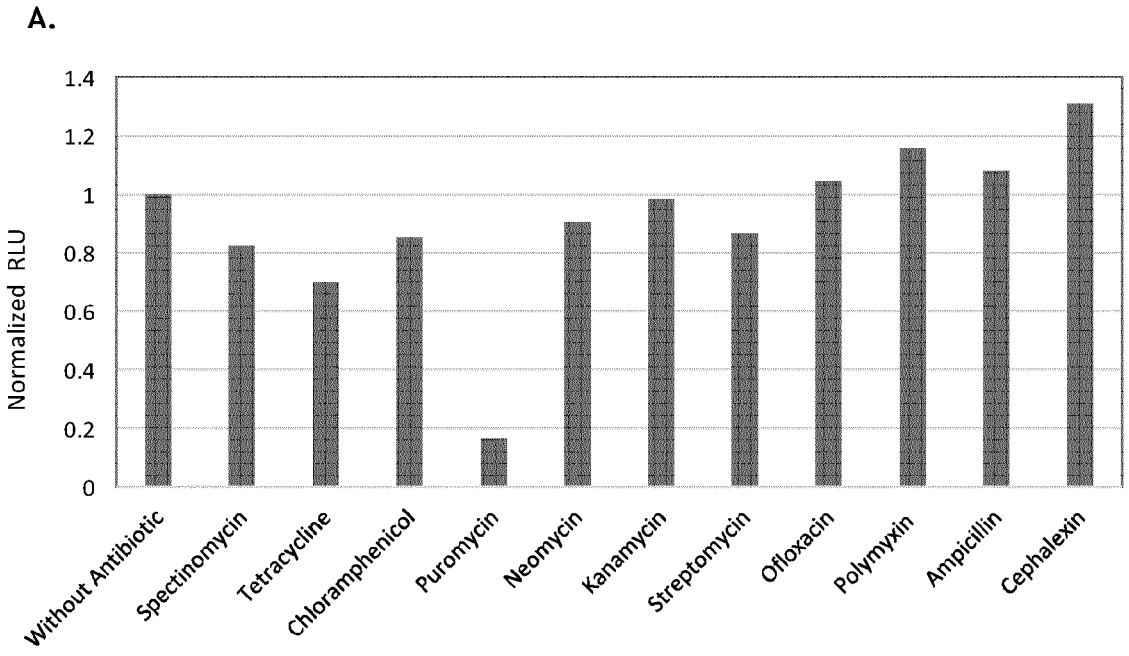
FIG. 5. Tested antibiotics alone generally have no impact on the bioluminescence assay (thermostable luciferase). The luciferase-luciferin reagent was preincubated 40 min at 37° C. in presence of various antibiotics in LB before the addition of 30 nM ATP (in the absence of bacteria). A, RLU (maximal values) with a set of antibiotics at their maximal concentration used in this study. B, Evaluation of the effect of puromycin in the bioluminescence assay. For concentrations above the MIC (377 µg/mL), inhibition of bioluminescence was strong and above 50%.
Figure 5:
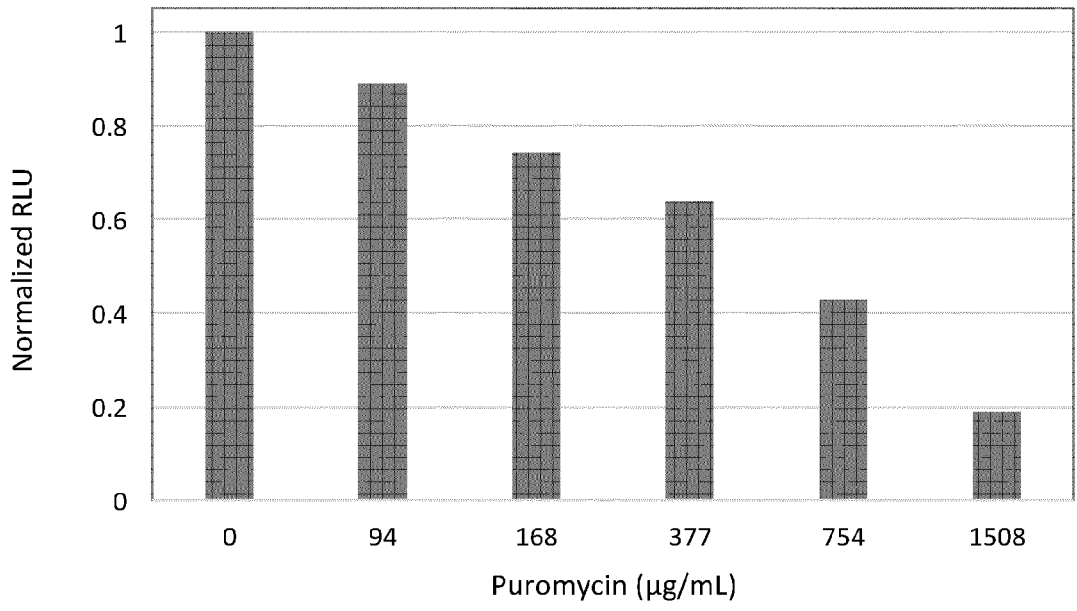

The inventors verified that the presence of the different tested antibiotics had no effect on the activity of the bioluminescence assay (FIG. 5). Bioluminescence was thus measured after preincubation of luciferase-lucifering reagent with the antibiotics at their maximal concentration used in this study in LB before the addition of 30 nM ATP (in the absence of bacteria). A significant inhibition of bioluminescence was observed for puromycin (FIG. 5), an adenosine containing 3' end analogue of aminoacylated tRNAs, but only at a concentration above the measured minimum inhibitory concentration (MIC) for E. coli (FIG. 5 and Table 1). A similar observation was made for actinomycin D, novobiocin and trimethoprim.

TABLE 1

| MIC in μg/ml of the different antibiotics tested | | |
| Antibiotic | MIC in LB | MIC in MOPS glucose 0.4% |
| --- | --- | --- |
| Amikacin | 12.5 | 1.56 |
| Amoxicillin | 12.5 | 12.5 |
| Ampicillin | 25 | 25 |
| Apramycin | 20.2 | 2.5 |
| Azithromycin | 175 | 125 |
| Bleomycin | 100 | 200 |
| Cefixime | 50 | 50 |
| Cefoxitin | 50 | 100 |
| Ceftazidime | 100 | 100 |
| Ceftriaxone | 12.5 | 6.25 |
| Cephalexin | 34.7 | 17.4 |
| Chloramphenicol | 25 | 25 |
| Ciprofloxacin | 25 | 6.25 |
| Erythromycin | 400 | 1600 |
| Fosfomycin | 50 | 100 |
| Gentamicin | 5.7 | 0.6 |
| Kanamycin | 25 | 3 |
| Nalidixic acid | 256 | 256 |
| Neomycin | 22.8 | 0.8 |
| Nitrofurantoin | 50 | 50 |
| Novobiocin | 200 | — |
| Ofloxacin | 4 | 4 |
| Piperacillin | 200 | — |
| Polymyxin B | 8 | 4 |
| Puromycin | 435 | 871 |
| Rifampicin | 50 | 25 |
| Spectinomycin | 50 | 100 |
| Streptomycin | 50 | 6.25 |
| Sulfamethoxazole | — | 1600 |
| Tetracycline | 12.5 | 12.5 |
| Trimethoprim | 50 | 6.25 |
| Zeocin | 200 | 200 |

Figure 6:
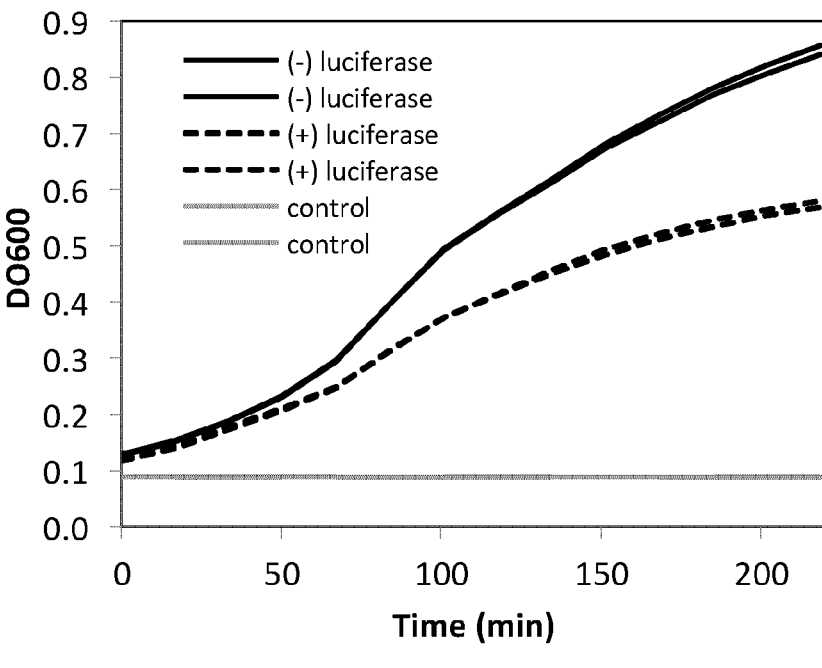
FIG. 6. Bioluminescence reagents preserved cell viability. The reagents of the bioluminescent assay (thermostable luciferase) only slightly slowed down the growth rate of MG 1655 *E. coli* cells in LB. Cells were incubated on the microplate reader at 37° C. in presence or absence of the bioluminescent assay reagents and cellular growth was monitored by optical density measurements. Measurements were made in duplicates and were found identical. The assay was performed in non-sterile conditions.
Figure 7:
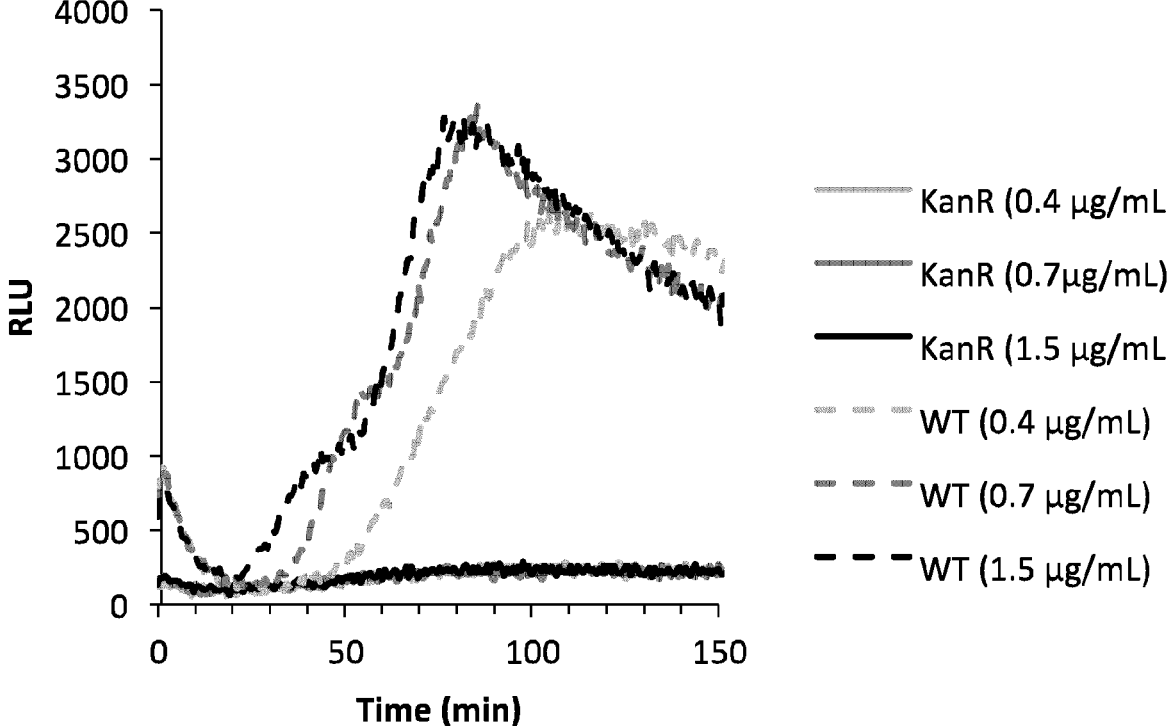
FIG. 7. Absence of ATP leakage with an aminoglycoside resistant strain *E. coli* MG1655. The resistant strain (MG KanR) contains the gene for expression of the aminoglycoside O-phosphotransferase APH(3')-IIa. ATP release of resistant (KanR) or non-resistant (WT) MG 1655 *E. coli* cells exposed in MOPS minimal medium (glucose 0.4%) to increasing concentrations of neomycin at 37° C. ATP leakage was absent for the resistant strain (KanR).

After optimization, the volume of reagents for the bioluminescence assay represented less than 17% of the total volume thereby minimizing the perturbation that might occur on cell viability. Indeed, the inventors demonstrated that cells remained viable under these experimental conditions (FIG. 6). Finally, the inventors performed the ATP leakage assay on an *E. coli* strain resistant to aminoglycosides. The expression of the aminoglycoside O-phosphotransferase APH(3')-IIa prevented the detection of ATP leakage upon the addition of neomycin demonstrating that the drug-induced ATP leakage is due to the bactericidal activity of the drug on bacteria (FIG. 7). This further demonstrate that the method is able to detect sensitivity/resistance of a particular bacterial sample using low antibiotic concentration (MIC or even lower). Having in hand a sensitive bioluminescence assay that reports on ATP leakage on live bacteria (FIG. 1) the inventors set to investigate the responses following shocks to various antibiotics.

Bactericidal Antibiotics Triggered ATP Leakage with Key Signatures

In all the following experiments, the MIC values were measured for each antibiotic with parameters such as temperature, $OD_{600}$ and equipment identical to those used for the bioluminescence assay.

Figure 8:
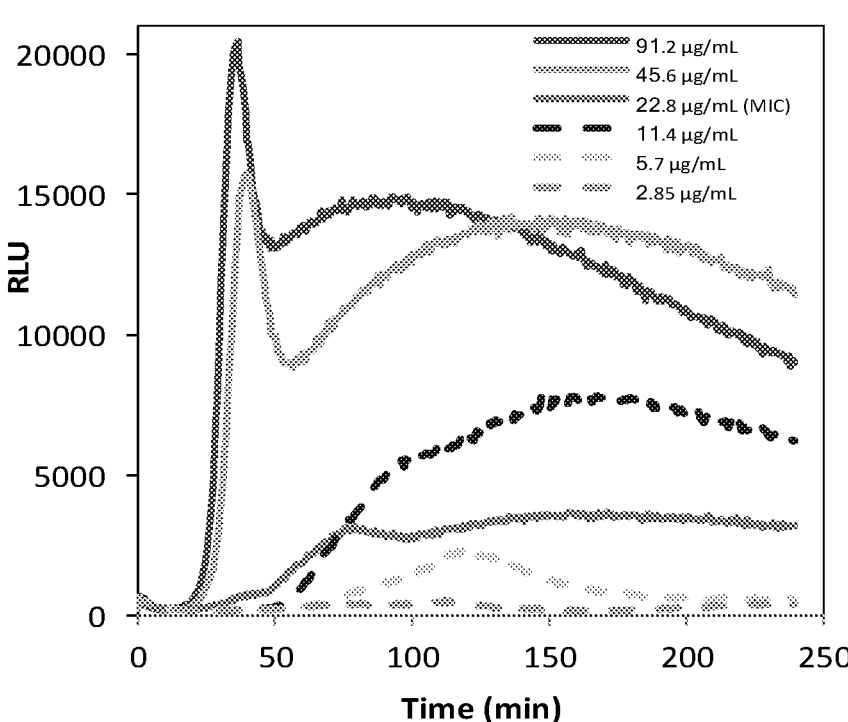
FIG. 8. Bactericidal antibiotics triggered mono or multiphasic traces for ATP release. Representative traces of bioluminescence measurements obtained at 37° C. with *E. coli* reporting cells in LB growth media following the addition of various antibiotics. Bioluminescence signal was acquired for one second every 80 seconds. MIC values are indicated. Upper right panel: in the case of neomycin, kill curves obtained for different drug concentrations showed that during the first 90 minutes, cells remained alive. Therefore, for neomycin, the bi-phasic ATP efflux originated from live cells. The bi-phasic ATP leakage was noted for the other aminoglycosides: kanamycin, streptomycin, amikacin, apramycin and gentamicin. As for neomycin, it was noted that the signal at or close to the MIC is lower than the signal obtained for a concentration just inferior.
Figure 8:
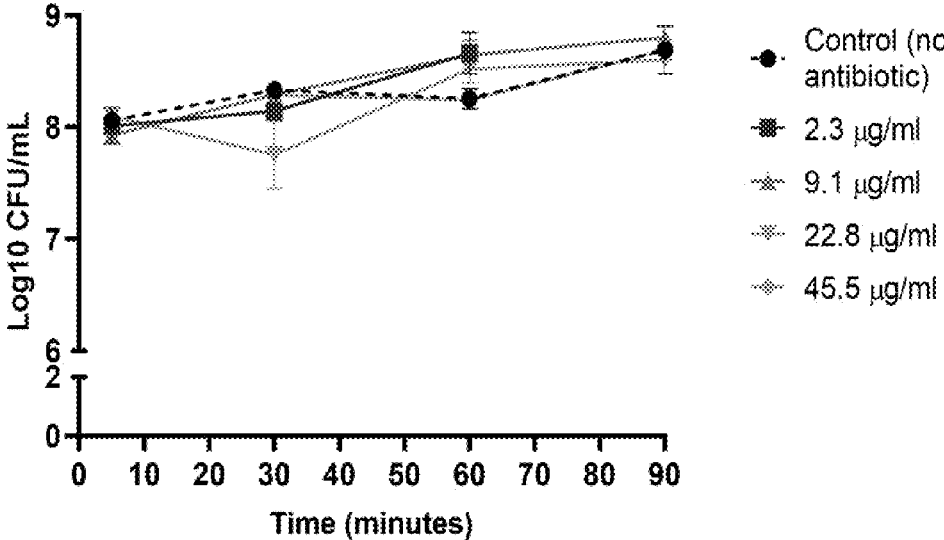
Figure 8:
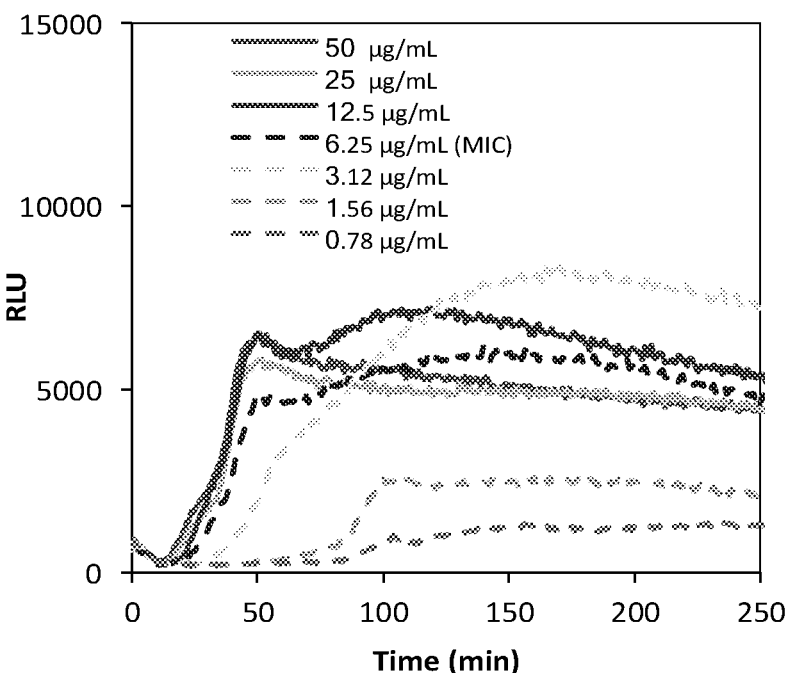
Figure 8:
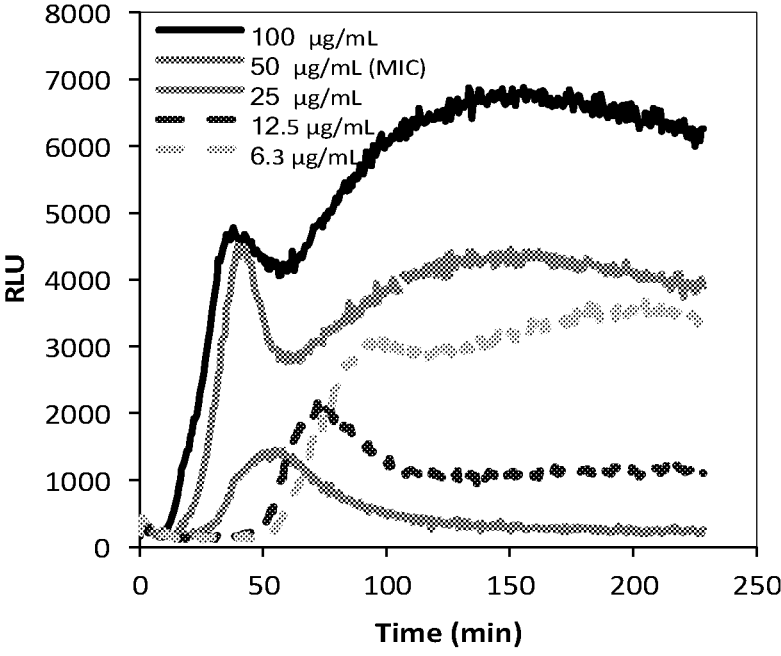
Figure 8:
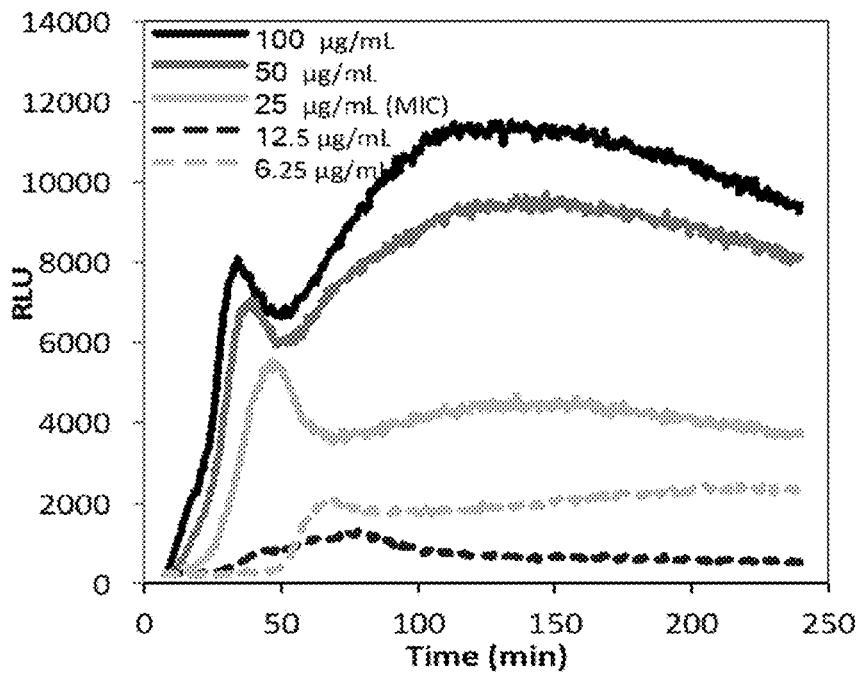
Figure 8:
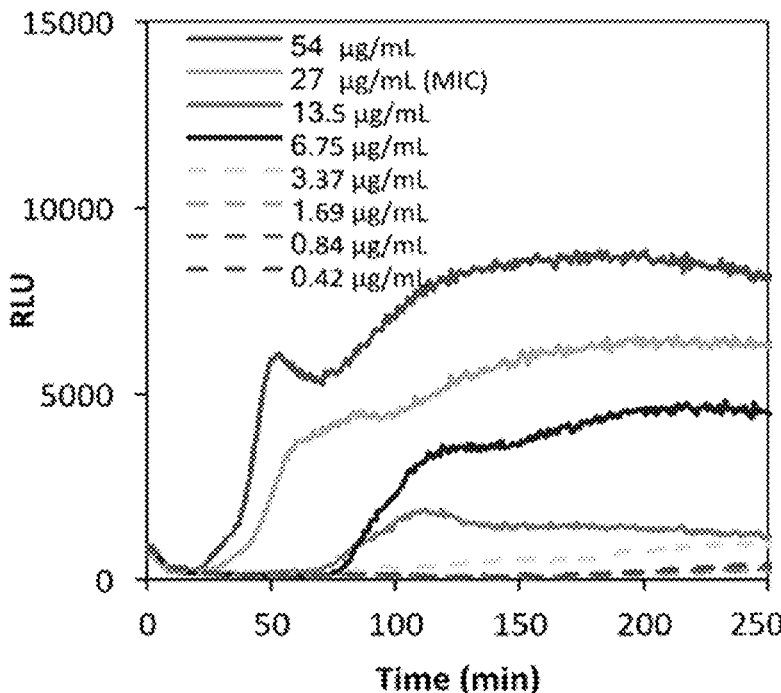
Figure 8:
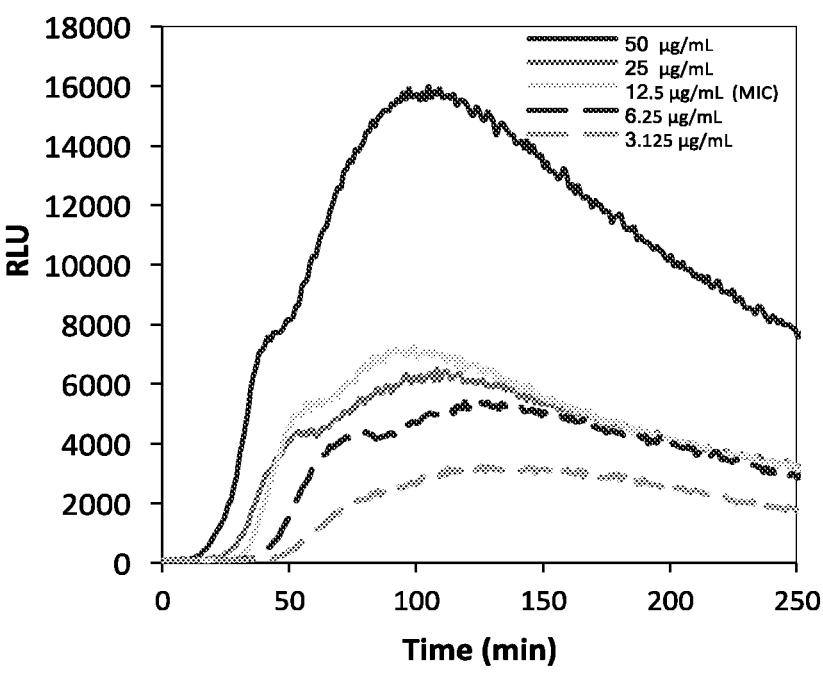
Figure 8:
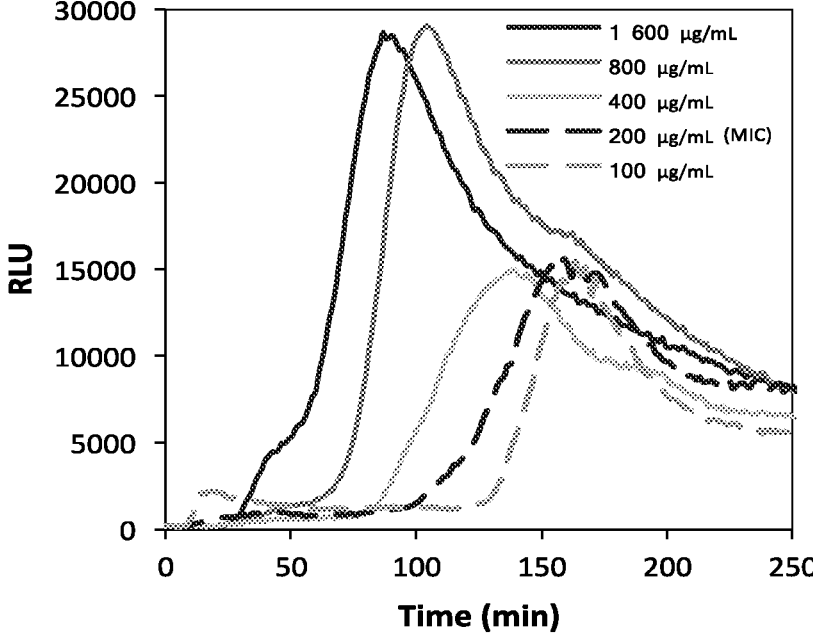
Figure 8:
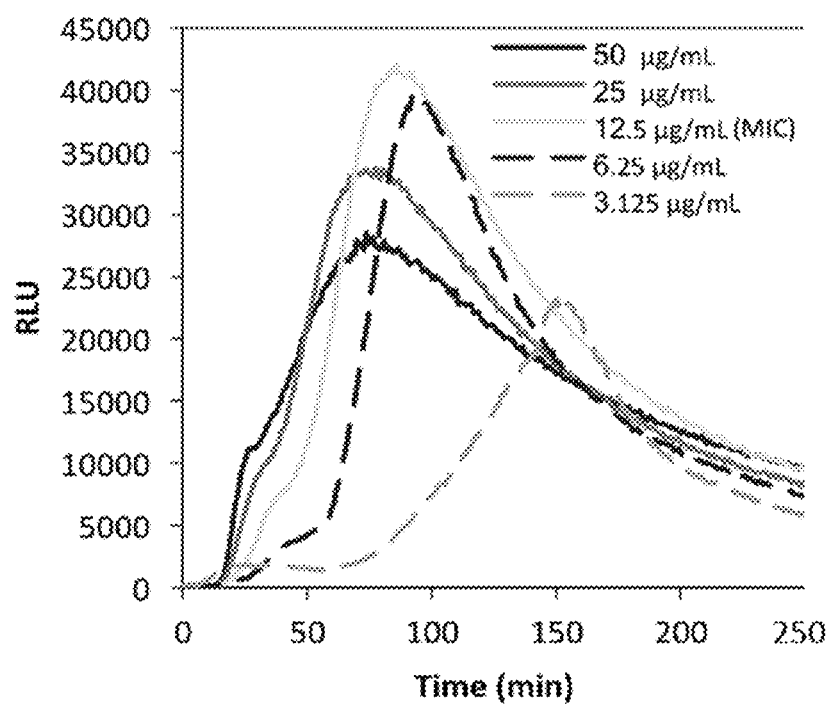
Figure 8:
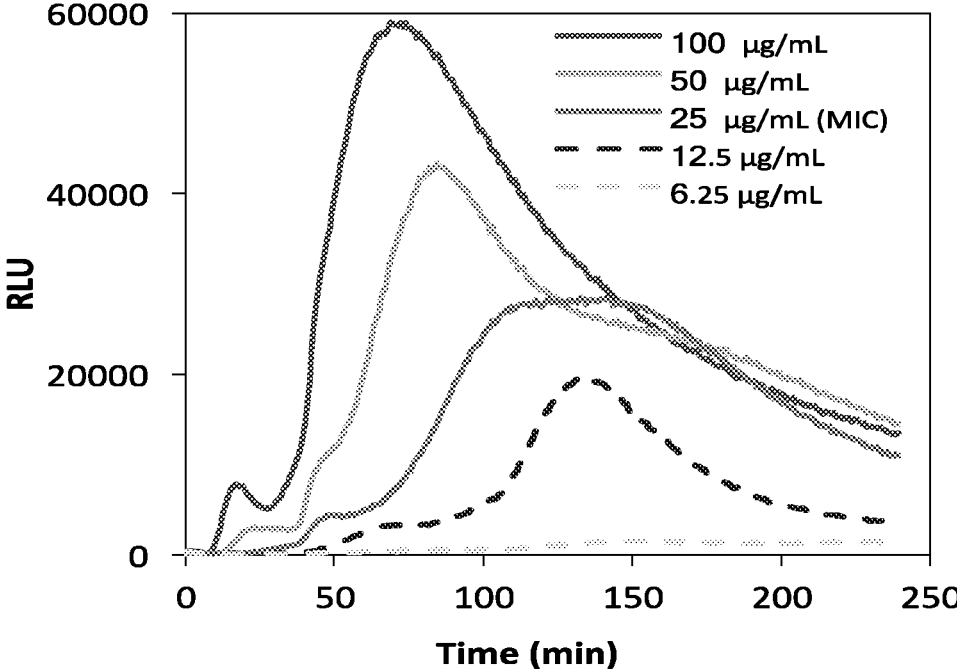
Figure 8:
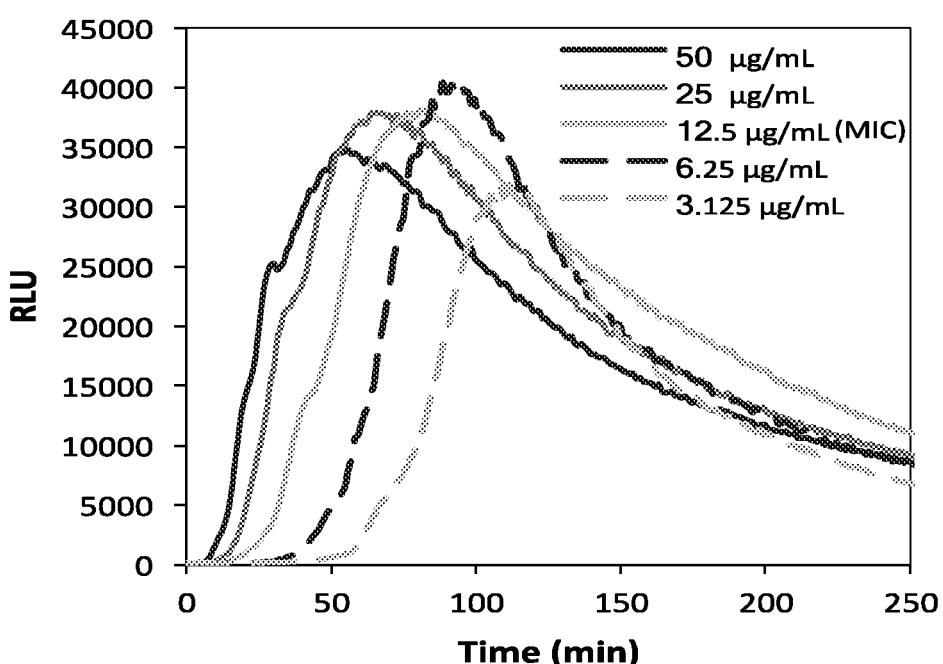
Figure 8:
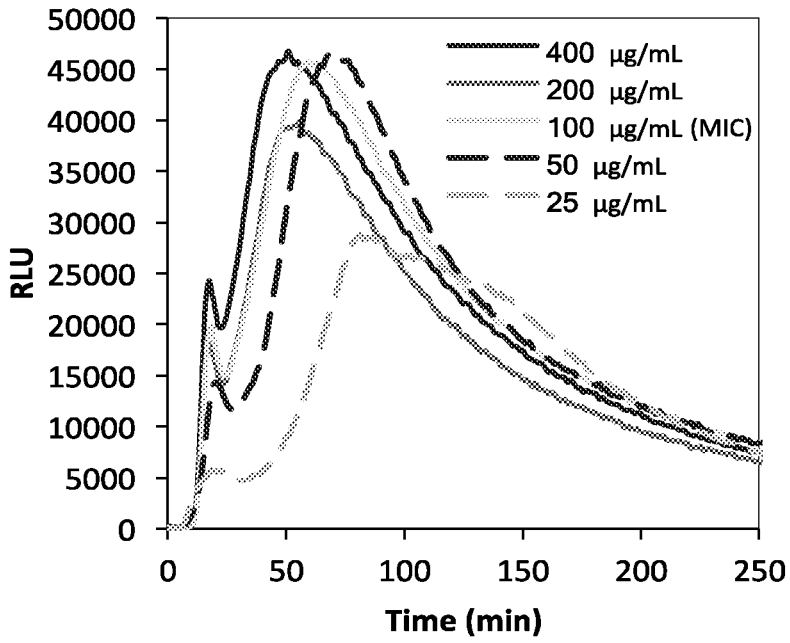
Figure 8:
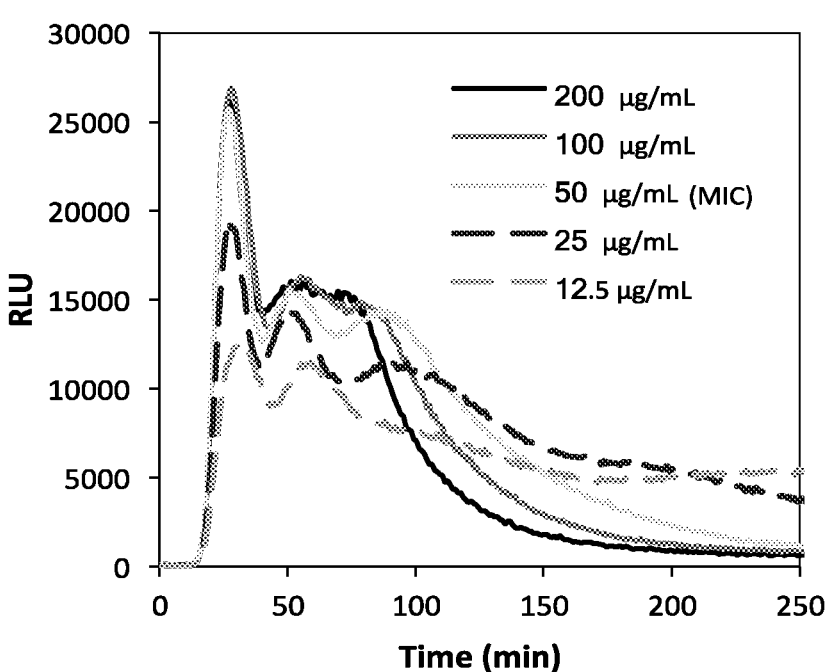
Figure 8:
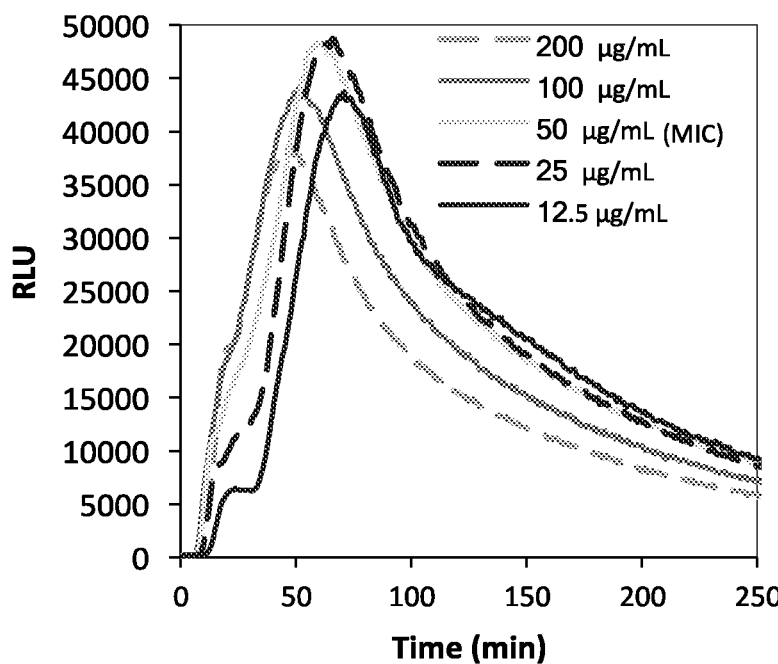
Figure 8:
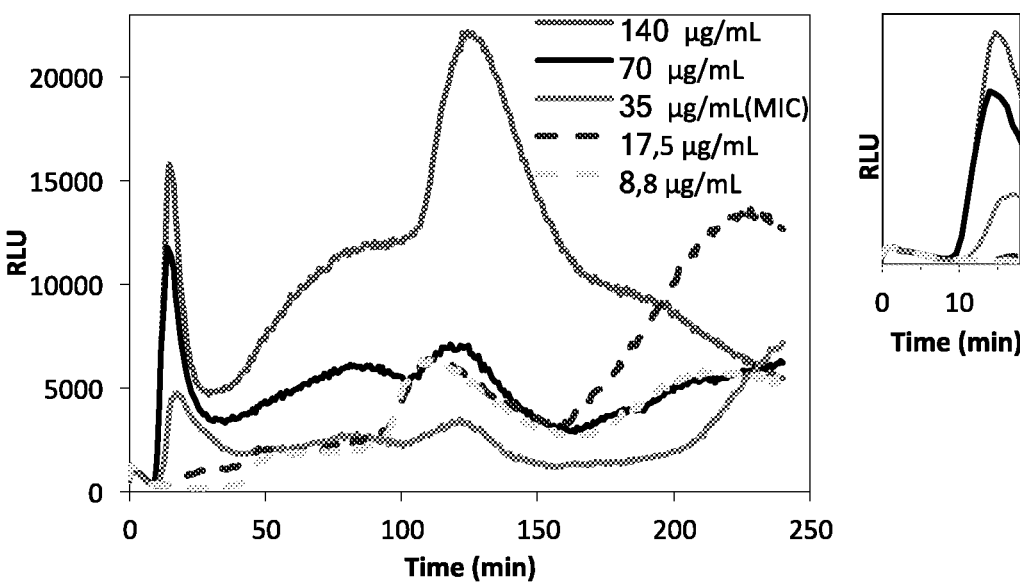
Figure 8:
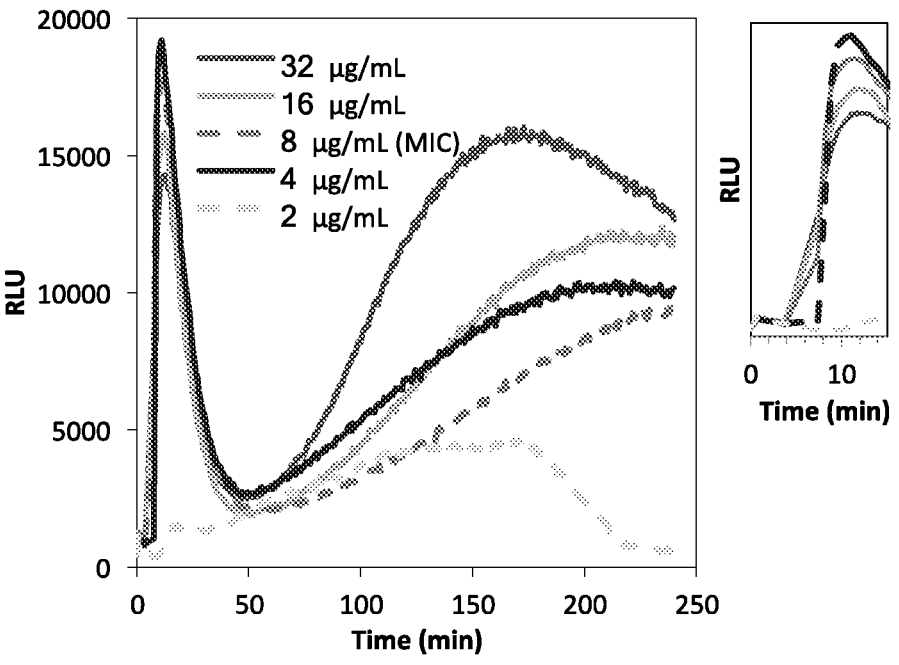
Figure 8:
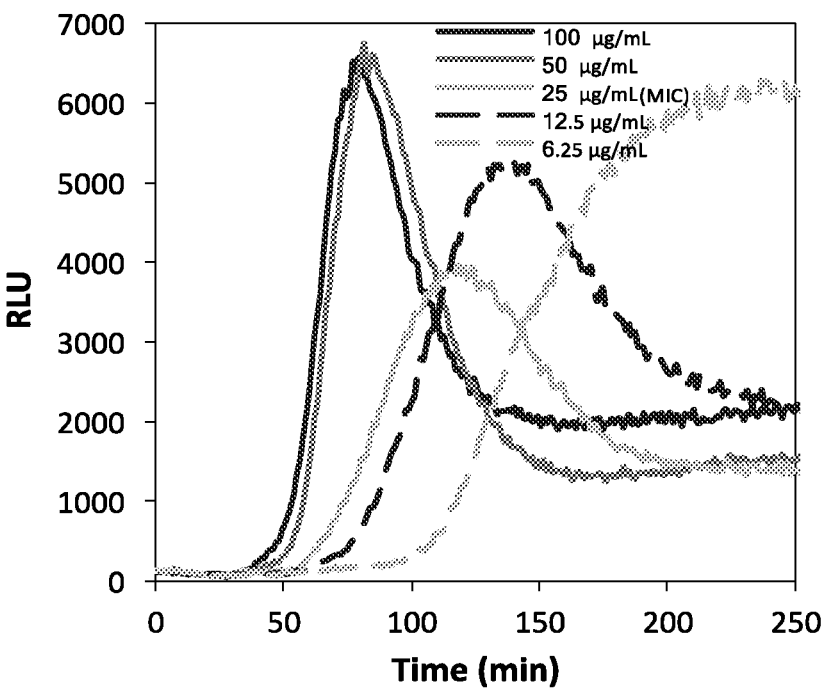
Figure 8:
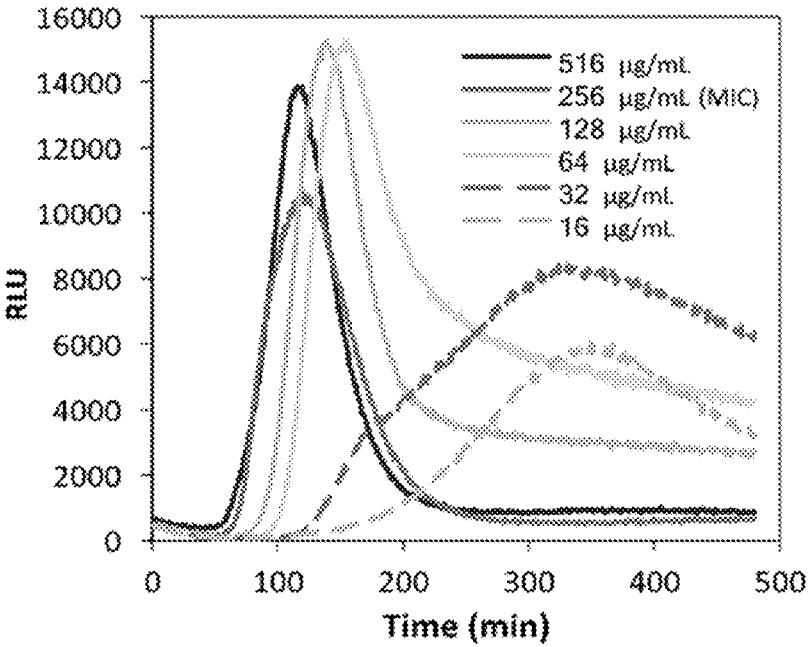
Figure 8:
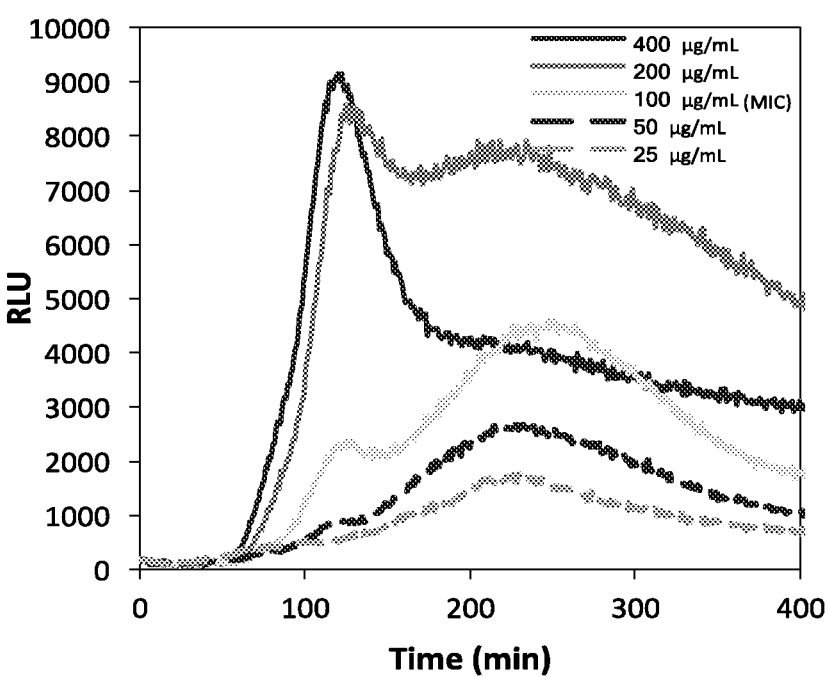
Figure 8:
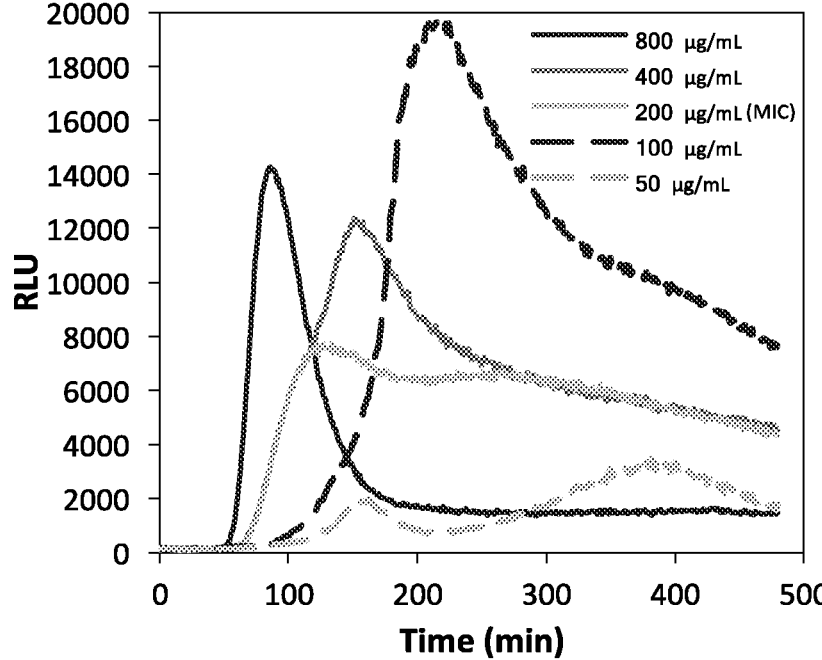
Figure 8:
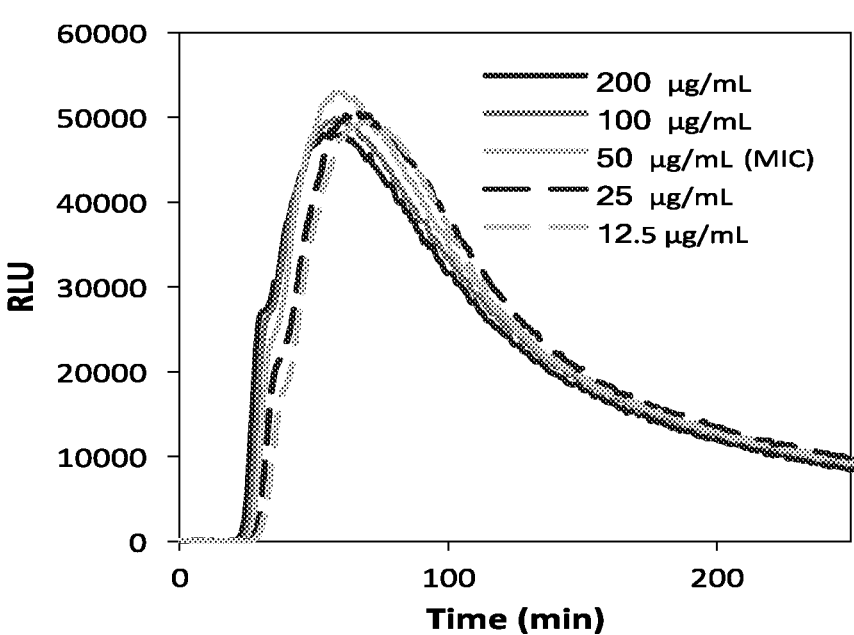
Figure 8:
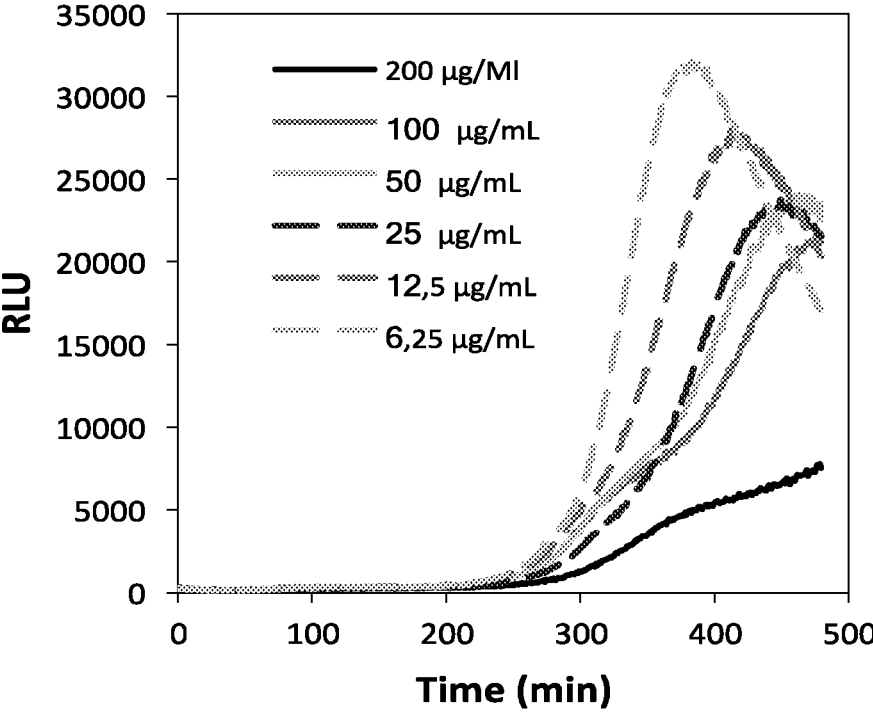
Figure 8:
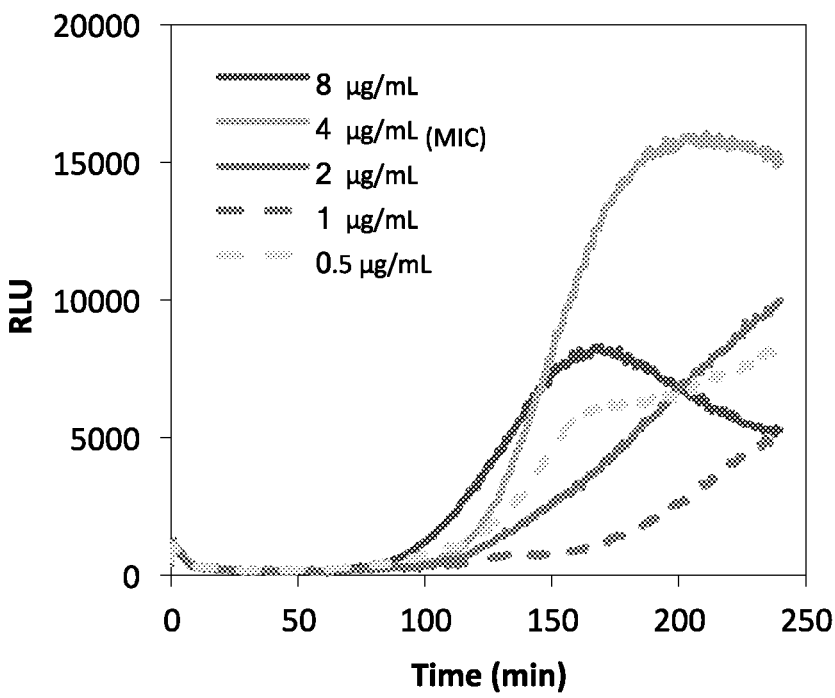

Aminoglycosides are bactericidal antibiotics causing translational miscoding with lethal consequences for the cell. Leakage of small molecules following an aminoglycoside shock was previously identified by different methods including radiolabelling. Therefore, the inventors investigated the response of live cells to aminoglycoside stress. Fast-growing cells at $OD_{600}$ of 0.3 (0.15 final) were placed into a plate reader for a short period of time for thermal equilibration and the antibiotic added at different concentrations around the MIC in LB media. Upon increasing concentrations of neomycin, a bi-phasic signal became apparent with a rapid and strong initial ATP release for concentrations above the MIC (FIG. 8). In these conditions, leakage occurred within a few minutes from the addition of the antibiotic, a result consistent with the leakage of amino-acids/nucleotides/K+ that was previously reported. Because MIC values do not report on cell viability, the inventors performed a survival assay for different neomycin concentrations (FIG. 8). The number of colonies forming units (CFU) during the first 90 minutes remained constant demonstrating that cells survived neomycin treatment during this period. Therefore, the inventors concluded that the observed bi-phasic ATP efflux was from cells that were still alive. Similar bi-phasic traces were observed for five other aminoglycosides: streptomycin, kanamycin, gentamicin, apramycin and amikacin (FIG. 8). The inventors noted for all six aminoglycosides a drop in signal intensity at or close to the MIC concentration, which correlated with a change of the kinetic of ATP release. The lag before detection of luminescence was shortening as the antibiotic concentration increased for the 6 tested aminoglycosides (Table 2).

TABLE 2

| Lag times for bactericidal antibiotics before first ATP release of the bioluminescence curves from the FIG. 8. | | |
| Antibiotic | Concentrations | Lag time before ATP |
| --- | --- | --- |
| Neomycin | 91.0 μg/mL | 9.4 |
| | 45.0 | 12.8 |
| | 22.8 (MIC in LB) | 16.3 |
| | 11.25 | 42.4 |
| | 5.6 | 48.6 |
| Gentamicin | 12.5 μg/mL | 12.9 |
| | 6.25 (MIC in LB) | 16.2 |
| | 3.12 | 30.2 |
| | 1.56 | 54.0 |
| | 0.78 | 67.1 |
| | 0.39 | 136.3 |
| | 0.19 | 136.1 |
| Kanamycin | 100 μg/mL | 8 |
| | 50 | 11 |
| | 25 (MIC in LB) | 16 |
| | 12.5 | 25 |
| | 6.25 | 50 |
| Streptomycin | 200 μg/mL | 10 |
| | 100 | 12 |
| | 50 (MIC in LB) | 16 |
| | 25 | 21 |
| | 12.5 | 39 |
| Apramycin | 54 μg/mL | 10.9 |
| | 27 (MIC in LB) | 13.3 |
| | 13.5 | 30.0 |
| | 6.75 | 60.9 |
| | 3.37 | 163.0 |
| Amikacin | 50 μg/mL | 10.5 |
| | 25 | 16.0 |
| | 12.5 (MIC in LB) | 21.6 |
| | 6.25 | 31.0 |
| | 3.125 | 42 |
| Ampicillin | 100 μg/mL | 9 |
| | 50 | 13 |
| | 25 (MIC in LB) | 23 |
| | 12.5 | 43 |
| | 6.25 | 108 |

TABLE 2-continued

Lag times for bactericidal antibiotics before first ATP
release of the bioluminescence curves from the FIG. 8.

| Antibiotic | Concentrations | Lag time before ATP |
|---|---|---|
| Cephalexin | 140 µg/mL | 3.6 |
| | 70 | 3.6 |
| | 35 | 5 |
| | (MIC in LB) | |
| | 17.5 | 9.45 |
| | 8.8 | 34.3 |
| Polymyxin B | 32 µg/mL | <2.4 |
| | 16 | <2.4 |
| | 8 | <2.4 |
| | (MIC in LB) | |
| | 4 | 2.4 |
| | 2 | 5.3 |
| Ofloxacin | 8 µg/mL | 77 |
| | 4 | 84 |
| | (MIC in LB) | |
| | 2 | 95 |
| | 1 | 105 |
| | 0.5 | — |
| Rifampicin | 100 µg/mL | 34.6 |
| | 50 | 34.8 |
| | (MIC in LB) | |
| | 25 | 38 |
| | 12.5 | 57.1 |
| | 6.25 | 63.8 |
| | 3.125 | 67 |
| Nalidixic acid | 516 µg/mL | 46.4 |
| | 258 | 50.8 |
| | (MIC in LB) | |
| | 128 | 79.1 |
| | 64 | 88.9 |
| | 32 | 114.1 |
| | 16 | 127.3 |
| Bleomycin | 400 µg/mL | 71.5 |
| | 200 | 78.0 |
| | 100 | 98.0 |
| | (MIC in LB) | |
| | 50 | 142.0 |
| | 25 | 164.0 |
| Zeocin | 800 µg/mL | 51.9 |
| | 400 | 57.8 |
| | 200 | 68.6 |
| | (MIC in LB) | |
| | 100 | 85.7 |
| | 50 | 97.5 |
| | 25 | 113.1 |
| | 12.5 | 112.2 |
| Amoxicillin | 50 µg/mL | 6.9 |
| | 25 | 8 |
| | 12.5 | 11.4 |
| | (MIC in LB) | |
| | 6.25 | 31.4 |
| | 3.125 | 39.3 |
| Cefixime | 200 µg/mL | 14.2 |
| | 100 | 14.9 |
| | 50 | 15.2 |
| | (MIC in LB) | |
| | 25 | 16.7 |
| | 12.5 | 17.5 |
| Cefoxitin | 200 µg/mL | 4.9 |
| | 100 | 4.9 |
| | 50 | 4.9 |
| | (MIC in LB) | |
| | 25 | 6.1 |
| | 12.5 | 10.9 |
| Ceftrixome | 50 µg/mL | 13.9 |
| | 25 | 16.5 |
| | 12.5 | 19.2 |
| | 6.25 | 21.2 |
| | 3.125 | 29.7 |
| Ceftazidime | 400 µg/mL | 7.8 |
| | 200 | 8.0 |
| | 100 | 8.3 |
| | (MIC in LB) | |
| | 50 | 8.6 |
| | 25 | 40.3 |

TABLE 2-continued

Lag times for bactericidal antibiotics before first ATP
release of the bioluminescence curves from the FIG. 8.

| Antibiotic | Concentrations | Lag time before ATP |
|---|---|---|
| Ciprofloxacin | 100 µg/ml | 26.4 |
| | 50 | 33.7 |
| | 25 | 39.4 |
| | (MIC in LB) | |
| | 12.5 | 52.4 |
| | 6.25 | 88.5 |
| Fosfomycin | 200 µg/mL | 18.6 |
| | 100 | 20.2 |
| | 50 | 21.8 |
| | (MIC in LB) | |
| | 25 | 26.2 |
| | 12.5 | 28.6 |

For the highest concentrations the lag shortened to incompressible values of about 9.4 min for neomycin, 4.7 min for kanamycin, 10 min for streptomycin and 10.9 min for apramycin. Below the MIC, the results should be analysed carefully. Long lags and weak signals suggest that not all cells accumulated antibiotics at the moment of the addition of the drug. Moreover, because at sub-MIC drug concentrations cells continued to grow during the test, the traces might be slightly affected by residual growth. For concentrations above the MIC, responses were clear and displayed similarities indicating that most of the cells were affected very rapidly after drug contact (FIG. 8). The signature observed for these miscoding agents i.e. a first rapid and strong burst followed by a slow but large phase was clearly identifiable at MIC concentrations.

Ampicillin is a beta-lactam bactericidal antibiotic rapidly inhibiting cell wall synthesis, which leads to slow cell lysis. Addition of increasing concentrations of the drug shortened the lag to 9 min before ATP release. Similarly, to miscoding agents, concentrations above the MIC (25 µg/ml) gave strong and clear signatures (FIG. 8). Here ATP release was multiphasic with an initial phase of very weak intensity that preceded a second one of about 2 hours of much larger amplitude.

Polymyxins are bactericidal antibiotics mostly acting on Gram-negative bacteria by altering membrane permeability. Polymyxin B triggered a clear and strong bi-phasic response even at a concentration twice below the MIC (4 µg/ml). A strong and rapid initial phase occurred after the addition of the drug with a subsequent second phase also of large amplitude. Above the concentration of 4 µg/ml, ATP release started immediately (lag shorter than 2.4 min and not measurable) after the addition of polymyxin B (FIG. 8). Interestingly the amplitude of the initial burst was maximal for a dose of 4 µg/ml and progressively decreased for higher concentrations (FIG. 8). On the contrary, the amplitude of the second phase increased with concentration (FIG. 8).

Addition of cephalexin, a beta-lactam bactericidal antibiotic of the cephalosporin family, triggered a multiphasic response (FIG. 8). Sub-inhibitory concentrations of 8.8 and 17.5 µg/mL resulted in 3 synchronized phases during the 50-250-minute period. At 35 µg/mL, an initial burst was detectable that increased in amplitude for higher concentrations and was reminiscent of the initial burst detected for miscoding agents as well as ampicillin and polymyxin B. Contrarily to polymyxin B, the amplitude of the initial burst increased with concentration (FIG. 8) after an incompressible lag of 3.6 min (FIG. 8). The amplitudes of the 3 synchronized phases that followed during the 50-250-minute period varied.

Ofloxacin belongs to the fluoroquinolone family and inhibits the bacterial DNA gyrase preventing DNA replication in growing bacteria. It is a bactericidal antibiotic. Its action on ATP release was rather slow since the efflux was observed after a lag of 77 minutes at the highest concentration tested (FIG. 8 and Table 2). The ATP release seemed monophasic and its amplitude varied with the concentration of the drug used.

Data on bactericidal antibiotics tested are summarized in FIG. 10A. In conclusion, for all bactericidal antibiotics tested, the inventors observed mono or multiphasic phases of ATP leakage.

These data have been confirmed by performing novel assays following the same experimental conditions as those disclosed above. The results of these assays are summarized on FIG. 10B and confirm the ability of the method according to the invention to rapidly identify bactericidal compounds.

Bacteriostatic Antibiotics are Poor Stimulator of ATP Leakage

Figure 9:
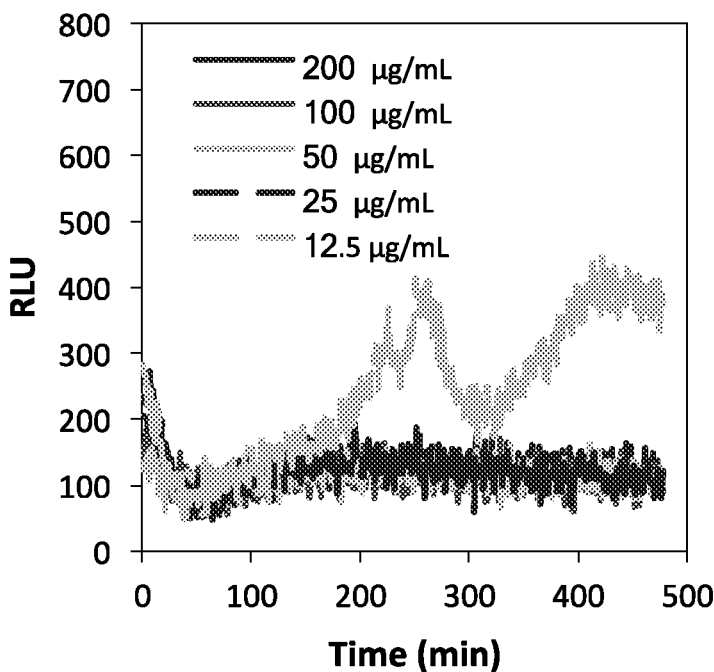
FIG. 9. Bacteriostatic antibiotics did not trigger ATP release when used at concentrations where they are not bactericidal. Representative traces of bioluminescence measurements obtained at 37° C. with *E. coli* reporting cells in LB growth media following the addition of antibiotics. MIC values are indicated. Some bacteriostatic drugs gave strong signal only when used at high dose which was then lethal.
Figure 9:
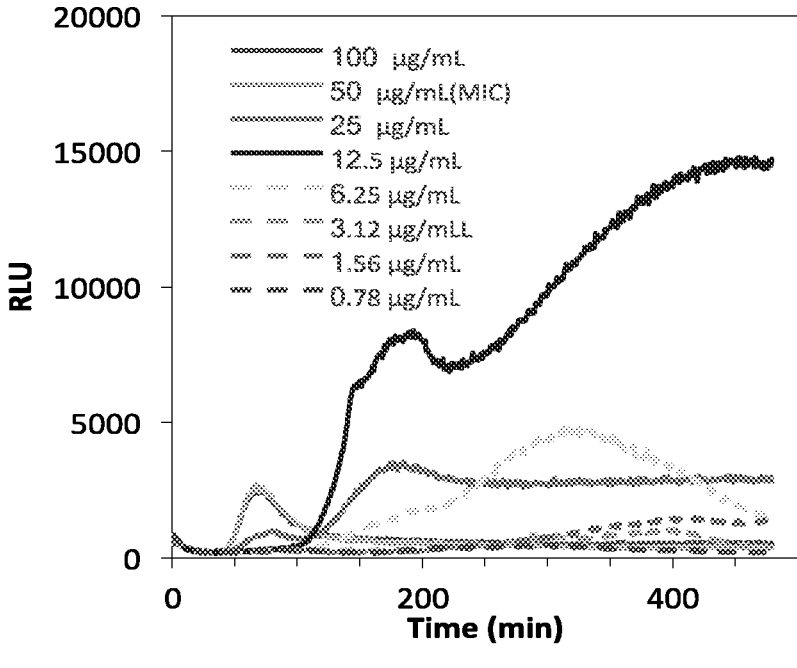
Figure 9:
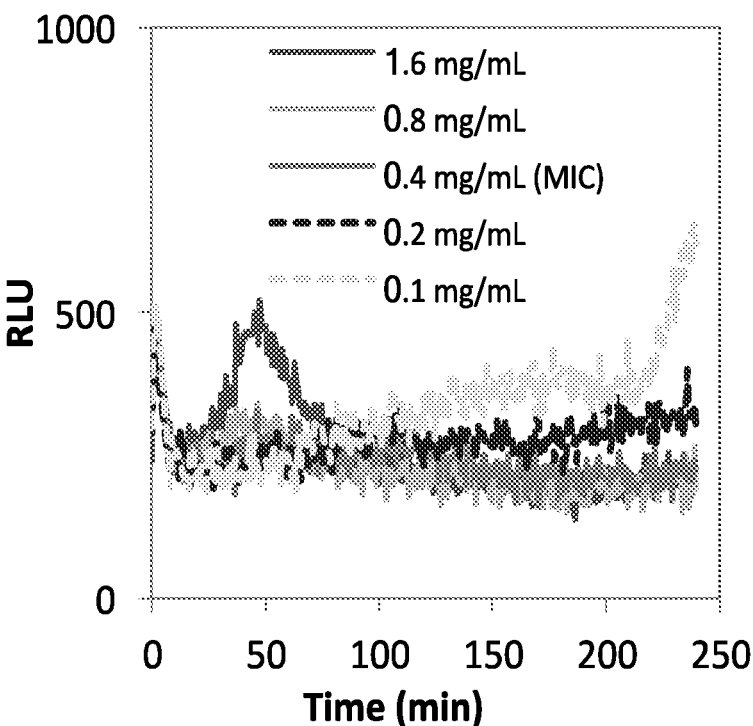
Figure 9:
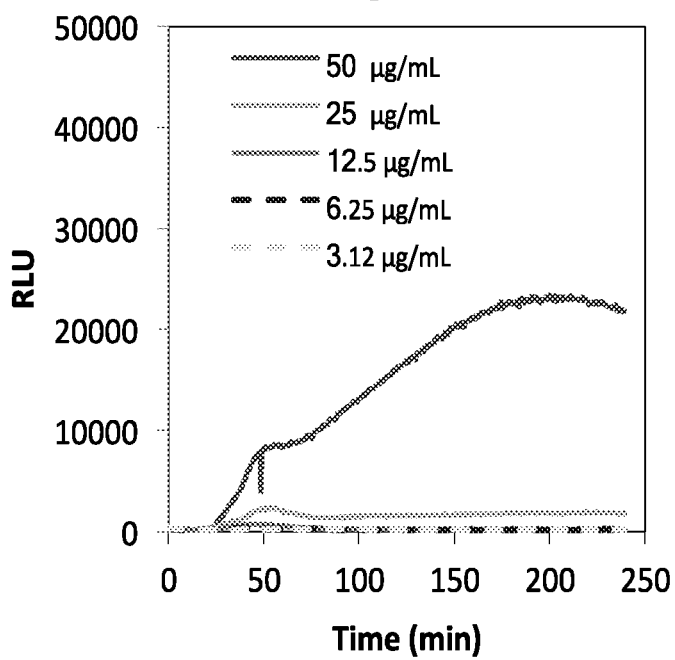
Figure 9:
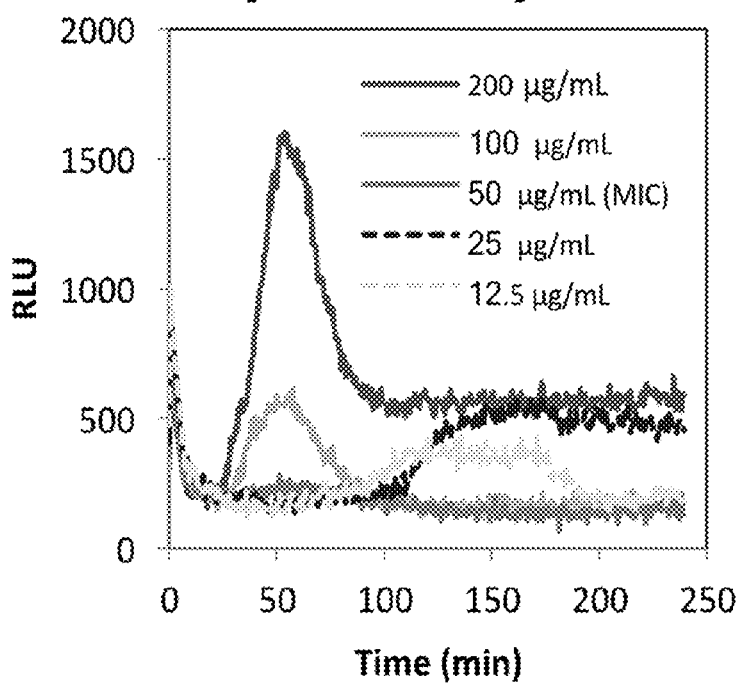
Figure 9:
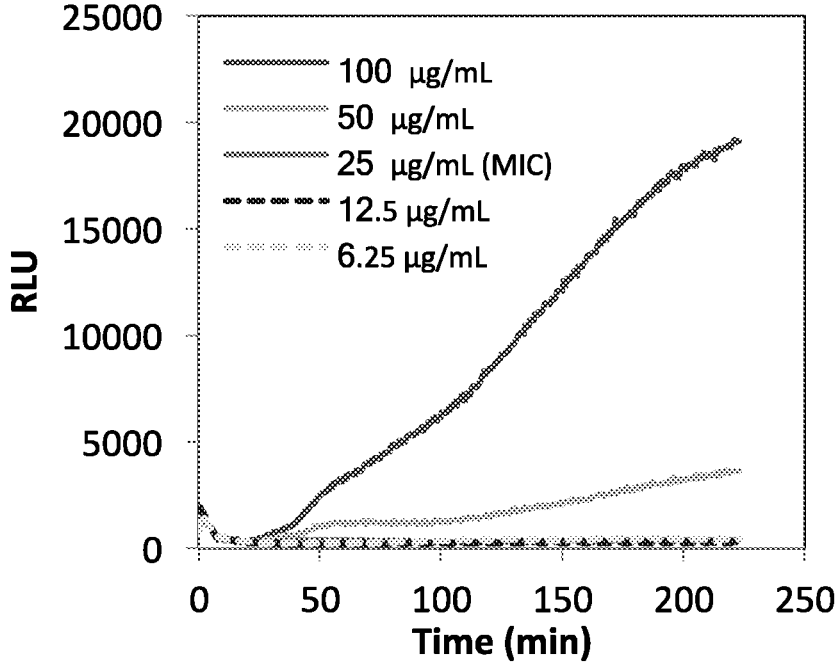
Figure 9:
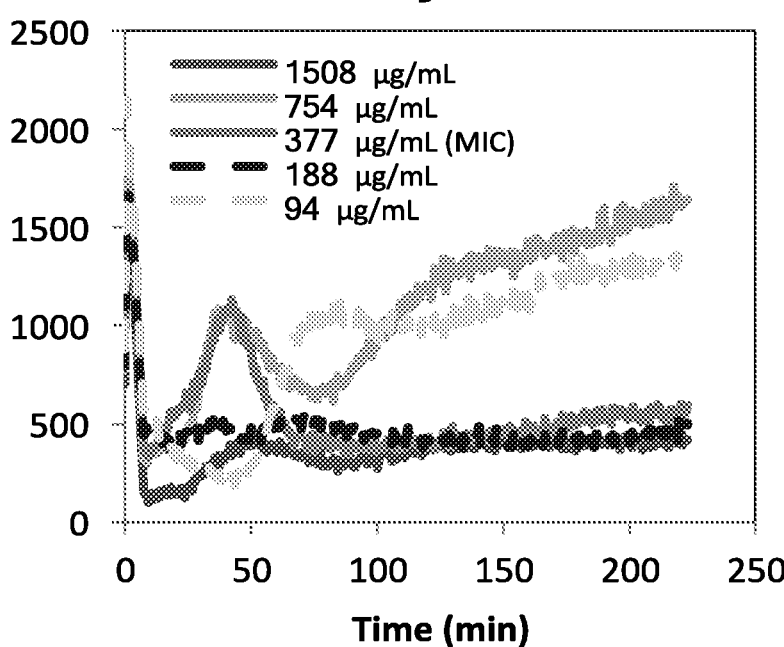
Figure 9:
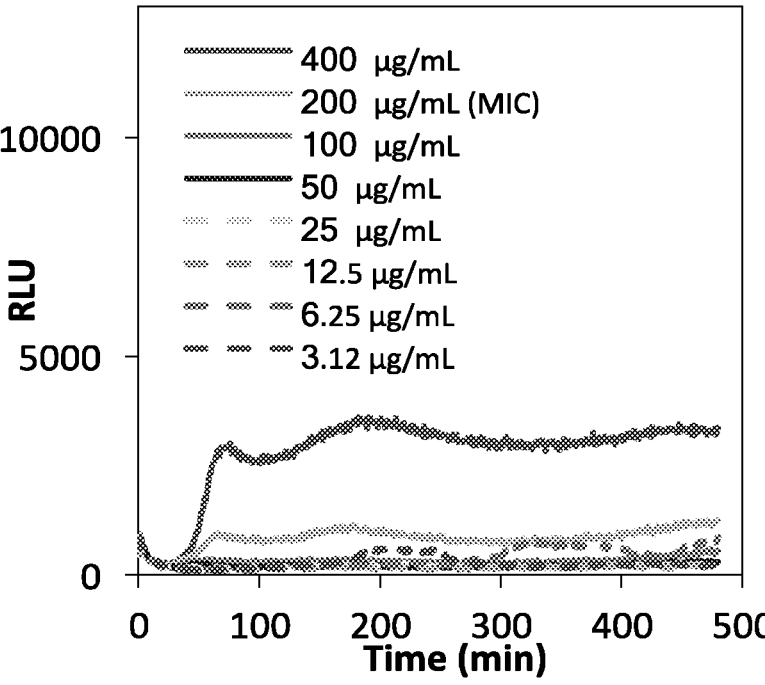
Figure 10:
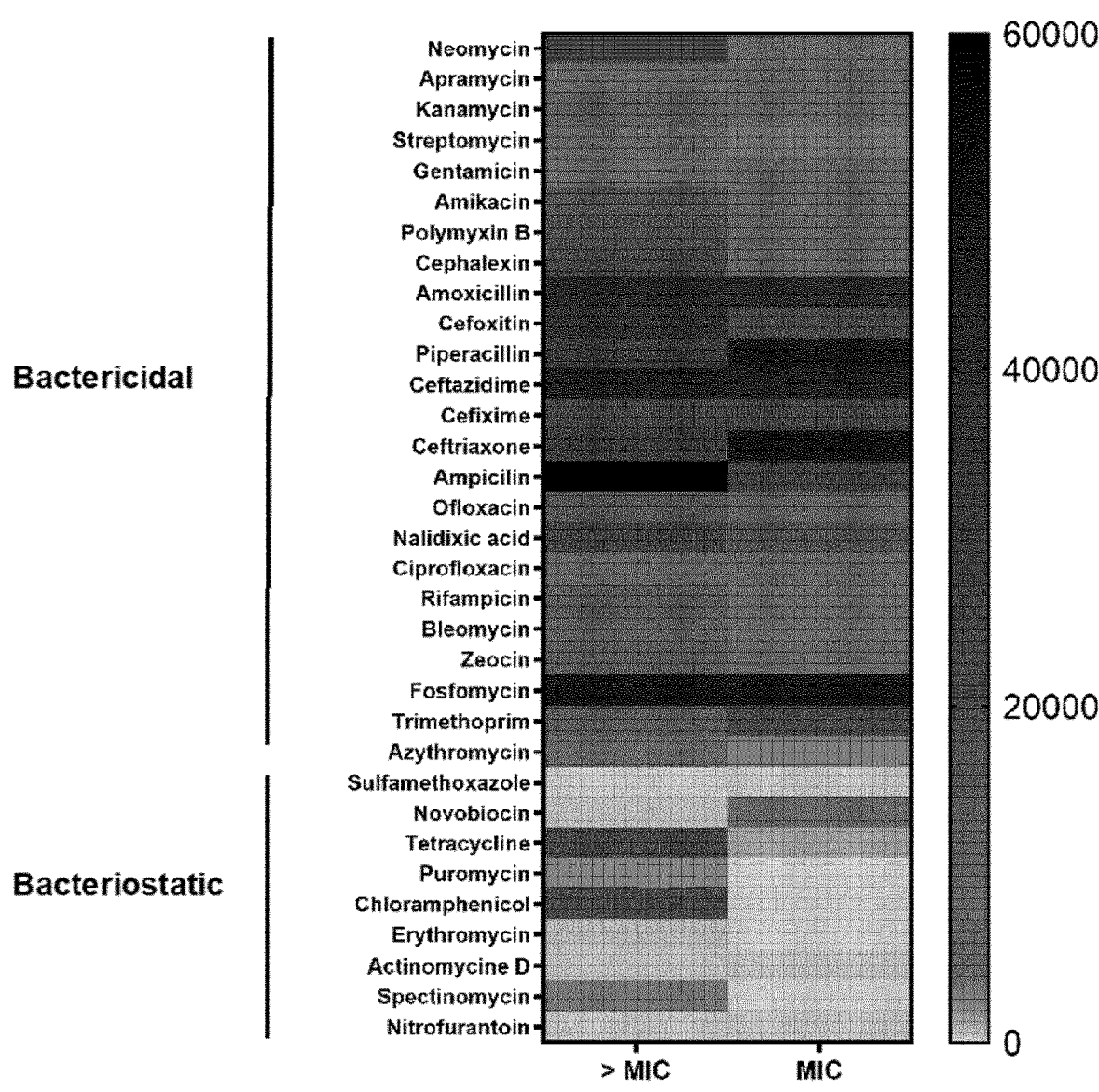
FIG. 10. A, Synthesis of the results shown on FIGS. 8 and 9. Leakage of ATP as a key signature of the attack by bactericidal antibiotics. A universal signal (dark grey) was detected for bactericidal antibiotics when they reacted with sensitive MG 1655 *E. coli* cells. This signal was absent or very weak (light grey) for bacteriostatic antibiotics. B, Heatmaps synthesizing results of analyses of bactericidal and bacteriostatic antibiotics. Maximal amplitudes of bioluminescence signals were collected during the first 4-hour period with drug at (MIC) in LB and MOPS-G or above the MIC in LB (>MIC). Signal's intensity is indicated by color intensity on a scale from strong (dark gray) to absent or very weak (light gray). Done on GraphPad Prism 8.0.1.

The inventors next investigated several bacteriostatic antibiotics that inhibit protein synthesis. Erythromycin and spectinomycin, antibiotics that target the ribosome triggered an ATP release of very weak amplitude. This is no comparison with what the inventors observed for bactericidal drugs (FIGS. 9 and 10). For tetracycline and azithromycin that also target the ribosome, it was only at a high dose of 4 and 2.5 times the MIC, respectively that ATP release was observed (FIG. 9). For puromycin, another bacteriostatic drug targeting the ribosome, very weak leakage was observed at sub-MIC concentrations (FIG. 9). Signals measured for concentrations above the MIC could be underestimated as puromycin inhibited the bioluminescence assay at these concentrations (FIG. 5b). Exposure to high concentrations of chloramphenicol, twice or four times the MIC, resulted in important leakage that seemed linear with time (FIG. 9). This is reminiscent of what the inventors observed with tetracycline and azithromycin. Rifampicin is a transcription initiation inhibitor, which triggers rapid mRNA decay with bacteriostatic consequences for *E. coli*. The inventors observed weak ATP leakage with a lag of about 30 minutes. Signal became stronger for a concentration above the MIC (50 µg/mL). Below the MIC traces were monophasic (FIG. 9).

The inventors concluded that bacteriostatic antibiotics, when used at a concentration where they have bacteriostatic activities, triggered very weak ATP efflux. The ATP leakage observed for bactericidal drugs is therefore a key signature of the lethal action of the drugs (FIG. 10).

Bactericidal Antibiotics Stimulate ATP Release in Minimal Growth Media

The inventors performed the ATP release assay in minimal media. Cells in exponential phase of growth were used.

Figure 11:
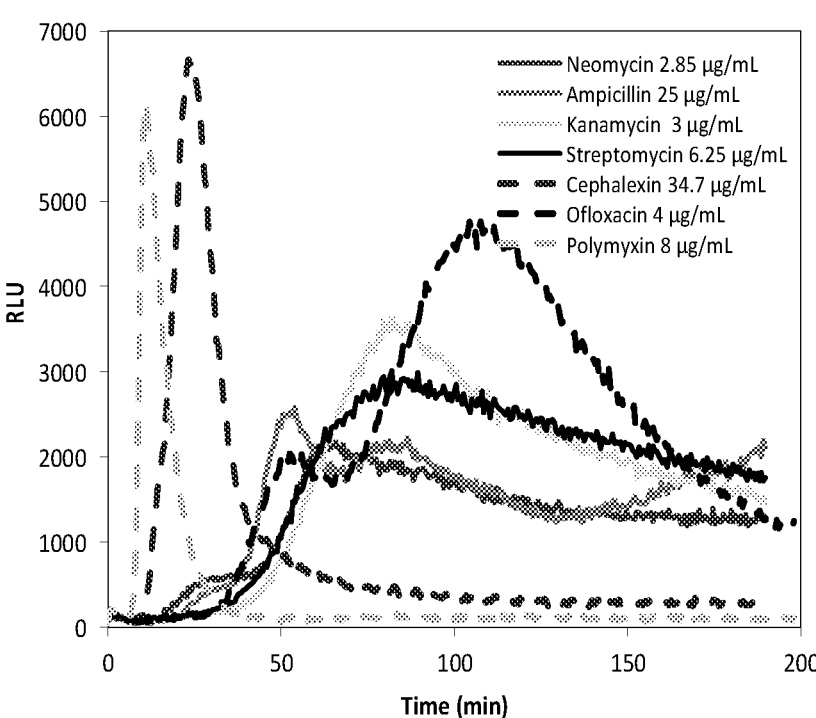
FIG. 11. Bioluminescence assay in minimal growth media at 37° C. A, ATP release of *E. coli* grown in MOPS minimal medium (glucose 0.4%) in presence of a set of antibiotics bactericidal (left), bacteriostatic (right) at their respective MIC. B, complete set of traces for gentamicin, neomycin, apramycin (bactericidal) and rifampicin, azithromycin (bacteriostatic). Azithromycin stimulated a ATP leakage at its highest concentration (400 µg/mL) in agreement with what is observed in rich media (FIG. 9).
Figure 11:
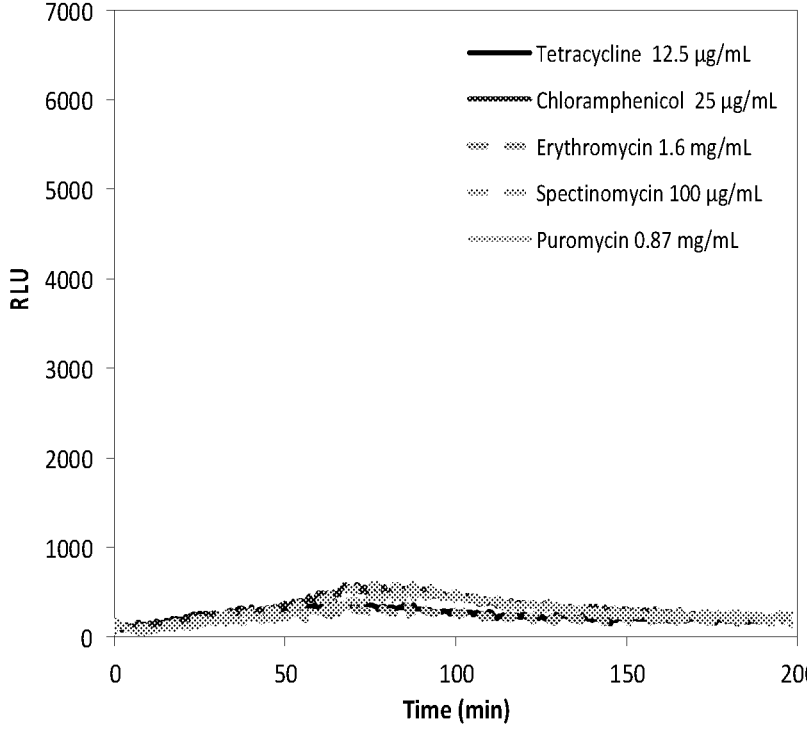
Figure 11:
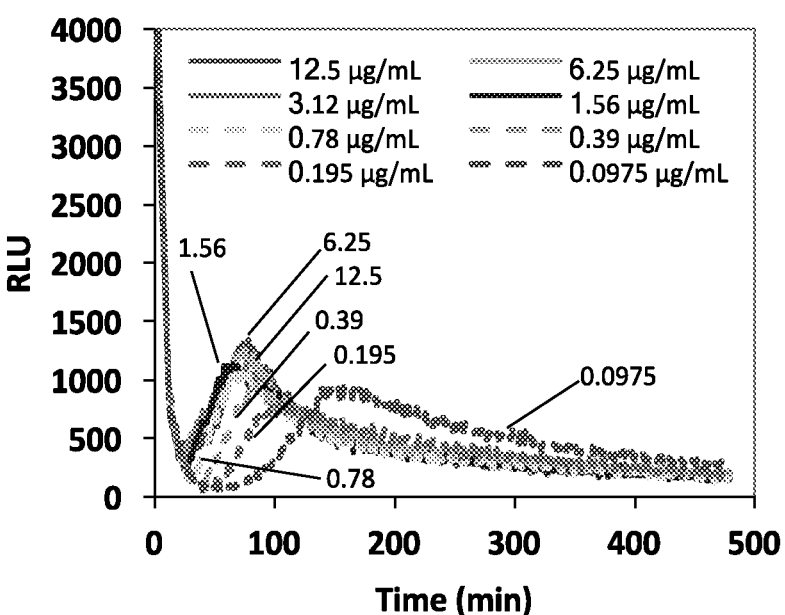
Figure 11:
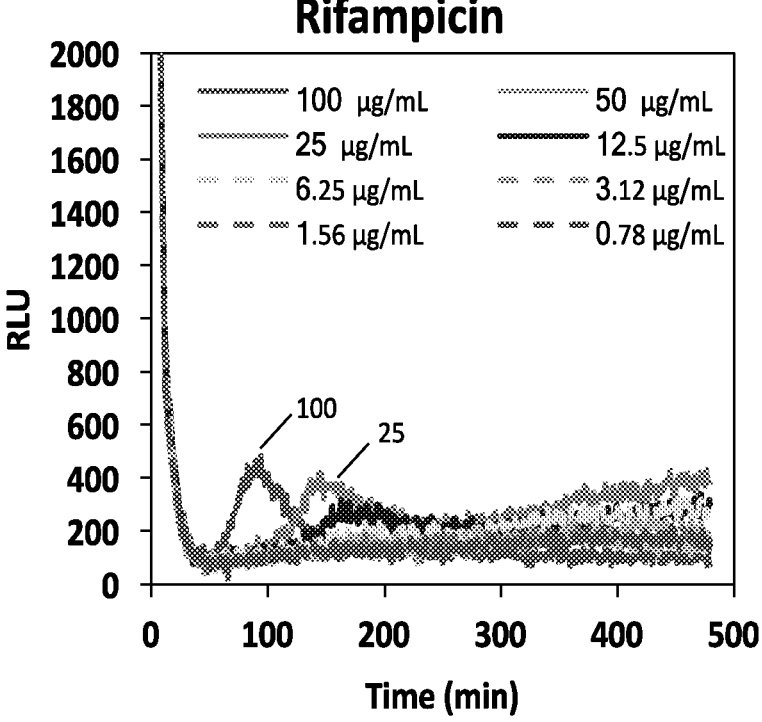
Figure 11:
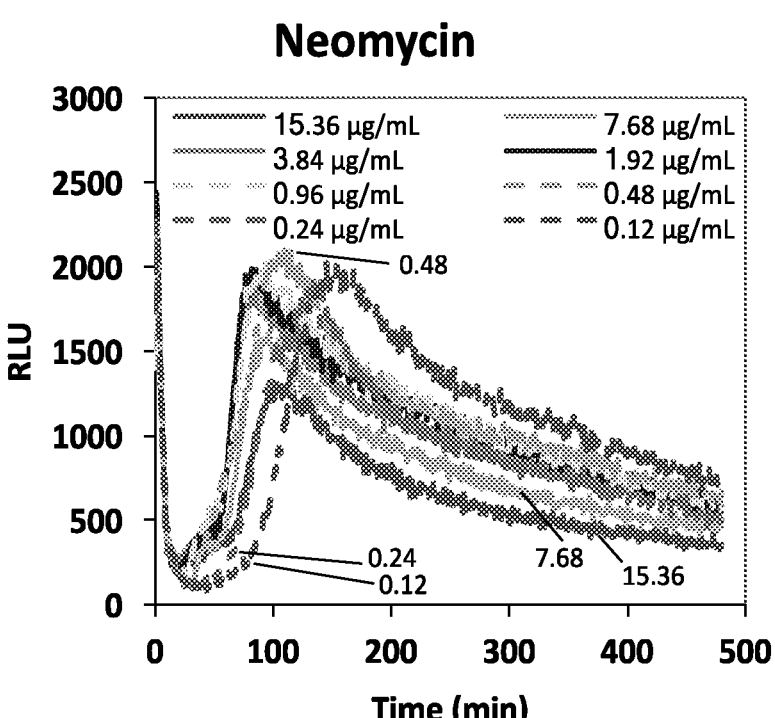
Figure 11:
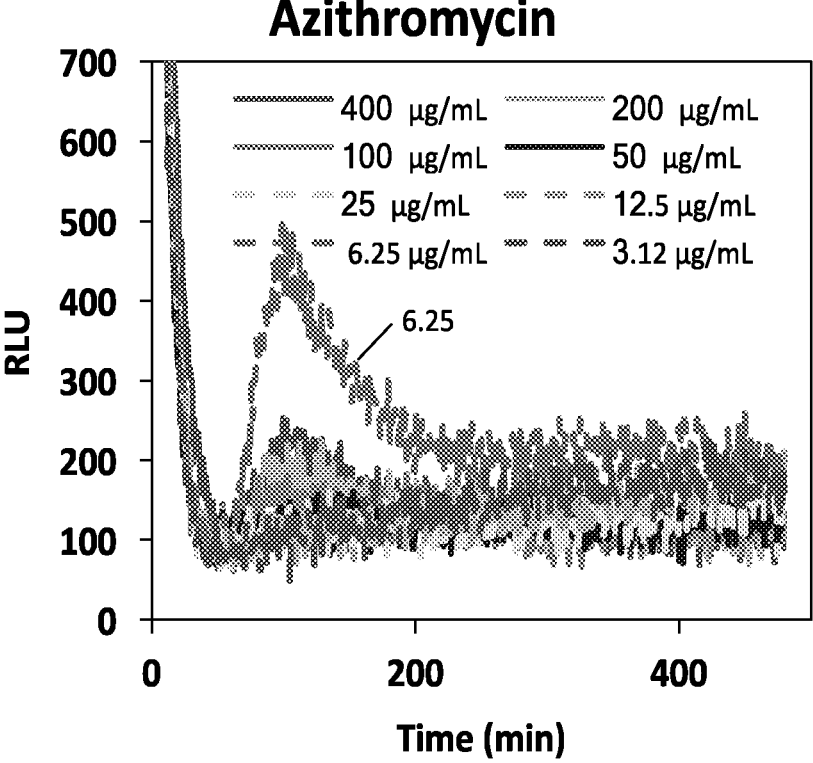
Figure 11:
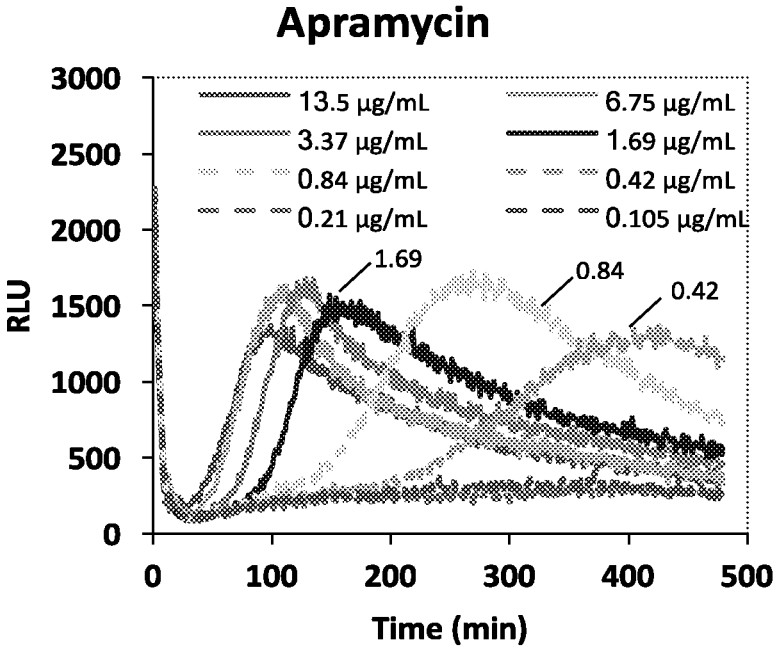

ATP release was monitored at MIC values, or for serial dilutions of antibiotics (FIG. 11). Overall for all antibiotics, the intensities of ATP release signals were weaker in minimal medium compared to rich medium. For instance, ampicillin and polymyxin had values decreased by a factor 10 and 3, respectively. As described above, the assay was found to be more sensitive in minimal medium for detecting ATP. This result indicated that ATP leakage was less pronounced in minimal medium. The inventors also noted monophasic traces for polymyxin and cephalexin, which contrasted with the biphasic or multiphasic traces observed respectively for these drugs in rich medium. This observation holds true for aminoglycosides, neomycin, gentamicin or apramycin (FIG. 11). The lag times of ATP release were unchanged or slightly increased except for ofloxacin for which it decreased by a factor 2 (FIG. 11). The inventors concluded that the observation of ATP leakage for bactericidal antibiotics in rich medium holds true for minimal medium.

ATP Leakage Assay Dedicated to the Identification of Bactericidal Compounds

Figure 19:
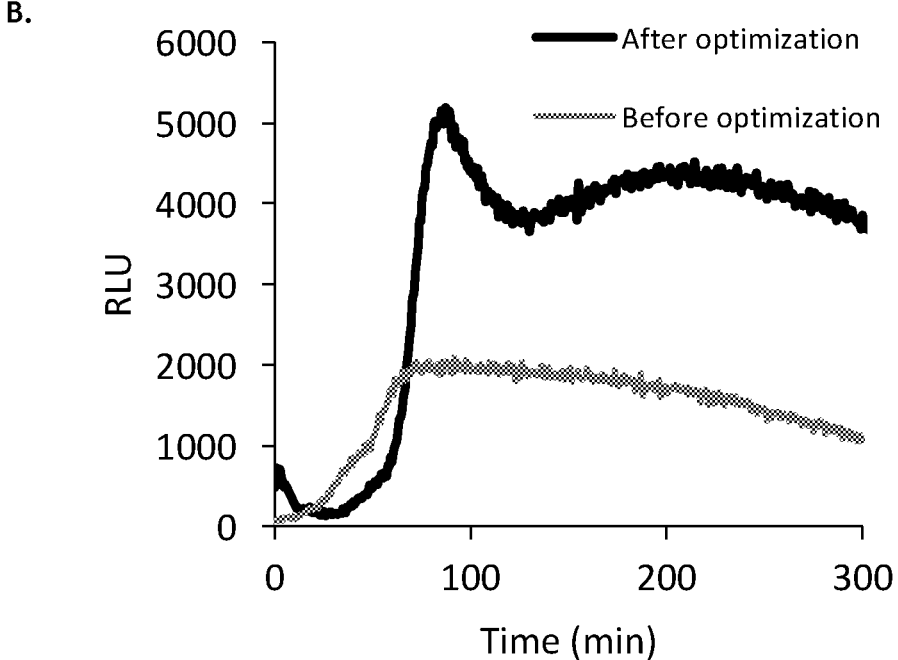
FIG. 19. Bioluminescence assay for detecting the presence of bactericidal compounds within culture supernatants of drug producers. A, Principle of the method applied to the supernatant of drug producers. B, Optimization of the assay with filtration of the supernatant as shown in FIG. 16*b*. Bioluminescence was monitored during 4 hours at 37° C. C, Test with the optimized protocol, of duplicates of the supernatants of cultures of *Streptomyces fradiae*. Bioluminescence signals were detected for the neomycin producer wild-type strain ATCC of *Streptomyces fradiae* but not for the non-producer multi-mutated strain (DSM41550) or the single-mutated strain (Δneo6).
Figure 19:
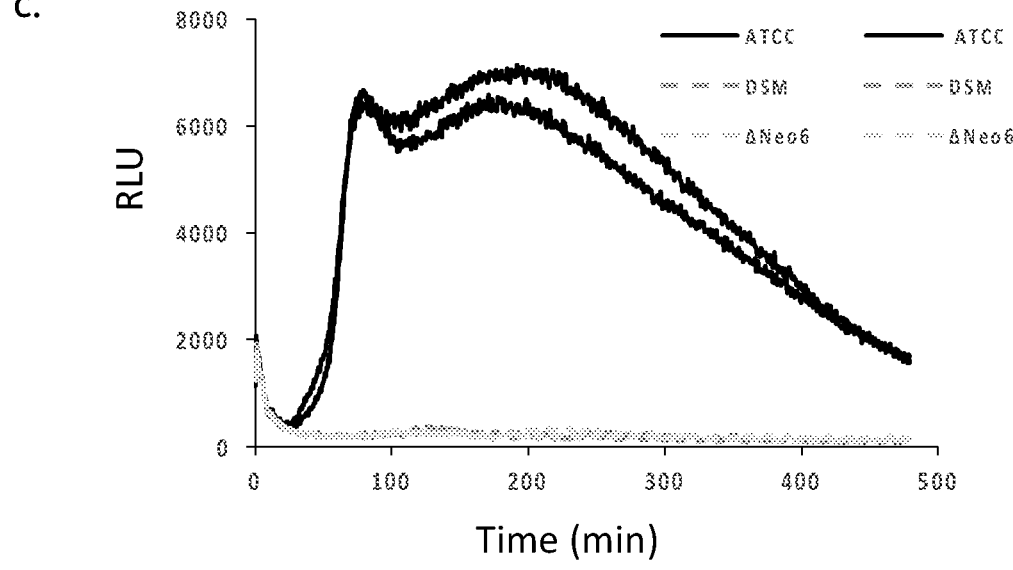

It is well known that *Streptomyces* are able to produce a large number of secondary metabolites, especially antibiotics. Bacteria of the genus *Streptomyces* provide approximately 60% of antibiotics used in modern medicine. The goal of the present invention was to develop an assay that can be performed with different medically relevant reporter strains such as pathogens, multidrug resistant bacteria or bacteria forming biofilms. In order to test whether *Streptomyces* bacteria can produce antibiotics detectable with herewith described test, the inventors used the bacterium *Streptomyces fradiae*, a neomycin producer and the reporter bacterium *Escherichia coli* (FIG. 19).

Figure 12:
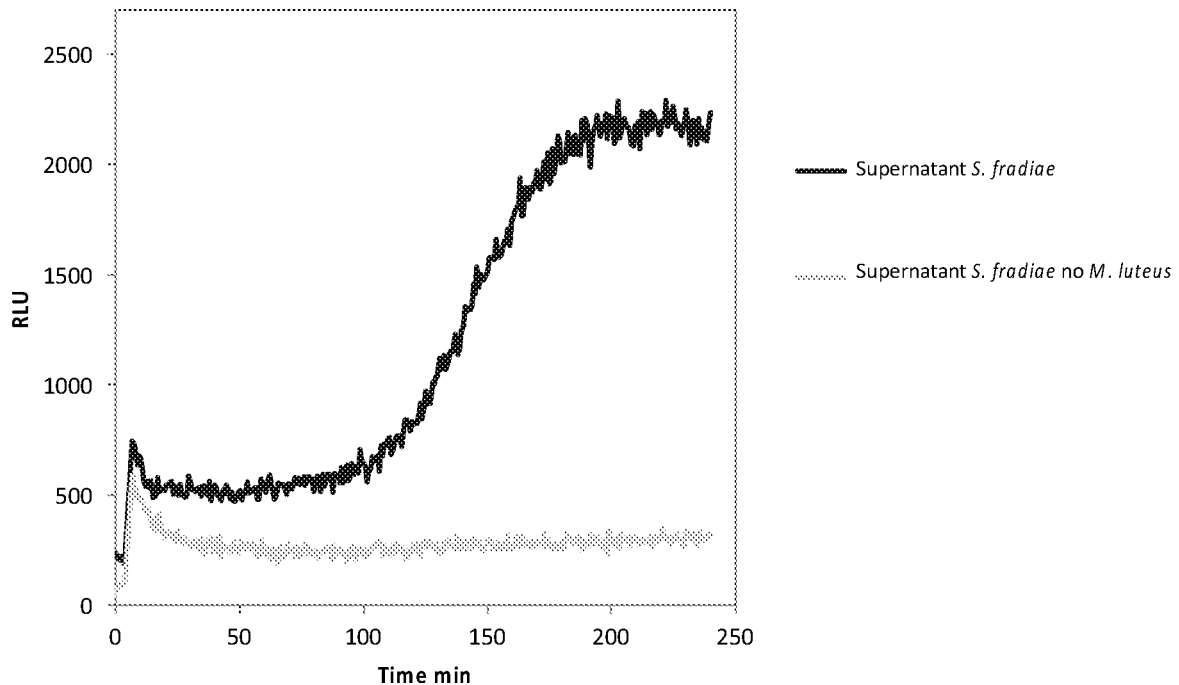
FIG. 12. The presence of neomycin in supernatants of *Streptomyces fradiae* is detectable with a Gram-positive reporter strain *M. luteus*. ATP release at 37° C. of *M. luteus* grown in LB medium in presence of a supernatant of *S. fradiae* cultivated 4 days. ATP leakage was absent in the control experiment where reporter cells *M. luteus* were absent.

The inventors also verified that the reporter strain *M. luteus* (Gram positive) could be used (FIG. 12). Cultures of producers were performed in triplicate. The aim was to produce a robust assay to test sizable libraries of chemical components or of bacteria, cyanobacteria and fungi, using only their culture supernatants. When adding the supernatant of culture of *Streptomyces fradiae*, a strong monophasic signal of ATP leakage (FIG. 13) was measured. However, without any reporter bacterium, a significant signal was also observed. The same observation was made with supernatants of two mutants of *Streptomyces fradiae*, the non-producer multi-mutated strain (DSM41550) or the single-mutated strain (Δneo6) (data not shown). This result showed that the initial protocol should be optimized when testing supernatants since some of its components reacted with the luminescence reagents to produce light.

Assay Optimization

Further investigations showed that it was the rich medium (LB or TSB) used in the preliminary measures that reacted with the supernatant, generating a false positive signal in absence of reporter bacteria (FIG. 14). Replacing rich medium LB (or TSB) with a minimal medium MOPS-glucose 0.4%, eliminated this false positive signal (FIG. 15). It is likely that components within the rich LB medium catalyzed the production of ATP from precursors or made available ATP molecules to react with the luciferase-luciferin reagents.

Figure 16:
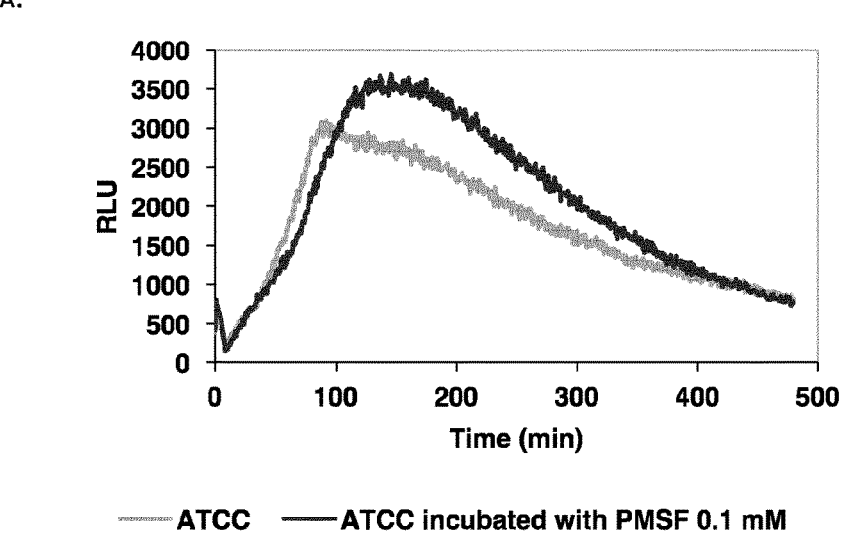
FIG. 16. Optimization of the assay A, Effect of a previous incubation of the supernatant with PMSF (concentration 0.1 mM). 0.2 µL of PMSF dissolved in absolute ethanol was added to 19.8 µL of *Streptomyces fradiae* supernatant. The mix was incubated during 20 minutes at room temperature. After incubation, tubes were put on ice until microtiter plate filling. Bioluminescence was monitored at 37° C. during 8 hours. B, Effect of ultrafiltration with a membrane (cutoff 5000 Da). Supernatants were filtered by an ultrafiltration device (VivaSpin™ 500 GE HealthCare). Before filtration, membranes were rinsed with a buffer medium (MOPS-glucose 0.4%). Supernatants were placed in concentration chamber. Concentration chamber and collector tube were centrifuged for 20 minutes at 15 000 g. Filtrate was collected and stored at –20° C.

Next, adjustments were made in order to increase the sensibility of the test, which enabled to detect the presence of bactericidal components at a sub-MIC concentration. Adjusted parameters were: $OD_{600}$ and volume of the reporter cells, volume of the bioluminescence reagents, total volume of the assay. The inventors also managed to reduce the total volume. As a non-motile bacterium, *Streptomyces fradiae* produces many extracellular proteases to survive in the environment. Moreover, given that these proteases are produced in a variable way, the inventors chose to dispose of the proteases in the supernatant to eliminate this source of variability and to improve the sensibility as proteases may degrade the luciferase. First, the inventors intended to inhibit the action of the proteases with phenylmethanesulfonyl fluoride (PMSF), a serine protease inhibitor. Indeed, *Streptomyces fradiae* can produce serine proteases. Addition of PMSF did not show any significant improvement in the results (FIG. 16). The inventors conclude that other proteases (not only serine proteases) and/or other molecules in the supernatant disrupted signal acquisition.

Figure 17:
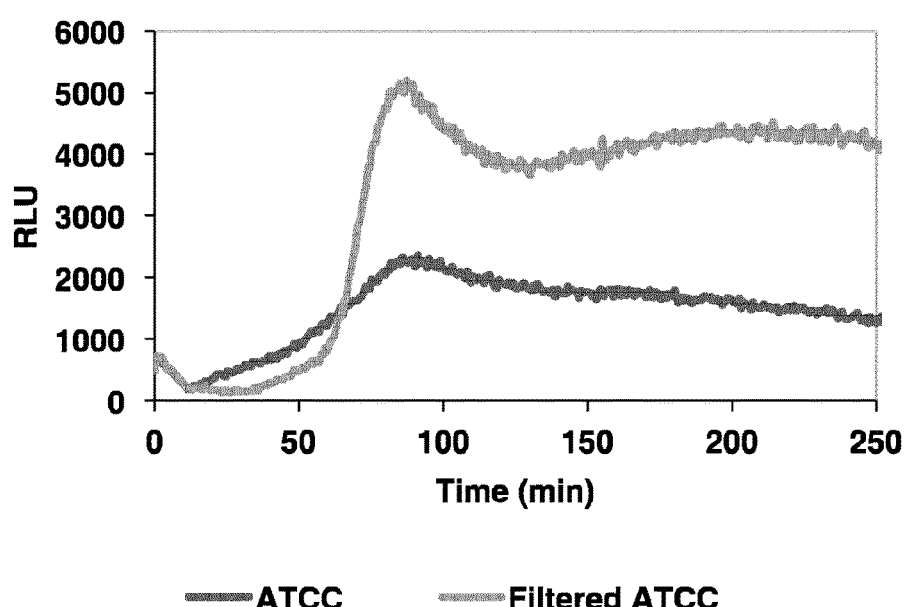
FIG. 17. Bioluminescence assay in minimal growth media at 37° C. for ATP release by *E. coli* cells grown in MOPS minimal medium (glucose 0.4%) in presence of increasing concentrations of neomycin. ATP leakage was slightly delayed compared to the traces of neomycin obtained in FIG. 8. The characteristic biphasic kinetic, which was absent in minimal MOPS-glucose medium was observed here because the serial dilution of the antibiotic performed in TSB media to match the conditions used with the supernatants.
Figure 17:
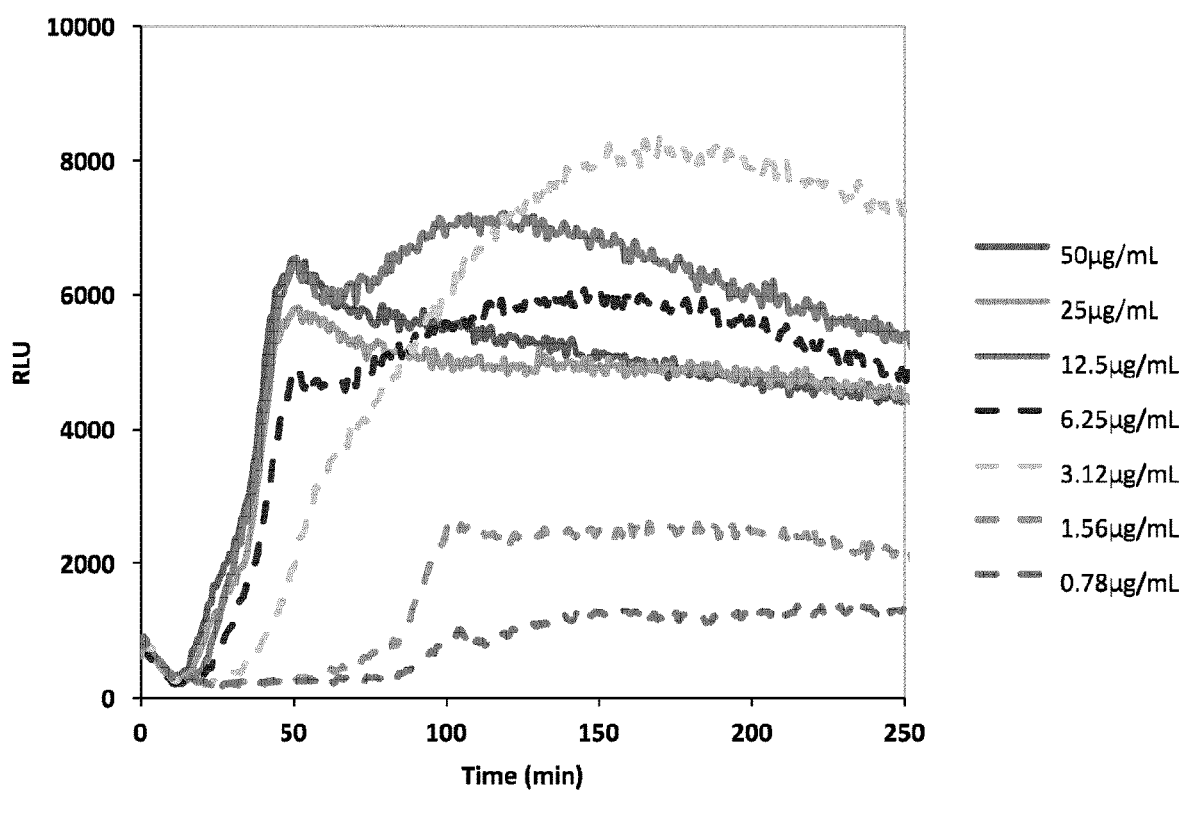
Figure 18:
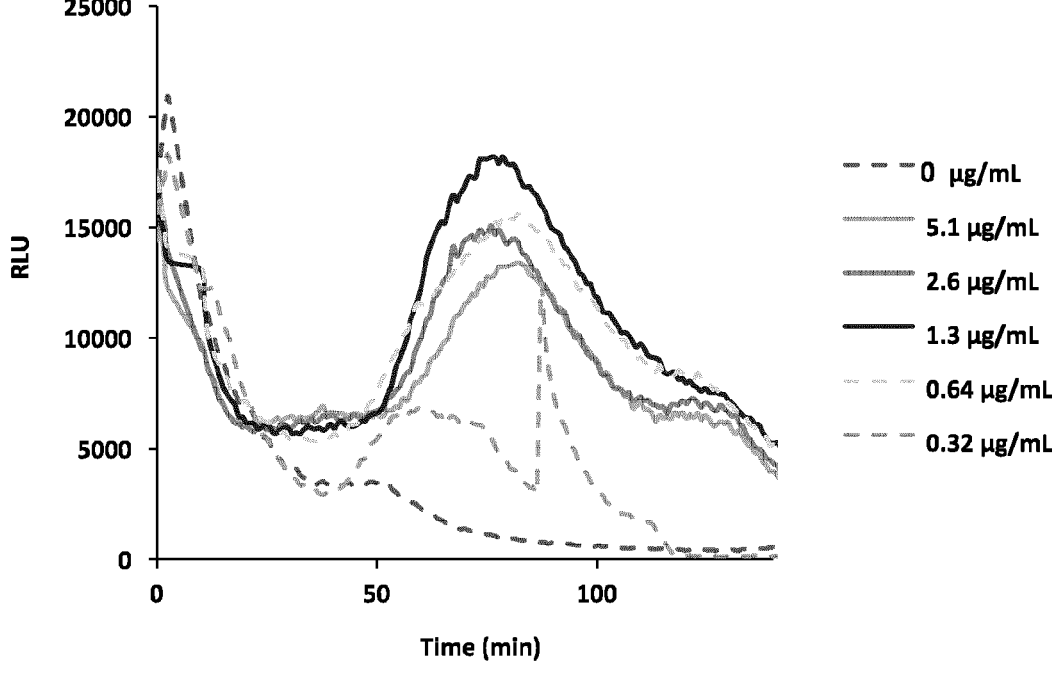
FIG. 18. Bioluminescence assay in 384-well microtiterplate. ATP release of *E. coli* grown in MOPS minimal medium (glucose 0.4%) in presence of increasing concentrations of neomycin. The assay was performed at 37° C. on a reduced volume in white 384-well microtiterplates.

To counter the protease-induced negative effects on the measurement of secondary metabolites produced by *Streptomyces fradiae*, the inventors filtered the supernatant with a membrane having a cutoff of 5 000 Da. When filtering the supernatant, two main observations need to be underlined (FIG. 16). First, the inventors obtained a two-fold increase in the signal when the supernatant of the neomycin producer was filtered. In addition, the pattern observed when the supernatant was filtered was somewhat reminiscent of the pattern observed with pure neomycin; a bi-phasic signal with strong initial ATP release but with slower kinetics (FIG. 16). The observed delay originates from the rich TSB media (FIG. 17). The inventors concluded that filtration allowed the elimination of proteins and large molecules, which were interfering with the performance of the assay. The volume of the assay was decreased further to 9 µL in 384-well microtiter plates without loss in sensitivity (FIG. 18). Through modification of the medium, diminution of the volume and use of filtration, the inventors succeeded in offering a technique with great sensibility, enabling to detect and identify the bactericidal component neomycin in *Streptomyces fradiae* supernatant.

The Assay Detects Variability in *Streptomyces Fradiae* Production of Secondary Metabolites To be sure that the herewith described test was robust enough for a high-throughput screening, the inventors tested supernatants from mutants of *Streptomyces fradiae*, which were not able to produce neomycin. The inventors used the DSM 41550 strain, mutated on several genes including the one responsible for neomycin production and the ΔNeo6 strain, in which the gene responsible for neomycin synthesis has been deleted. Like the wild-type producer strain, all of the culture of mutants *Streptomyces fradiae* were realized in triplicate and supernatants of two cultures were tested. As expected, wild-type and mutant strains did not show the same results. The supernatant from the wild-type producing strain generated a strong bi-phasic signal as shown in FIG. 19*c*. However, with supernatants from non-producer strain either multi-mutated strain (DSM 41550) or single-mutated strain (Δneo6), no signal was observed (FIG. 19*c*). This result showed that biosynthetic pathway of neomycin was inactivated by the mutation. The inventors concluded that with the optimized assay it is possible to detect bactericidal compounds in a supernatant from a culture of a drug producer bacterium.

Antibiotic Resistant Strains or Biofilms as Reporter Cells

Figure 20:
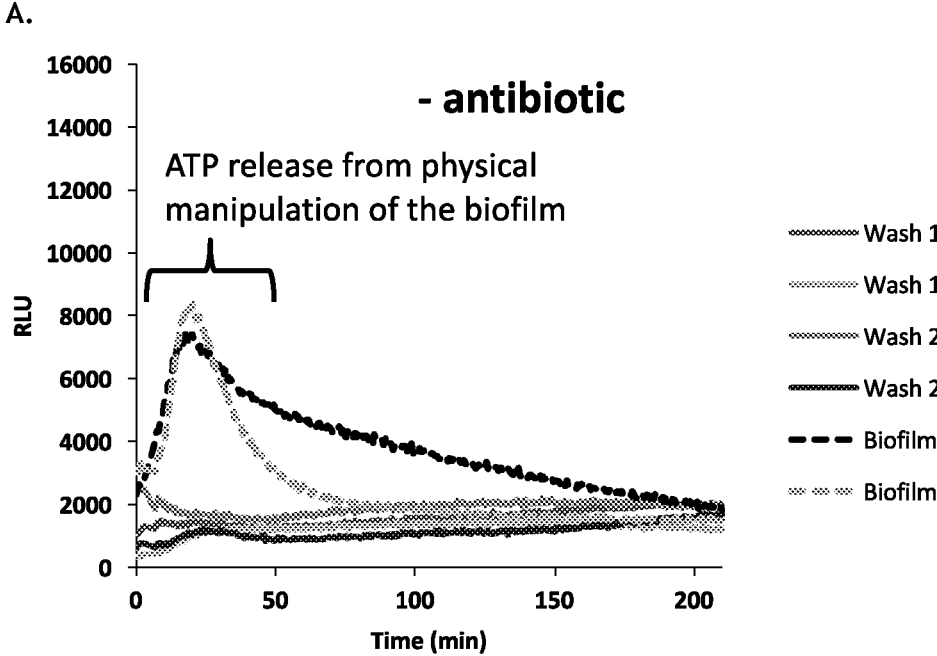
FIG. 20. Drug dependent ATP release from biofilm of the multidrug-resistant *Staphylococcus aureus* USA300 strain. A, Control experiment at 37° C. in absence of antibiotic. Biofilms were washed with MOPS medium prior to be exposed to neomycin in the bioluminescent assay. Biofilms were obtained as described in the Examples section and washed twice with MOPS-G medium. Wash solutions were tested for the presence of ATP with the bioluminescence assay. These solutions did not contain ATP. Washed biofilms were then tested for ATP release. Signals were present in the first 40 min. This ATP release probably originates from shaking of the biofilm in the plate reader with physical perturbation of the biofilm. B, Biofilm response at 37° C. to drug exposure.
Figure 20:
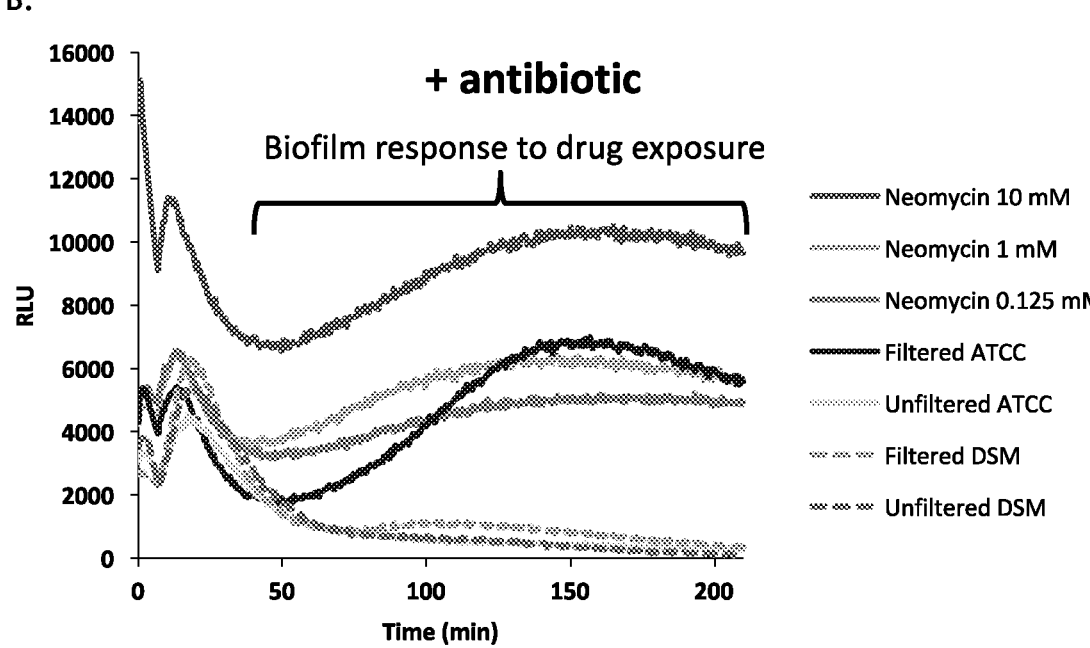
Figure 21:
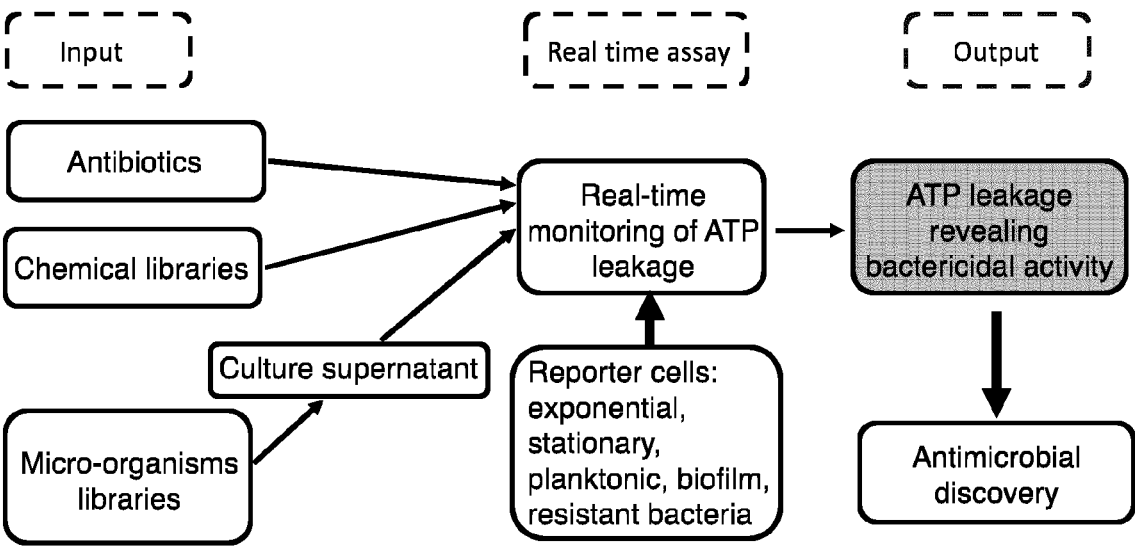
FIG. 21. Bioluminescence assay for antibacterial discovery.

There is a strong interest in identifying new families of bactericidal drugs, which are active against pathogenic strains that have developed resistance to currently available drugs. Finding drugs that would be very efficient against biofilms formed by multidrug resistant strains would also be an advantage. Therefore, the inventors tested if herewith described test would report on drug dependent ATP leakage on biofilm. Following a first release of ATP by the multi-drug-resistant *Staphylococcus aureus* USA300 strain that was found to be drug independent and due to physical manipulation (FIG. 20*a*), the drug neomycin triggered ATP release (FIG. 20*b*). This response was also observed when using the filtered supernatant of the neomycin producer *Streptomyces fradiae* but not for the unfiltered solution further validating the herewith disclosed optimized protocol (FIG. 20*b*). Also, in agreement with inventors' previous findings, the supernatants obtained with the *Streptomyces fradiae* mutant DSM failed to produce a positive response (FIG. 20*b*). These results demonstrate that it is possible to search for novel bactericidal compounds within supernatants of drug producers that would be active on multidrug resistant strains even when present in the form of biofilms (FIG. 21).

Estimation of a MIC Value (Minimum Inhibitory Concentration) from the Bioluminescence Data.

The inventors noticed that there is a delay between the moment they added the antibiotic and the detection of the bioluminescence signal reporting ATP (or analogs) leakage. This delay shortens as with the increase of the concentration of the antibiotic. For most antibiotics the correlation between the concentration and the delay can be fitted by an exponential decay. In present data, the value of the MIC was always found in the entry phase to a plateau where the delay reached its shorter value. This plateau represents a limit where the delay does not change much as the antibiotic concentration is increased. For rationalizing this observation, the inventors subtracted the plateau value of the lag time value of an antibiotic to the lag time for the known MIC of this drug. This difference is then compared to the total amplitude of the change of lag time and given as a percentage noted X in the FIG. 22. The inventors found for the tested set of antibiotics that the value of X was always below 30% of the total observed amplitude (FIG. 22 and table 3 below).

TABLE 3

Figure 22:
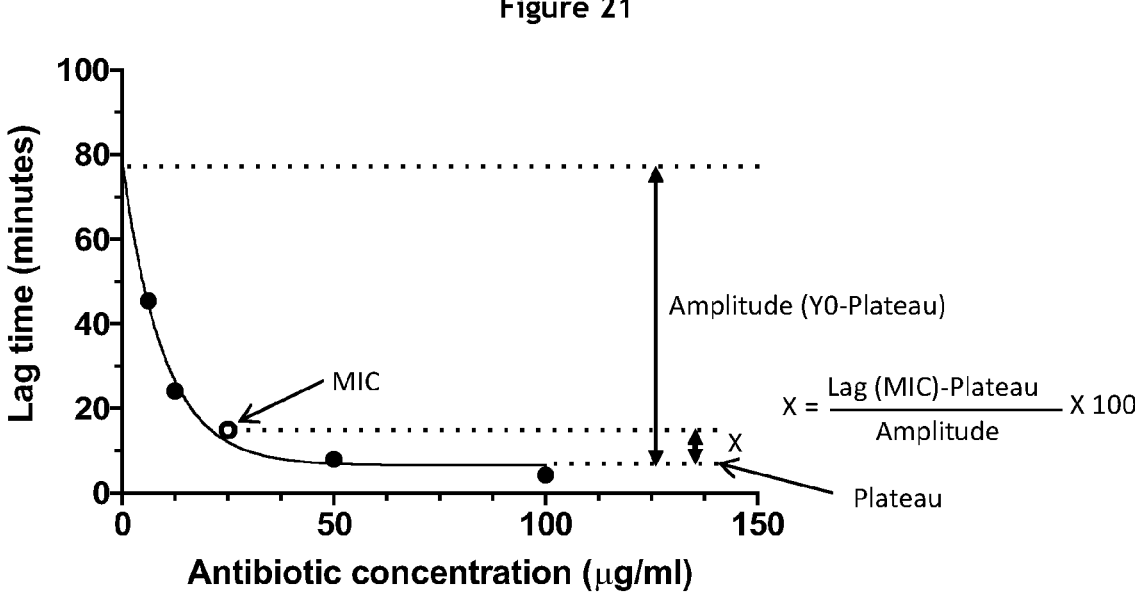
FIG. 22. Analysis of the variation of Lag times as a function of drug concentration and positioning of the MIC value. Values of lags as a function of antibiotic concentration (c) are analyzed as an exponential decay Y=(Y0−Plateau) *exp(−K*c)+Plateau. The measured experimental values of MIC are displayed on the curve by an open circle. For each antibiotic, the value X was calculated and these values are displayed on table 2.
Figure 23:
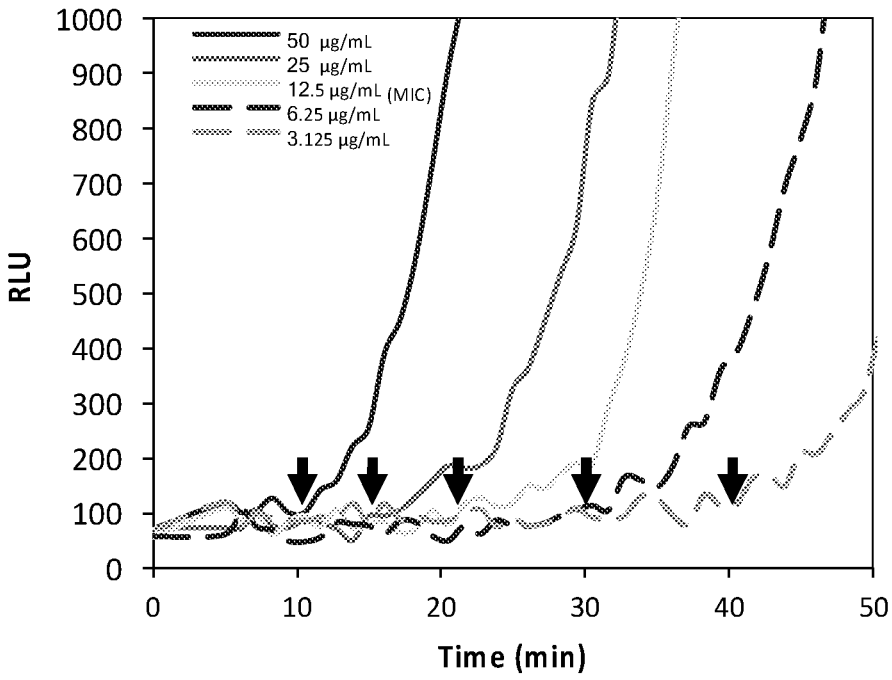
FIG. 23. Representative analysis of lag times as a function of increasing concentrations of antibiotics. Experiments were performed using the strain *E. coli* grown in rich LB media or when indicated in cation-adjusted Muller-Hinton (MH) media. The region of apparition of the biolumines-cence signal for amikacin (from FIG. 8) is shown as an example (left). Time of increase of the signal is indicated by an arrow for each drug concentration. The corresponding fit of the data is shown on the right. Data were analyzed using the equation described in FIG. 22. For each antibiotic, the MIC value that was measured experimentally is displayed by an open circle.
Figure 23:
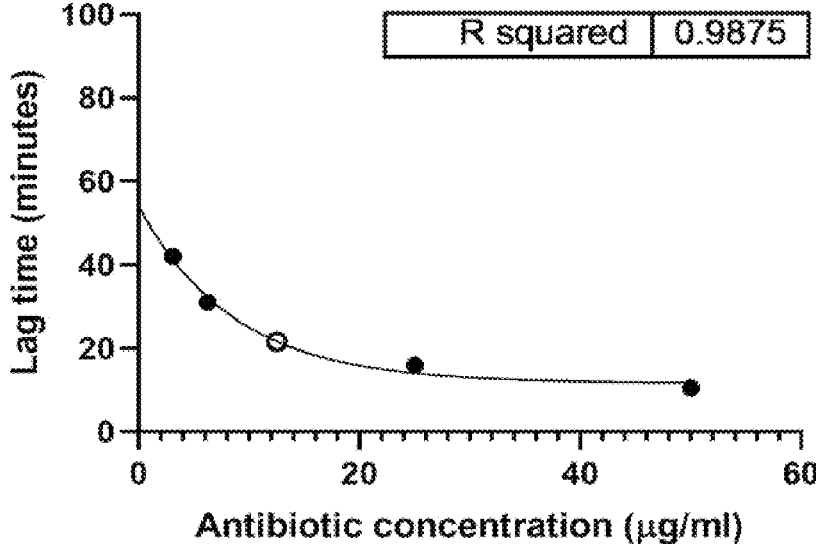
Figure 23:
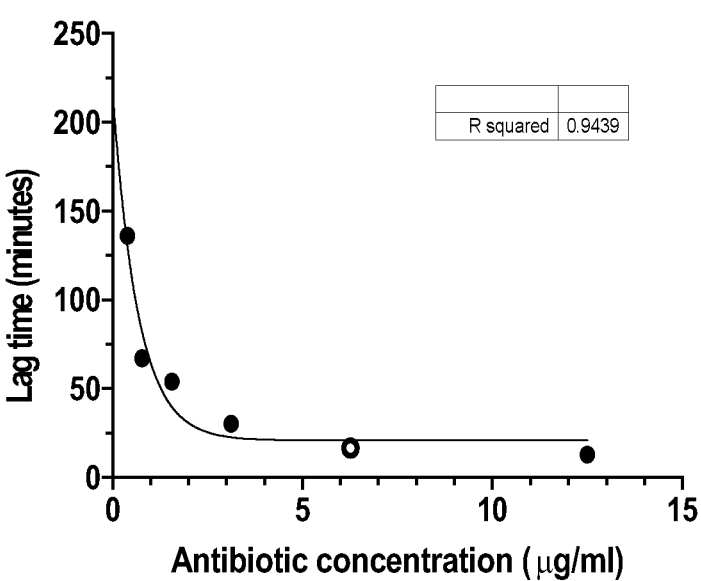
Figure 23:
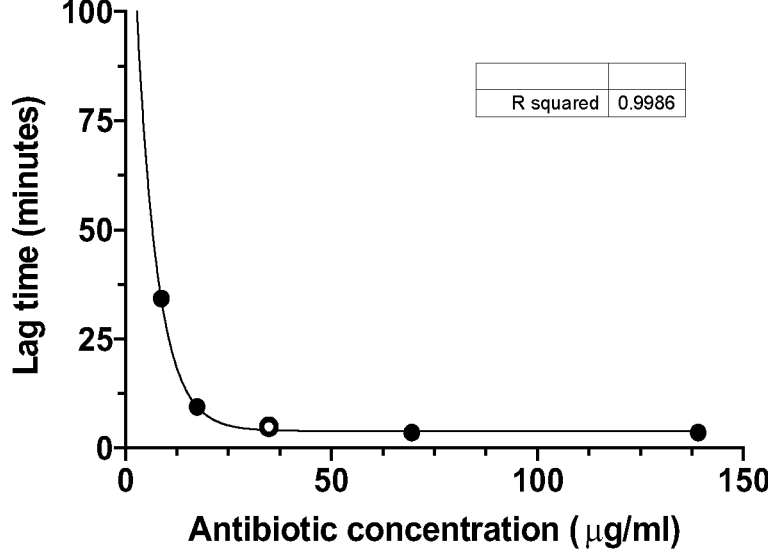
Figure 23:
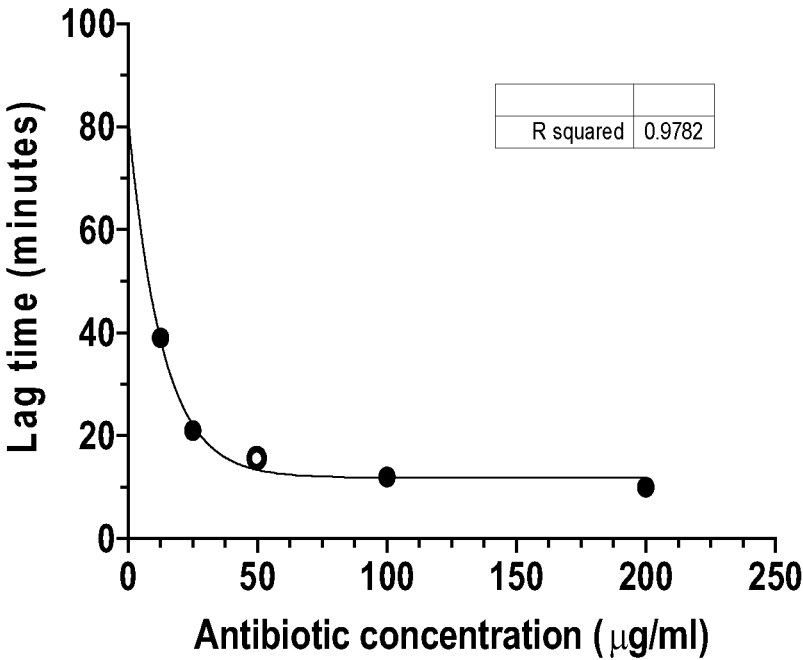
Figure 23:
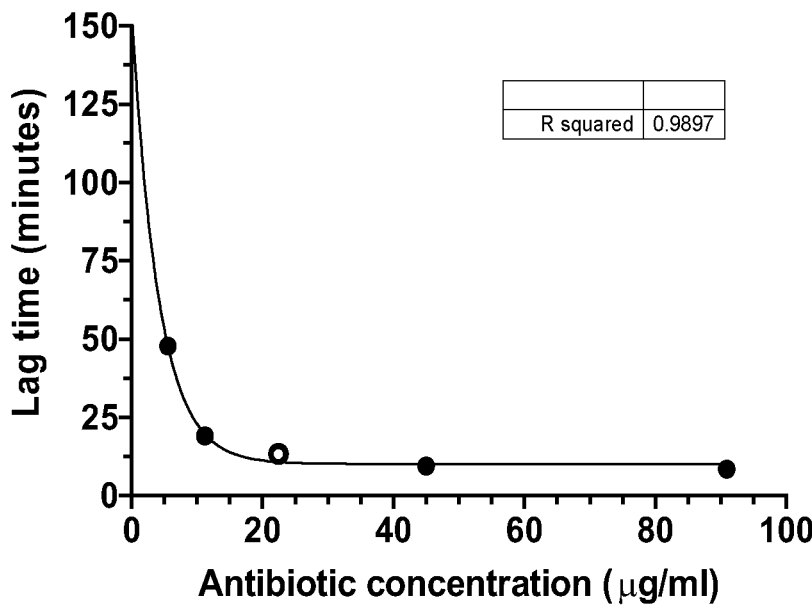
Figure 23:
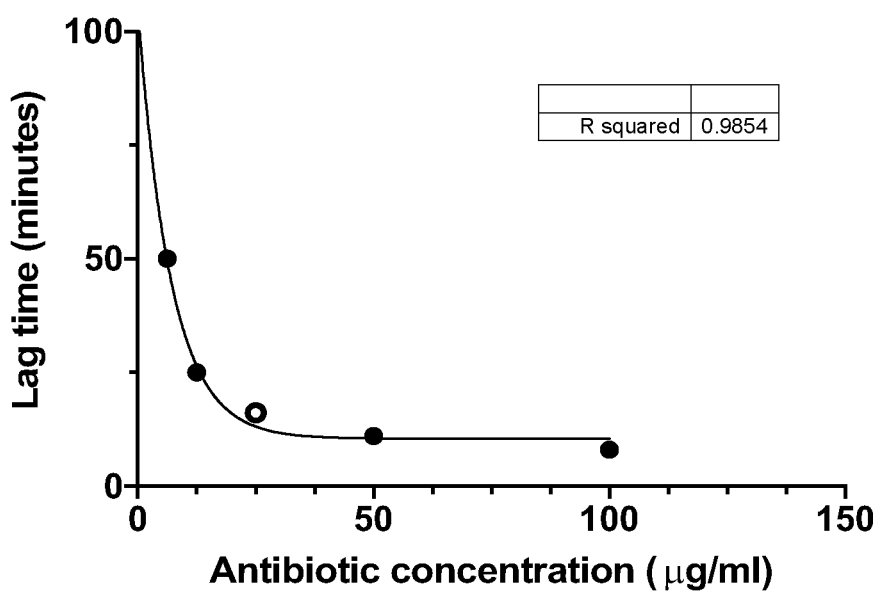
Figure 23:
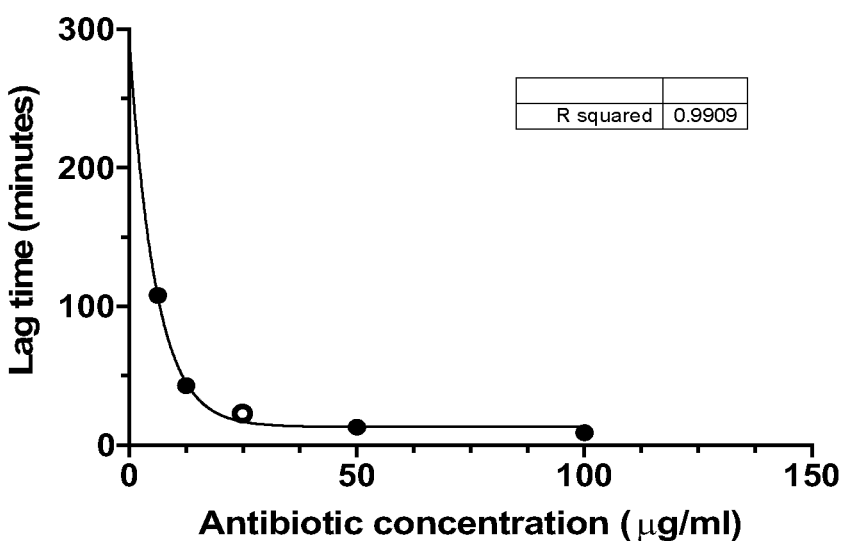
Figure 23:
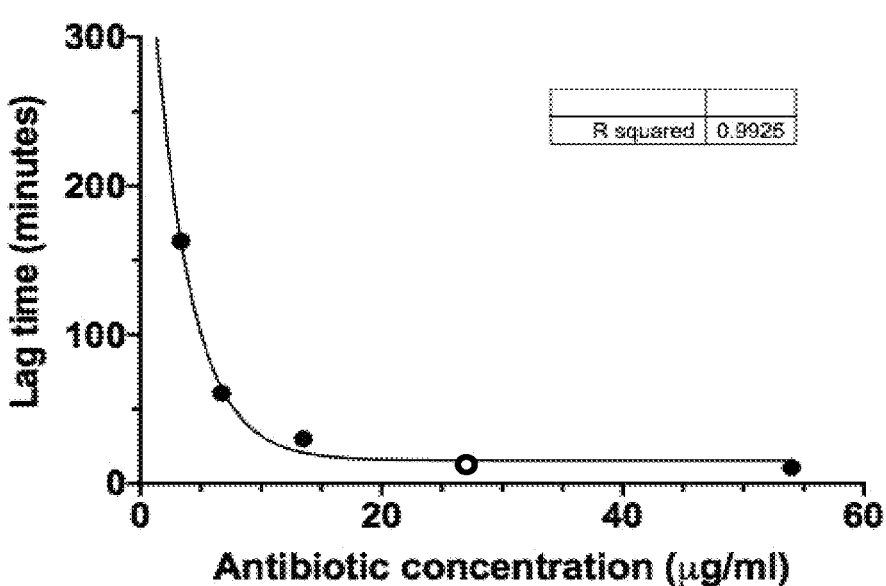
Figure 23:
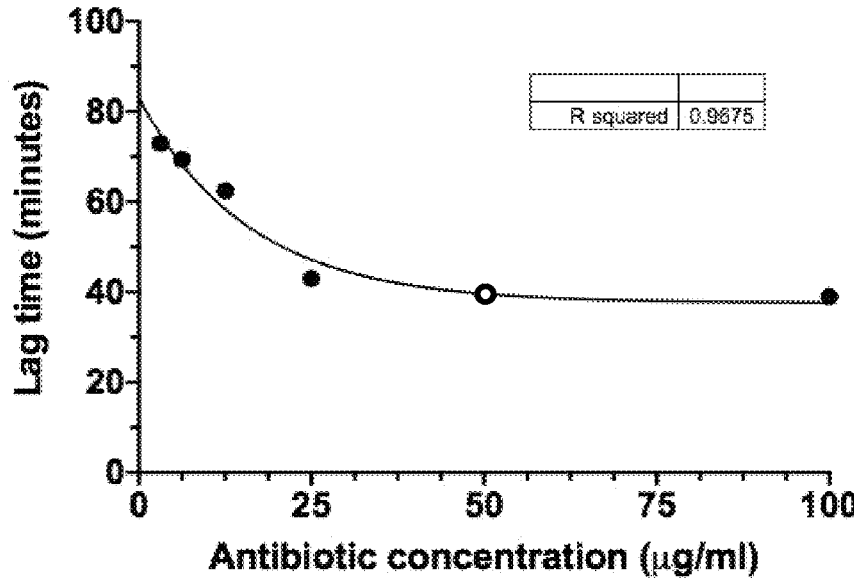
Figure 23:
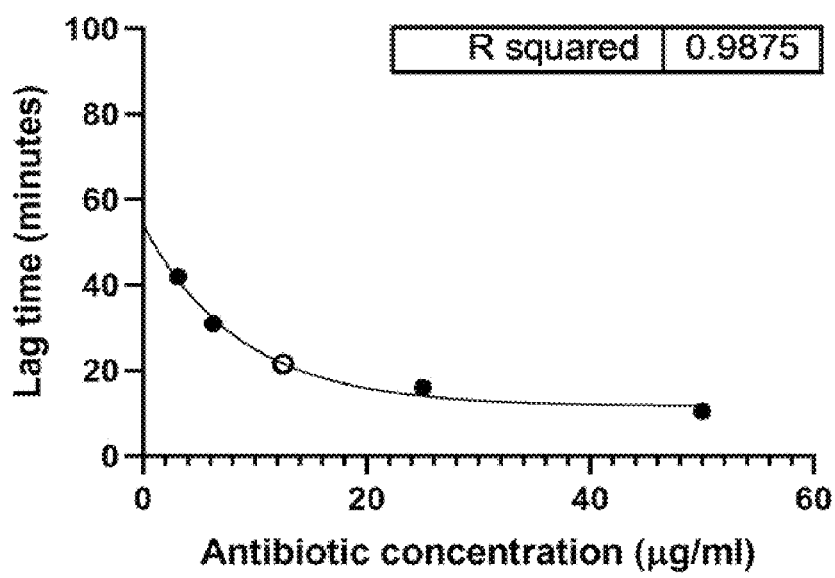
Figure 23:
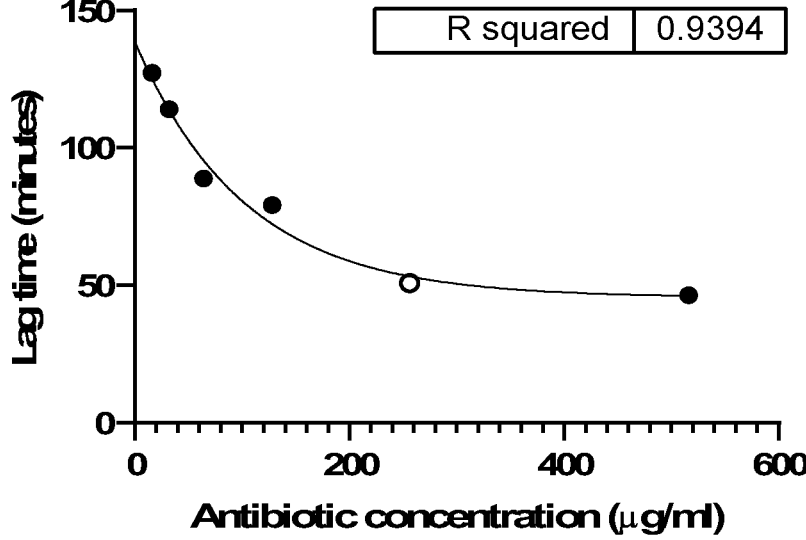
Figure 23:
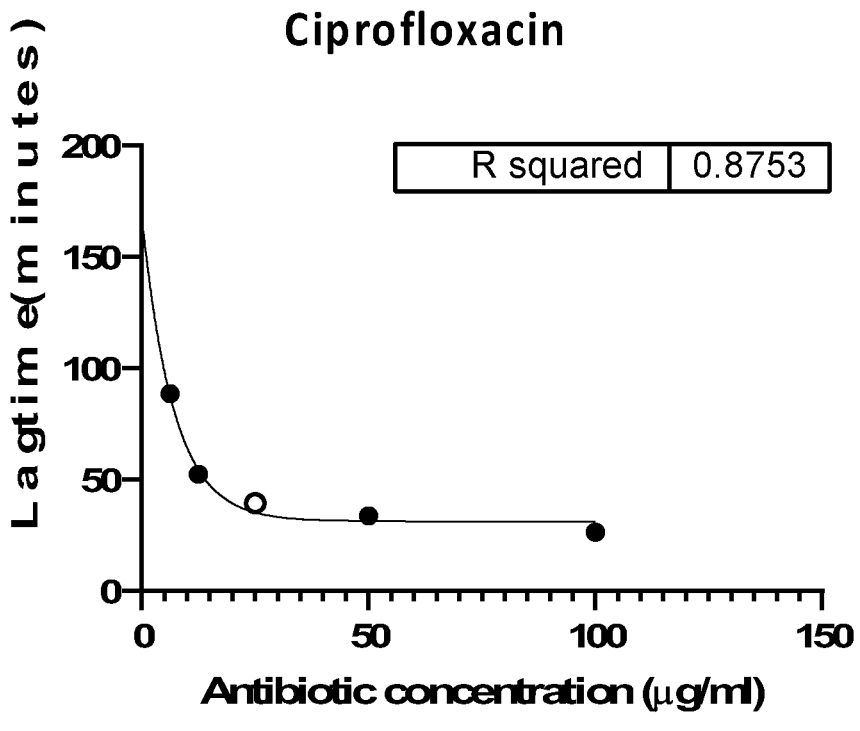
Figure 23:
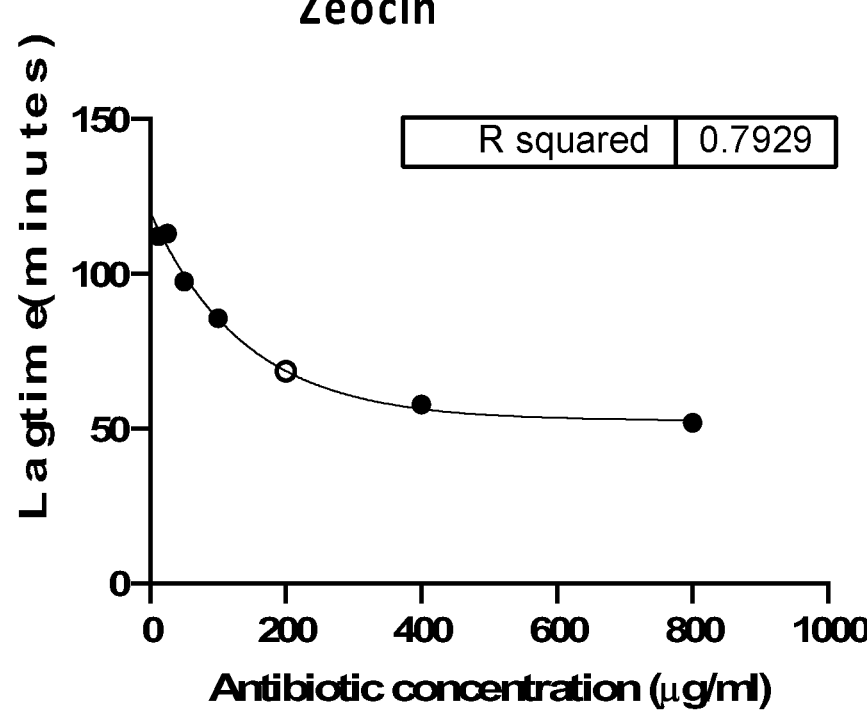
Figure 23:
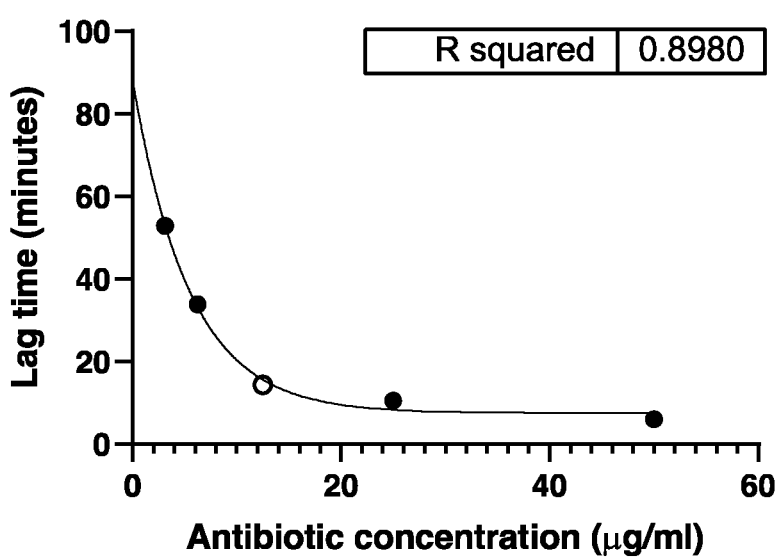
Figure 23:
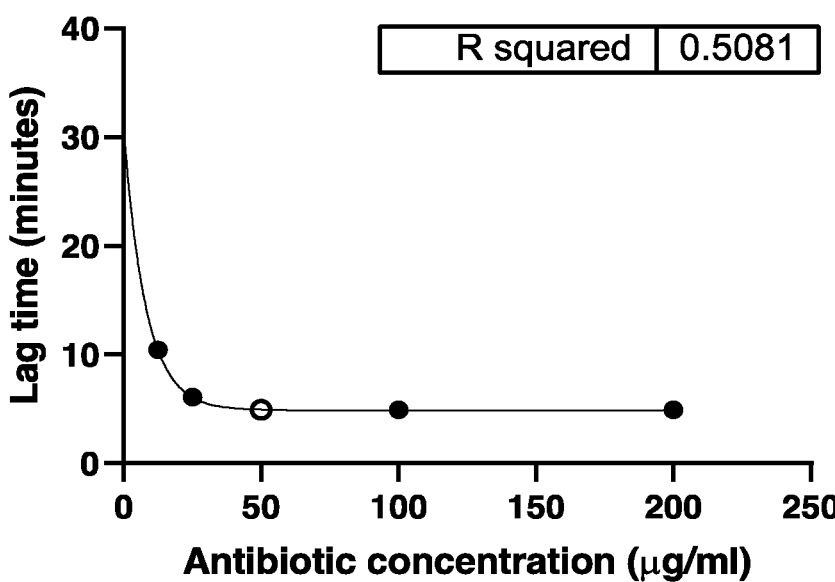
Figure 23:
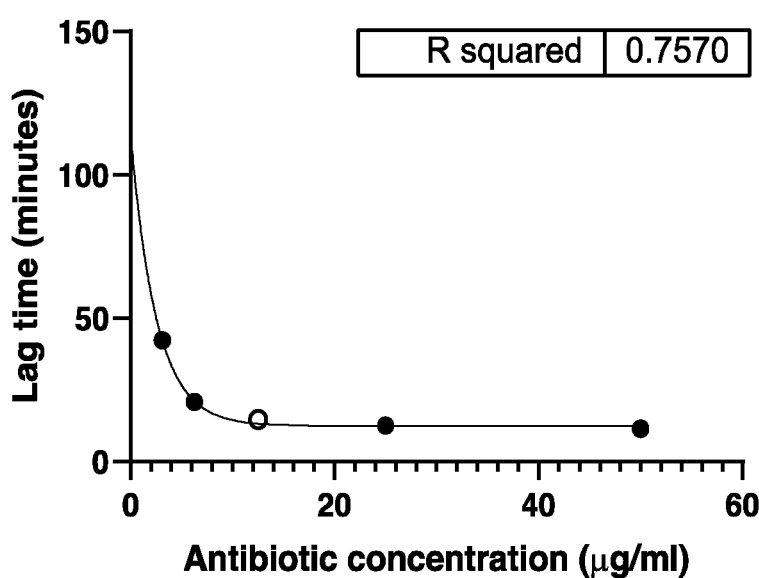
Figure 23:
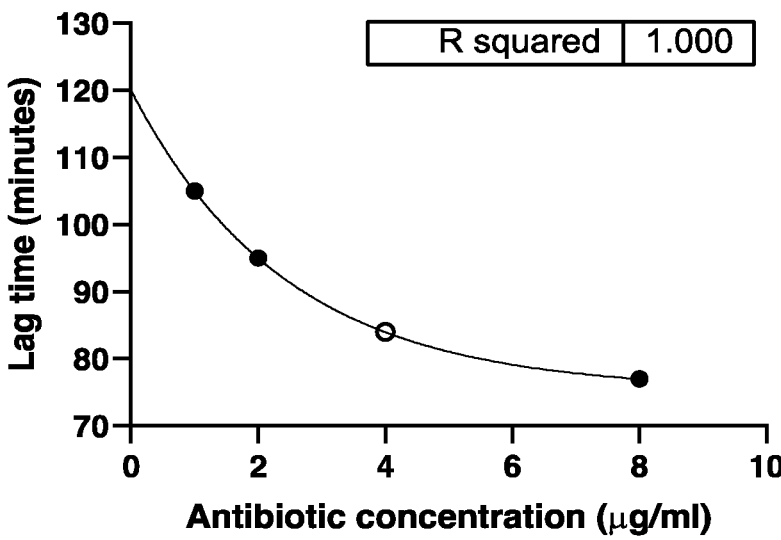
Figure 23:
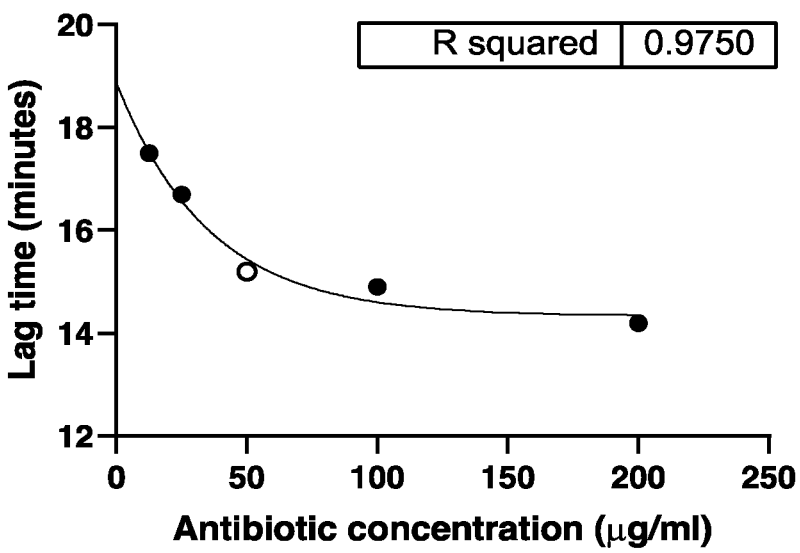
Figure 23:
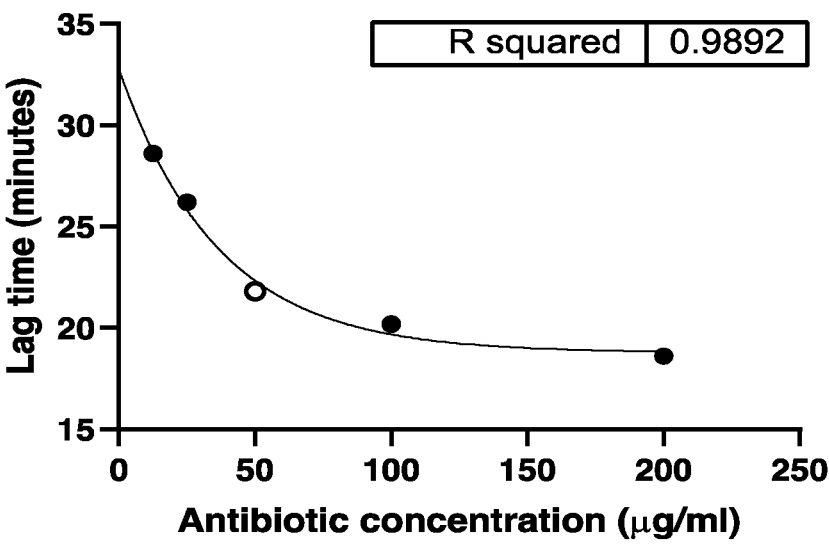
Figure 23:
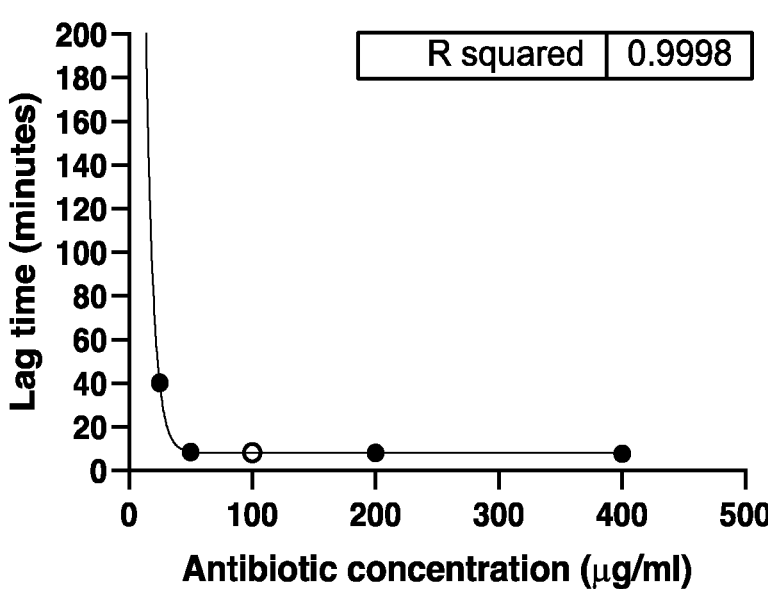
Figure 23:
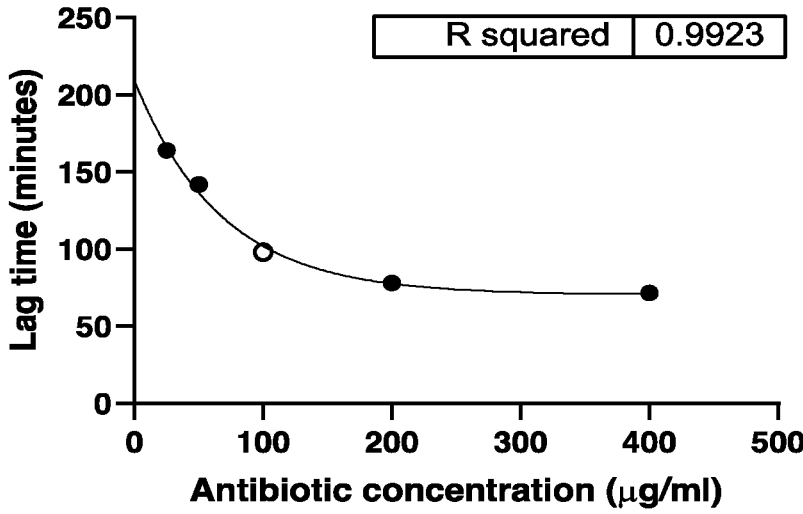
Figure 23:
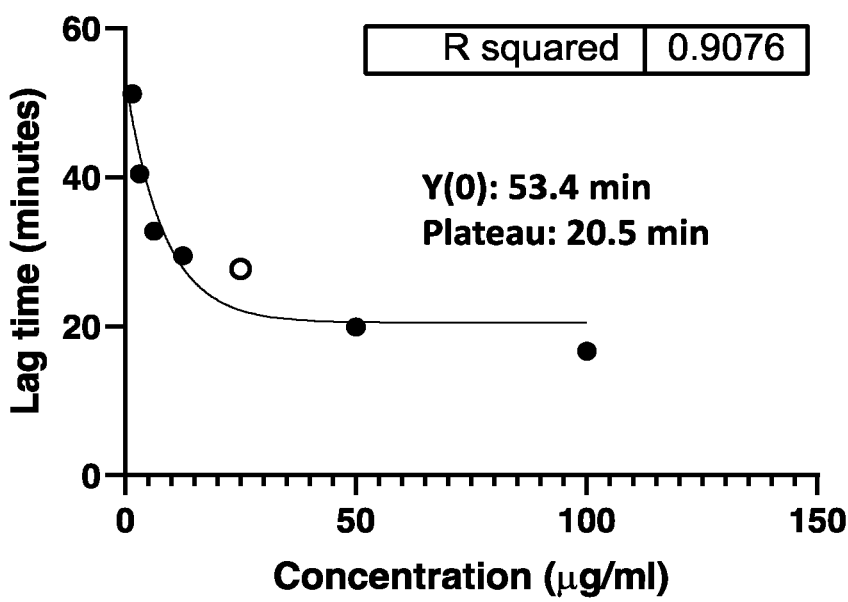
Figure 23:
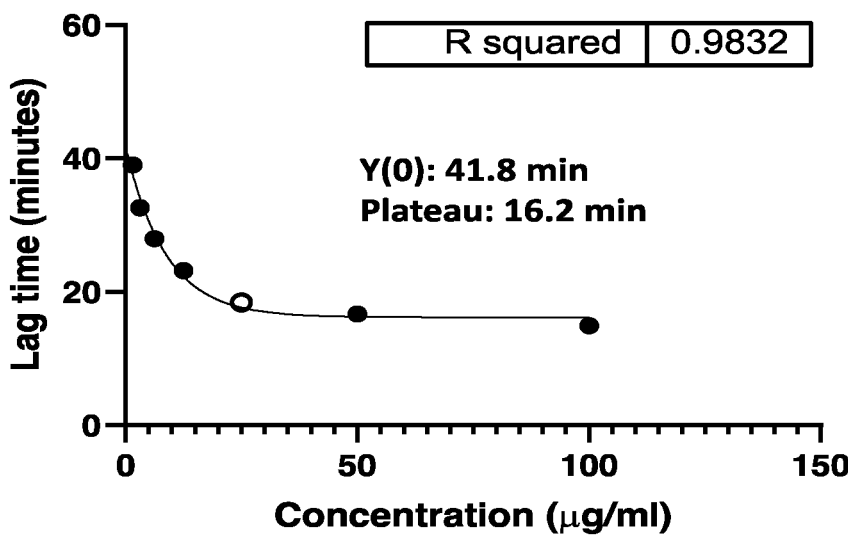
Figure 23:
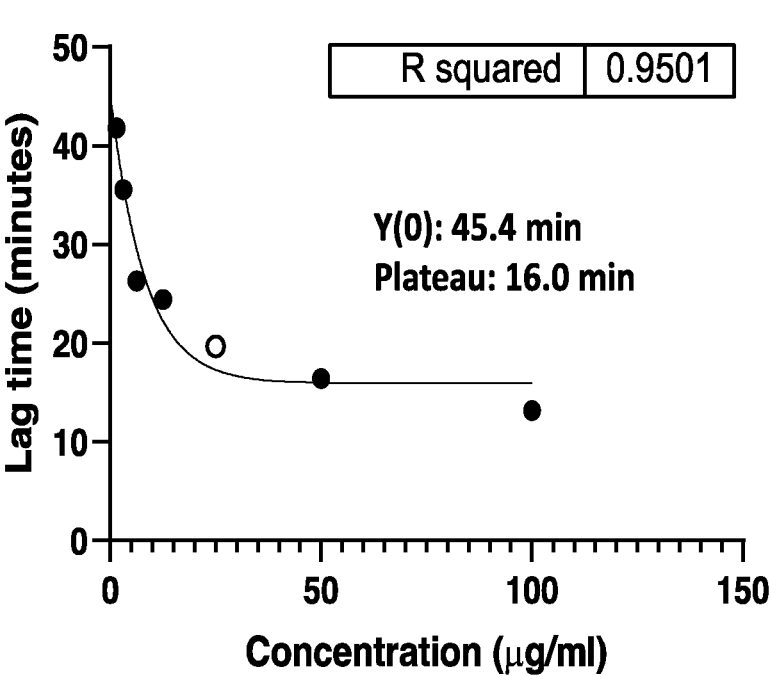

Values obtained for X in the equation
of FIG. 22 for different antibiotics.
The MIC values are always found in a
segment of 30% of the maximum
amplitude of the observed decrease of the
lags. Results for all antibiotics were
obtained using MG1655 *E. coli* cells
at an OD600 of 0.15 in medium LB at
37° C. Also, results obtained from
the data shown in FIG. 3 for neomycin
in medium MH were included.

| Antibiotic | Value of parameter X (%) |
|---|---|
| Kanamycin | 5.9 |
| Neomycin | 2.3 |
| Streptomycin | 1.6 |
| Apramycin | 0 |
| Gentamicin | 0 |
| Cephalexin | 0.6 |
| Zeocin | 23.7 |
| Ofloxacin | 19.4 |
| Acide nalidixic | 5.6 |
| Ampicillin | 3.5 |
| Rifampicin | 4.1 |
| Amikacin | 23.4 |
| Ciprofloxacin | 5.9 |
| Amoxicillin | 8.5 |
| Cefoxitin | 0.1 |
| Ceftriaxone | 2.1 |
| Cefixime | 19 |
| Fosfomycin | 21.6 |
| Bleomycin | 19.8 |
| Neomycin (media MH, OD600 at 0.3 | 21.8 |
| Neomycin (media MH, OD600 at 0.15 | 8.8 |
| Neomycin (media MH, OD600 at 0.015 | 12.8 |

One possible explanation to this observation would be that at this concentration of antibiotic, when reaching the plateau, almost all bacteria are affected by the antibiotic and respond simultaneously. A higher dose of antibiotic will not result in further shortening of the delay as the drug already affects almost all bacteria. Therefore, when testing the susceptibility of a strain to an antibiotic, it is possible to estimate that the MIC will be within a range of lower concentrations corresponding to the segment X.

REFERENCES

1. Berg, J., Hung, Y. P. & Yellen, G. A genetically encoded fluorescent reporter of ATP:ADP ratio. *Nat Methods* 6, 161-6 (2009).
2. Imamura, H. et al. Visualization of ATP levels inside single living cells with fluorescence resonance energy transfer-based genetically encoded indicators. *Proc Natl Acad Sci U A* 106, 15651-6 (2009).
3. Kim, J.-H. et al. A luciferase/single-walled carbon nanotube conjugate for near-infrared fluorescent detection of cellular ATP. *Angew. Chem. Int. Ed Engl.* 49, 1456-1459 (2010).
4. Lee, S. et al. Targeting a bacterial stress response to enhance antibiotic action. *Proc. Natil. Acad. Sci. U.S.A* 106, 14570-5 (2009).
5. Nielsen, L. J., Olsen, L. F. & Ozalp, V. C. Aptamers embedded in polyacrylamide nanoparticles: a tool for in vivo metabolite sensing. *ACS Nano* 4, 4361-4370 (2010).
6. Saito, K. et al. Luminescent proteins for high-speed single-cell and whole-body imaging. *Nat. Commun.* 3, 1262 (2012).
7. Schneider, D. A. & Gourse, R. L. Relationship between growth rate and ATP concentration in *Escherichia coli*: a bioassay for available cellular ATP. *J. Biol. Chem.* 279, 8262-8268 (2004).
8. Tantama, M., Martinez-Frangois, J. R., Mongeon, R. & Yellen, G. Imaging energy status in live cells with a fluorescent biosensor of the intracellular ATP-to-ADP ratio. *Nat. Commun.* 4, 2550 (2013).
9. Yaginuma, H. et al. Diversity in ATP concentrations in a single bacterial cell population revealed by quantitative single-cell imaging. *Sci. Rep.* 4, 6522 (2014).
10. Yoshida, T., Kakizuka, A. & Imamura, H. BTeam, a Novel BRET-based Biosensor for the Accurate Quantification of ATP Concentration within Living Cells. *Sci. Rep.* 6, 39618 (2016).
11. Zheng, D., Seferos, D. S., Giljohann, D. A., Patel, P. C. & Mirkin, C. A. Aptamer nano-flares for molecular detection in living cells. *Nano Lett* 9, 3258-61 (2009).
12. Hall, M. P. et al. Engineered luciferase reporter from a deep sea shrimp utilizing a novel imidazopyrazinone substrate. *ACS Chem. Biol.* 7, 1848-1857 (2012).
13. Yeh, H.-W. et al. Red-shifted luciferase-luciferin pairs for enhanced bioluminescence imaging. *Nat. Methods* 14, 971-974 (2017).
14. de Rautlin de la Roy, Y., Messedi, N., Grollier, G. & Grignon, B. Kinetics of bactericidal activity of antibiotics measured by luciferin-luciferase assay. *J. Biolumin. Chemilumin.* 6, 193-201 (1991).
15. Antibiotic susceptibility diagnostics for the future. *Nat. Microbiol.* 4, 1603 (2019).
16. Roth, H., Amos, H. & Davis, B. D. Purine nucleotide excretion by *Escherichia coli* in the presence of streptomycin. *Biochim. Biophys. Acta* 37, 398-405 (1960).
17. Anand, N. & Davis, B. D. Damage by streptomycin to the cell membrane of *Escherichia coli. Nature* 185, 22-3 (1960).
18. Davis, B. D. Mechanism of bactericidal action of aminoglycosides. *Microbiol. Rev.* 51, 341-50 (1987).

19. Balaban, N. Q., Merrin, J., Chait, R., Kowalik, L. & Leibler, S. Bacterial persistence as a phenotypic switch. *Science* 305, 1622-5 (2004).
20. Keren, I., Shah, D., Spoering, A., Kaldalu, N. & Lewis, K. Specialized persister cells and the mechanism of multidrug tolerance in *Escherichia coli. J. Bacteriol.* 186, 8172-80 (2004).
21. Deris, Z. Z. et al. Probing the Penetration of Antimicrobial Polymyxin Lipopeptides into Gram-Negative Bacteria. *Bioconjug. Chem.* 25, 750-760 (2014).
22. Daugelavičius, R., Bakienė, E. & Bamford, D. H. Stages of Polymyxin B Interaction with the *Escherichia coli* Cell Envelope. *Antimicrob. Agents Chemother.* 44, 2969-2978 (2000).
23. Yao, Z., Kahne, D. & Kishony, R. Distinct single-cell morphological dynamics under beta-lactam antibiotics. *Mol. Cell* 48, 705-712 (2012).
24. Wilson, D. N. Ribosome-targeting antibiotics and mechanisms of bacterial resistance. *Nat. Rev. Microbiol.* 12, 35-48 (2014).
25. Esnault, C. et al. Strong antibiotic production is correlated with highly active oxidative metabolism in *Streptomyces coelicolor* M145. *Sci. Rep.* 7, 200 (2017).
26. Procópio, R. E. de L., Silva, I. R. da, Martins, M. K., Azevedo, J. L. de & Araújo, J. M. de. Antibiotics produced by Streptomyces. *Braz. J. Infect. Dis. Off. Publ. Braz. Soc. Infect. Dis.* 16, 466-471 (2012).
27. Meng, K. et al. Gene cloning and heterologous expression of a serine protease from *Streptomyces fradiae* var. k11. *Can. J. Microbiol.* 53, 186-195 (2007).
28. Neidhardt, F. C., Bloch, P. L. & Smith, D. F. Culture medium for enterobacteria. *J. Bacteriol.* 119, 736-747 (1974).
29. Ling et al., A new antibiotic kills pathogens without detectable resistance; Ling et al., (*Nature.* 2015 Jan. 22; 517(7535):455-9).
30. Chung, H. S., et al. (2009). Rapid beta-lactam-induced lysis requires successful assembly of the cell division machinery. *Proc. Natl. Acad. Sci. U.S.A.* 106, 21872-21877.
31. Gilbert et al., Centrifugation injury of Gram-negative bacteria. Journal of Antimicrobial Chemotherapy. 1991 Apr. 1; 27(4):550-1.
32. Heller et al., A rapid method for post-antibiotic bacterial susceptibility, PLoS ONE 14(1): e0210534 (2019)).
33. Hirokawa et al., Biochimica et Biophysica Acta 1597 (2002) 271-279.
34. England et al., Bioconjug Chem. 2016 May 18; 27(5): 1175-1187. doi:10.1021/acs.bioconjchem.6b00112.
35. Jathoul et al., Angew Chem Int Ed Engl. 2014 Nov. 24; 53(48):13059-63. doi: 10.1002/anie.201405955.
36. Kuchimaru et al., Nat Commun. 2016 Jun. 14; 7:11856. doi: 10.1038/ncomms11856.
37. Lennart NILSSON: "New Rapid Bioassay of Gentamicin Based on Luciferase Assay of Extracellular ATP in Bacterial Cultures", ANTIMICROBIAL AGENTS AND CHEMOTHERAPY, vol. 14, no. 6, 1 Jan. 1978.
38. WO 2019/162301

The invention claimed is:

1. A method for screening compounds for bactericidal activity, comprising:
   a) providing one or more test bacterial sample(s) comprising live bacteria in a culture medium;
   b) adding a mixture of luciferin and a thermostable luciferase to said test bacterial sample(s);
   c) adding a candidate composition to said test bacterial sample(s) 2 to 15 min after step b); and
   d) incubating the test bacterial sample(s) to which the mixture of luciferin and thermostable luciferase and the candidate composition have been added at a temperature between 20 and 60° C., and measuring bioluminescence in real-time;
   wherein the optical density at 600 nm (OD600) of live bacteria in the test bacterial sample(s) after steps a), b) and c) have been performed is at least 0.0002, and
   wherein an increase of bioluminescence measured in a test bacterial sample in step d) is indicative that the candidate composition added to the test bacterial sample in step c) comprises at least one compound with bactericidal activity.

2. The method according to claim 1, wherein said living bacteria of the test sample provided in step a) have not been subjected to a mechanical or chemical stress.

3. The method according to claim 1, wherein the living bacteria in said test sample is selected from the group consisting of antibiotic resistant bacteria; pathogenic bacteria; planktonic cells; and bacteria cells in biofilms.

4. The method according to claim 1, wherein the living bacteria in the test sample are selected in the group consisting of:
   the *Enterococcus faecium, Staphylococcus aureus, Klebsiella pneumoniae, Acinetobacter baumannii, Pseudomonas aeruginosa* and *Enterobacter* spp ("ESKAPE") group of antibiotic-resistant "priority pathogens;"

*Helicobacter pylori, Campylobacter* spp., *Salmonellae, Neisseria gonorrhoeae, Streptococcus* sp., *Haemophilus influenzae, Shigella* spp., *Coagulase*-negative staphylococci, *Mycobacterium tuberculosis, Pseudomonas, Enterococcus faecalis, Escherichia coli, Proteus mirabilis, Serratia marcescens*, and *Citrobacter freundii*.

5. The method according to claim 1, wherein the culture medium used in step a) is a minimal culture medium.

6. The method according to claim 5, wherein the culture medium used in step a) is a minimal culture medium complemented with a source of carbon.

7. The method according to claim 6, wherein the source of carbon is glucose.

8. The method according to claim 1, wherein the OD600 of live bacteria in the test bacterial sample(s) after steps a), b) and c) have been performed is comprised between 0.1 and 0.3.

9. The method according to claim 8, wherein the OD600 of live bacteria in the test bacterial sample(s) after steps a), b) and c) have been performed is comprised between 0.1 and 0.2.

10. The method according to claim 1, wherein in step b), the thermostable luciferase is engineered luciferase having GenBank release 243 accession number AAE43251.1 (SEQ ID NO:1).

11. The method according to claim 1, wherein the candidate composition is
    a) a purified compound or,
    b) a complex mixture.

12. The method according to claim 11, wherein:
    a) the purified compound is a chemical or biological compound, or
    b) the complex mixture is, a bacterial supernatant or extract.

13. The method of claim 12, wherein said complex mixture is filtered before its addition in step c).

14. The method of according to claim 1, wherein said method is performed in a microplate, wherein at the end of step c), said microplate comprises i) at least one screening well comprising a test bacterial sample, a mixture of luciferin and a thermostable luciferase, and a candidate composition and:

ii) at least two negative control wells, one comprising a test bacterial sample, a mixture of luciferin and a thermostable luciferase, but without a candidate composition or a known bactericidal composition, another one comprising the culture medium but without the test bacterial sample, a mixture of luciferin and a thermostable luciferase, a candidate composition or a known bactericidal composition and/or iii) at least one positive control well, comprising a test bacterial sample, a mixture of luciferin and a thermostable luciferase, and a known bactericidal composition or ATP.

15. The method according to claim 1, wherein the incubation temperature in step d) is comprised between 35° and 37° C.

16. The method according to claim 1, wherein the living bacteria of the test sample provided in step a) have not been subjected to centrifugation or osmotic shock.

17. A method for determining the sensitivity of a bacterial sample originating from a subject suffering from a bacterial infection to a group of known antibiotics, comprising:

a) inoculating a bacterial sample originating from a subject suffering from a bacterial infection into a culture medium;

b) dividing the bacterial sample of step a) into several sub-samples, with at least as many samples as the number of known antibiotics to be tested;

c) adding a mixture of luciferin and a thermostable luciferase to each sub-sample;

d) adding each of the group of known antibiotics to one or more sub-sample(s); 2 to 15 min after step c); and e) incubating the sub-sample(s) to which the mixture of luciferin and thermostable luciferase and the known antibiotic have been added at a temperature between 20 and 60° C. and measuring bioluminescence in real-time;

wherein the optical density at 600 nm (OD600) of live bacteria in the sub-samples after steps a), b), c) and d) have been performed is at least 0.0002, and wherein an increase of bioluminescence measured in a sub-sample in step e) is indicative that the bacterial sample originating from a subject is sensitive to the added concentration of known antibiotic added to the sub-sample in step d).

18. The method according to claim 17, wherein in step a):

i) said living bacteria of the sample is amplified, and/or ii) said living bacteria of the sample have not been subjected to a mechanical or chemical stress, and/or iii) said culture medium is a minimal culture medium complemented with glucose.

19. The method according to claim 17, wherein in step b), the thermostable luciferase is the engineered luciferase having GenBank release 243 accession number AAE43251.1 (SEQ ID NO:1).

20. A method for assessing the minimum inhibitory concentration (MIC) of a bactericidal compound comprising:

a) providing at least one test bacterial sample comprising live bacteria in a culture medium;

b) dividing the bacterial sample of step a) into several sub-samples, c) adding a mixture of luciferin and a thermostable luciferase to said sub-samples;

d) adding varying concentrations of a bactericidal compound to said sub-samples 2 to 15 min after step c);

e) incubating the sub-samples to which the mixture of luciferin and thermostable luciferase and the bactericidal compound have been added at a temperature between 20 and 60° C. and measuring bioluminescence in real-time, wherein the optical density at 600 nm (OD600) of live bacteria in the sub-samples after steps a), b), c) and d) have been performed is at least 0.0002;

f) determining for each concentration of bactericidal compound tested the lag time between the time when said bactericidal compound has been added and the time of detection of an increase in the bioluminescence signal, g) representing the lag time in function of the bactericidal compound concentration, h) creating an exponential decay curve fitting the measured points of the lag time in function of the bactericidal compound concentration, i) determining the lowest bactericidal compound concentration in the plateau of the exponential decay fitting curve, j) determining the lag time amplitude of the exponential decay fitting curve, and k) assessing the MIC, wherein the MIC is assessed as comprised between:

the antibiotic concentration corresponding on the exponential decay fitting curve to a lag time equal to (lag time at plateau +0.3× lag time amplitude), and the lowest bactericidal compound concentration in the plateau of the exponential decay fitting curve.

\* \* \* \* \*